US007611719B2

(12) United States Patent
Maas et al.

(10) Patent No.: US 7,611,719 B2
(45) Date of Patent: Nov. 3, 2009

(54) ENTEROVIRUS, VACCINES, MEDICAMENTS AND DIAGNOSTIC KITS

(75) Inventors: Henriette Catharina Gerarda Irene Martina Maas, Amsterdam (NL); Rui Mang, Almere (NL); Petrus Johannes Maria van den Broek, Maarn (NL); Cornelia Maria van der Hoek, Diemen (NL)

(73) Assignee: Amsterdam Institute of Viral Genomics B.V., Amsterdam (NL)

( * ) Notice: Subject to any disclaimer, the term of this patent is extended or adjusted under 35 U.S.C. 154(b) by 0 days.

(21) Appl. No.: 11/285,749

(22) Filed: Nov. 21, 2005

(65) Prior Publication Data

US 2006/0182762 A1 Aug. 17, 2006

Related U.S. Application Data

(63) Continuation of application No. PCT/NL2004/000184, filed on Mar. 12, 2004.

(30) Foreign Application Priority Data

May 21, 2003 (EP) ................................. 03076529

(51) Int. Cl.

| | |
|---|---|
| *A61K 39/125* | (2006.01) |
| *A61K 39/12* | (2006.01) |
| *A61K 39/295* | (2006.01) |
| *A61K 39/00* | (2006.01) |
| *G01N 33/53* | (2006.01) |
| *C12N 9/50* | (2006.01) |
| *C12N 15/00* | (2006.01) |
| *A61K 39/285* | (2006.01) |

(52) U.S. Cl. ............. 424/216.1; 435/320.1; 435/219.1; 435/7.1; 424/204.1; 424/202.1; 424/185.1; 424/186.1; 424/199.1

(58) Field of Classification Search ....................... None
See application file for complete search history.

(56) References Cited

FOREIGN PATENT DOCUMENTS

WO WO 2004/104189 A1 12/2004

OTHER PUBLICATIONS van den Broek et al., Genbank Accession # AY773285, Nov. 3, 2004.*
van den Broek et al., Genbank Accession # AAV41051, Nov. 3, 2004.*
Chen et al., Immunogenicity of enterovirus 70 capsid protein VP1 and its non-overlapping N- and C- terminal fragments, 2005, Antiviral Research, vol. 66, pp. 11-117.*
Tung et al., DNA vaccine contructs against enterovirus 71 elicit immune response in mice, 2007, Genetic Vaccines and Therapy, vol. 5, No. 6, pp. 1-13.*
PCT International Search Report, PCT/NL2004/000184, dated Nov. 3, 2004.
Database EMBL Online!, Mar. 14, 1996, Poyry T. et al., "Poliovirus type 3 20800/Turkey/81 5' untranslated region." XP002294035, retrieved from EBI, Database accession No. L76411.
Database EMBL Online!, Jul. 30, 2003, Brown B.A. et al., "Human coxsackievirus A22 strain Chulman, complete genome." XP002294036, retrieved from EBI, Database accession No. AF499643.
Database UNIPROT Online!, Jul. 15, 1999, Peng J.H. et al., "Genome polyprotein of Porcine enterovirus 9 (strain UKG/410/73)." XP002294037, retrieved from EBI, Database accession No. 041174.
Database UNIPROT Online!, Nov. 1, 1997, Brown B.A. et al., "Genome polyprotein of Human enterovirus 71 (strain 7423/MS/87) (Ev 71)." XP002294038, retrieved from EBI, Database accession No. Q66479.
Database UNIPROT Online!, Aug. 1, 1991, Hughes P.J. et al., "Genome polyprotein of Coxsackievirus A21 (strain Coe)." XP002294039, retrieved from EBI, Database accession No. P22055.
Poyry et al., "Molecular analysis of Coxsackievirus A16 Reveals a New Genetic Group of Enteroviruses," Virology, 1994, pp. 982-987, vol. 202.
Database EMBL Online!, Mar. 16, 1994, Poyry T. et al., "Coxsckievirus A16 G-10, complete genome." XP002265024, retrieved from EBI, Database accession No. U05876.
Database UNIPROT Online!, Mar. 1, 2001, Poyry T. et al., "Capsid protein (Fragment); Human coxsackievirus A2." XP002265025, retrieved from EBI, Database accession No. P82797.
Database UNIPROT Online!, Nov. 1, 1997, Poyry T. et al., "Genome polyprotein of Coxsackievirus A16 (strain G-10)." XP002294040, retrieved from EBI, Database accession No. Q65900.
Ryan et al., "The complete nucleotide sequence of enterovirus type 70: relationships with other members of the Picornaviridae," Journal of General Virology, 1990, pp. 2291-2299, vol. 71.
Database EMBL Online!, Sep. 7, 1992, Ryan M.D. et al., "Enterovirus 70 genomic RNA, complete genome sequence." XP002300237, retrieved from EBI, Database accession No. D00820.
Database SWALL Online!, Oct. 1, 1993, Ryan M.D. et al., "Human Enterovirus 70 (strain J670/71) (EV 70)." XP002265026, retrieved from EBI, Database accession No. P32537.
Nijhuis et al., "Rapid and Sensitive Routine Detection of All Members of the Genus Enterovirus in Different Clinical Specimens by Real-Time PCR," Journal of Clinical Microbiology, Oct. 2002, pp. 3666-3670, vol. 40, No. 10.
Rotbart, "Treatment of picornavirus infections," Antiviral Research, 2002, pp. 83-98, vol. 53.

(Continued)

*Primary Examiner*—Gary B Nickol
*Assistant Examiner*—Benjamin P Blumel
(74) *Attorney, Agent, or Firm*—TraskBritt

(57) ABSTRACT

The invention provides a new enteroviral species call EV79, and functional parts, derivatives and analogues of said virus. Proteinaceous molecules capable of specifically binding EV79, such as isolated or recombinant antibodies, are also herewith provided. A virus and/or proteinaceous molecule of the invention is particularly suitable for diagnosis of an EV79-related disease. Vaccines, pharmaceutical compositions and diagnostic kits comprising said virus or proteinaceous molecule are also provided, as well as methods for producing same. A diagnostic kit of the invention may as well comprise a primer/probe capable of amplifying and/or hybridizing the genome or part thereof of EV79.

16 Claims, 27 Drawing Sheets

OTHER PUBLICATIONS

Patick et al., "in Vitro Antiviral Activity of AG7088, a Protein Inhibitor of Human Rhinovirus 3C Protease," Antimicrobial Agents and Chemotherapy, Oct. 1999, pp. 2444-2450, vol. 43, No. 10.

Huang et al., "Synthesis and testing of Azaglutamine Derivatives as Inhibitors of hepatitis A Virus (HAV) 3C Proteinase," Bioorganic 7 Medicinal Chemistry, 1999, pp. 607-619, vol. 7.

Giordano et al., "Diarrhea and Enteric Emerging Viruses in HIV-Infected Patients," AIDS Research and Human Retroviruses, 1999, pp. 1427-1432, vol. 15, No. 16.

Muir et al., "Molecular Typing of Enteroviruses: Current Status and Future Requirements," Clinical Microbiology Reviews, Jan. 1998, pp. 202-227, vol. 11, No. 1.

Caro et al., "Molecular Strategy for 'serotyping' of human enteroviruses," Journal of General Virolgoy, 2001, pp. 79-91, vol. 82.

Oberste et al., "Typing of Human Enteroviruses by Partial Sequencing of VP1," Journal of Clinical Microbiology, May 1999, pp. 1288-1293, vol. 37, No. 5.

Wu et al., "Protection against lethal enteroviruses 71 infection in newborn mice by passive immunization with subunit VP1 vaccines and inactivated virus," Vaccine, 2002, pp. 895-904, vol. 20.

* cited by examiner

Prima 7
1748 bp

5'UTR Sequence of Prima 7 (position 1- 682)

GGTACCTTTGTACGCCTGTTTTATATCCCTTCCCCATGTAACTTAGAAGATGTTAAACA
AAGTTCAATAGGAGGGGGTACAAACCAGTGCCACCACGAACAAACACTTCTGTTTCCCG
GTGAAGCTACATAGACTGTTCCCACGGTTGAAAGTGGCAGATCCGTTATCCGCTTTGGTA
CTTCGAGAAACCTAGTACCACCTTGGAATCTTCGATGCGTTGCGCTCAGCACTCAACCCC
AGAGTGTAGCTTAGGTCGATGAGTCTGGACGATCCTCACTGGCGACAGTGGTCCAGGCTG
CGTTGGCGGCCTACCTGTGGCGAAAGCCACAGGACGCTAGTTGTGAACAAGGTGTGAAGA
GTCTATTGAGCTACCAAAGAGTCCTCCGGCCCTGAATGCGGCTAATCCCAACCACGGAG
CAAGTGCCCACAAACCAGTGGGTGGCTTGTCGTAATGCGTAAGTCTGTGGCGGAACCGAC
TACTTTGGGTGTCCGTGTTTCCTTTTATTTTTATCATGGCTGCTTATGGTGACAATCTAA
GATTGTTATCATATAGCTATTGAATTGGCCATCCGGTGACTAACAGAGATCTTGCATACC
TGTTTGTTGGTTTTACTAAACTAGATATAATTACATTTAAAACTCTTCTTTATATCATAC
AGTTGAATAGTAGAAAGAGAAA

Fig. 2B

Open reading frame sequence of Prima 7 (position 683- 1748) encoding part of Prima7 polyprotein.

ATGGGAGCTCAAGTTTCAACCCAAAAGACTGGATCTCA
TGAGAACCAGAACATAGCTGCTAGCGGCTCCACTATAAATTACACAACCATCAACTACTA
CAAGGATTCCTATGCCGCTTCAGCCGCAAAGCAGGGTTTCTCCCAAGACCCCTCCAAATT
CACTCAACCTGTTGTGGATGCTCTCAAAGAAACGGCTCCACCACTCAAATCACCATCAGC
TGAAGCATGTGGCTATAGTGATAGGGTTGCCCAGCTAACACTGGGTAATTCCACTATCAC
AACTCAGGAGGCTGCCAACATCACAGTCGGATATGGTGAGTGGCCCGAATATTCCAAGGA
TACTGAGGCCACTGCAGTGGACAAGCCTACTAGACCAGATGTGTCAGTCAATAGGTTCTA
CACACTCCCGGCAAAATTATGGGCCAACAACTCTAAAGGATGGTATTGGAAGTTTCCAGA
TGTTCTCTGCGAGCTGGGAGTGTTTGGTCAAAACGCACAGTACCATTACTTGTATAGGTC
CGGGTTCTGCATACATGTCCAATGTAATGCTAGTAAGTTTCATCAAGGCACACTCTTGGT
GGCTGCTATACCAGAATTAATGCTTGCCAGATCGAGTAATGACACTAACCCAGCCACTGC
CCCCCACCCACCATATAATGCAACACAACCTGGGGAGGCAGGCAAGGAATTTGCTTACCC
CTACATTCTTGATTCCGGCATCCCACTGTCTCAAGCTCTGATCTTCCCTCATCAGTGGAT
CAACTTGCGCACTAACAACTGTGCTACCATAGTTATGCCCTATATCAACTGCTTGCCCTT
TGACTCAGCCCTGAACCACTGCAACTTTTCCTTGGTGGTCATACCAGTTGCACCACTCGC
TTACAATGAAGGAGCCACTACAGCTATACCCATTACTGTAACTGTTGCCCCAATGTGCTC
GGAATTCAGTGGTCTTAGGCAAGCTGTGGTTCAAGGACTACCGGCAGAATTAAAACCTGG
GACTAATCAATTTTTAACTACAGATGATGGTGTCTCAGCACCAATTTTACCTGGTTTCCA
CCCAACCG

Fig. 3

Encoded amino acid sequence

MGAQVSTQKTGSHENQNIAASGSTINYTTINYYKDSYAASAAKQGFSQDPSKFTQPVVDA
LKETAPPLKSPSAEACGYSDRVAQLTLGNSTITTQEAANITVGYGEWPEYSKDTEATAVD
KPTRPDVSVNRFYTLPAKLWANNSKGWYWKFPDVLCELGVFGQNAQYHYLYRSGFCIHVQ
CNASKFHQGTLLVAAIPELMLARSSNDTNPATAPHPPYNATQPGEAGKEFAYPYILDSGI
PLSQALIFPHQWINLRTNNCATIVMPYINCLPFDSALNHCNFSLVVIPVAPLAYNEGATT
AIPITVTVAPMCSEFSGLRQAVVQGLPAELKPGTNQFLTTDDGVSAPILPGFHPT

Fig. 4

Screening faeces patient samples with specific RT-PCR

1st PCR primers are displayed in red (bold)
2nd PCR-primers are displayed orange (underlined)
07-1787 is original sequence of prima7 (first 1787 nt)
F26 and F35 are different patients than the original patient (F27)
For each patient, three clones were analysed

```
           501                                                    550
07-1787    CCTTTTATTT TTATCATGGC TGCTTATGGT GACAATCTAA GATTGTTATC
F26ko103   .......... .......... .......... .......... ..........
F26ko106   .......... .......... .......... .......... ..........
F26ko110   .......... .......... .......... .......... ..........
F27ko120   .......... .......... .......... .......... ..........
F27ko121   .......... .......... .......... .......... ..........
F35ko132   .......... .......... .......... .......... ..........
F35ko136   .......... .......... .......... .......... ..........

551                                                    600
07-1787    ATATAGCTAT TGAATTGGCC ATCCGGTGAC TAACAGAGAT CTTGCATACC
F26ko103   .......... .......... .......... .......... ..........
F26ko106   .......... .......... .......... .......... ..........
F26ko110   .......... .......... .......... .......... ..........
F27ko120   .......... .......... .......... .......... ..........
F27ko121   .......... .......... .......... .......... ..........
F35ko132   .......... .......... .......... .......... ..........
F35ko136   .......... .......... .......... .......... ..........

601                                                    650
07-1787    TGTTTGTTGG TTTTACTAAA CTAGATATAA TTACATTTAA AACTCTTCTT
F26ko103   .......... .......... .......... .......... ..........
F26ko106   .......... .......... .......... .......... ..........
F26ko110   .......... .......... .......... .......... ..........
F27ko120   .......... .......... .......... .......... ..........
F27ko121   .......... .......... .......... .......... ..........
F35ko132   .......... .......... .......... .......... ..........
F35ko136   .......... .......... .......... .......... ..........

651                                                    700
07-1787    TATATCATAC AGTTGAATAG TAGAAAGAGA AAATGGGAGC TCAAGTTTCA
F26ko103   .......... .......... .......... .......... ..........
F26ko106   .......... .......... .......... .......... ..........
F26ko110   .......... .......... .......... .......... ..........
F27ko120   .......... .......... .......... .......... ..........
F27ko121   .......... .......... .......... .......... ..........
F35ko132   .......... .......... .......... .......... ..........
F35ko136   .......... .......... .......... .......... ..........

701                                                    750
07-1787    ACCCAAAAGA CTGGATCTCA TGAGAACCAG AACATAGCTG CTAGCGGCTC
F26ko103   .......... .......... .......... ........TG CTAGCGGCTC
F26ko106   .......... .......... .......... .......... .....GGCTC
F26ko110   .......... .......... .......... ........TG CTAGCGGCTC
F27ko120   .......... .......... .......... .......TGC TAGCCGGCTC
F27ko121   .......... .......... .......... .......... ....CGGCTC
F35ko132   .......... .......... .......... .......... .....GGCTC
F35ko136   .......... .......... .......... .......TG TAGC.GGCTC
```

Fig. 4, contd.

```
            751                                                         800
07-1787     CACTATAAAT TACACAACCA TCAACTACTA CAAGGATTCC TATGCCGCTT
F26ko103    CACTATAAAT TACACAACCA TCAACTATTA CAAGGATTCC TATGCCGCTT
F26ko106    CACTATAAAT TACACAACCA TCAACTATTA CAAGGATTCC TATGCCGCTT
F26ko110    CACTATAAAT TACACAACCA TCAACTATTA CAAGGATTCC TATGCCGCTT
F27ko120    CACTATAAAT TACACAACCA TCAACTATTA CAAGGATTCC TATGCCGCTT
F27ko121    CACTATAAAT TACACAACCA TCAACTACTA CAAGGATTCC TATGCCGCTT
F35ko132    TACTATAAAT TACACAACCA TCAACTACTA CAAGGATTCC TATGCCGCTT
F35ko136    TACTATAAAT TACACAACCA TCAACTACTA CAAGGATTCC TATGCCGCTT 801                                                         850
07-1787     CAGCCGCAAA GCAGGGTTTC TCCCAAGACC CCTCCAAATT CACTCAACCT
F26ko103    CAGCCGCAAA GCAGGATTTC TCCCAAGACC CCTCCAAATT CACTCAACCT
F26ko106    CAGCCGCAAA GCAGGATTTC TCCCAAGACC CCTCCAAATT CACTCAACCT
F26ko110    CAGCCGCAAA GCAGGATTTC TCCCAAGACC CCTCCAAATT CACTCAACCT
F27ko120    CAGCCGCAAA GCAGGATTTC TCCCAAGACC CCTCCAAATT CACTCAACCT
F27ko121    CAGCCGCAAG GCAGGATTTC TCCCAAGACC CTTCCAAATT CACTCAACCT
F35ko132    CAGCCGCAAA GCAGGATTTC TCCCAAGACC CCTCCAAATT CACTCAACCT
F35ko136    CAGCCGCAAA GCAGGATTTC TCCCAAGACC CCTCCAAATT CACTCAACCT 851                                                         900
07-1787     GTTGTGGATG CTCTCAAAGA AACGGCTCCA CCACTCAAAT CACCATCAGC
F26ko103    GTTGTAGATG CTCTCAAAGA AACGGCTCCA CCACTCAAAT CACCATCAGC
F26ko106    GTTGTAGATG CTCTCAAAGA AACGGCTCCA CCACTCAAAT CACCATCAGC
F26ko110    GTTGTAGATG CTCTCAGAGA AACGGCTCCA CCACTCAAAT CACCATCAGC
F27ko120    GTTGTGGATG CTCTCAAAGA AACGGCTCCA CCACTCAAAT CACCATCAGC
F27ko121    GTTGTGGATG CTCTCAAAGA AACTGCTCCA CCACTCAAAT CACCGTCAGC
F35ko132    GTTGTGGATG CTCTCAAAGA AACGGCTCCA CCACTCAAAT CACCATCAGC
F35ko136    GTTGTGGATG CTCTCAAAGA AACGGCTCCA CCACTCAAAT CACCATCAGC 901                                                         950
07-1787     TGAAGCATGT GGCTATAG.T GATA.GGGTT GCCCAGCTAA CACTGGGTAA
F26ko103    TGAAGCATGT GGCTATAG.T GATA.GGGTT GCCCAGCTAA CACTGGGTAA
F26ko106    TGAAGCATGT GGCTATAG.T GATA.GGGTT GCCCAGCTAA CACTGGGTAA
F26ko110    TGAAGCATGT GGCTATAG.T GATA.GGGTT GCCCAGCTAA CACTGGGTAA
F27ko120    TGAAGCATGT GGCTATAGGT GACAAGGGTT GCCCAGCTAA CACTGGGTAA
F27ko121    TGAAGCATGT GGCTATAG.T GATA.GGGTT GCCCAGCTAA CACTGGGTAA
F35ko132    TGAAGCATGT GGCTATAG.T GACA.GGGTT GCCCAGCTAA CACTGGGTAA
F35ko136    TGAAGCATGT GGCTATAG.T GACA.GGGTT GCCCAGCTAA CACTGGGTAA 951                                                        1000
07-1787     TTCCACTATC ACAACTCAGG AGGCTGCCAA CATCACAGTC GGATATGGTG
F26ko103    TTCCACTATT ACAACTCAGG AGGCTGCCAA .......... ..........
F26ko106    TTCCACTATC ACAACTCAGG TGGCTGCCGA .......... ..........
F26ko110    TTCCACTATC ACAACTCAGG AGGCTGCCAA .......... ..........
F27ko120    TTCCACTATC ACAACTCAGG AGGCTGCCAA .......... ..........
F27ko121    TTCCACTATC ACAACTCAGG AGGCTGCCAA .......... ..........
F35ko132    TTCCACTATC ACAACTCAGG AGGCTGCCAA .......... ..........
F35ko136    TTCCACTATC ACAACTCAGG AGGCTGCCAA .......... ..........

1001                                                       1050
07-1787     AGTGGCCCGA ATATTCCAAG GATACTGAGG CCACTGCAGT GGACAAGCCT
F26ko103    .......... .......... .......... .......... ..........
F26ko106    .......... .......... .......... .......... ..........
F26ko110    .......... .......... .......... .......... ..........
F27ko120    .......... .......... .......... .......... ..........
F27ko121    .......... .......... .......... .......... ..........
F35ko132    .......... .......... .......... .......... ..........
F35ko136    .......... .......... .......... .......... ..........
```

Fig. 6

Nucleic acid sequence homology between prima 7 and human enterovirus

| Nucleic Acid Sequence Region (nt) | Target | Identity |
|---|---|---|
| 1-50 | Human rhinovirus 2 | 94% |
| 51-100 | Poliovirus type 2 | 95% |
| 101-150 | Enterovirus 70 | 93% |
| 151-200 | Human enterovirus | 84% |
| 201-250 | Poliovirus type 1 | 100% |
| 251-300 | Poliovirus type 3 | 100% |
| 301-350 | Coxsackievirus A24 | 96% |
| 351-400 | Poliovirus type 3 | 98% |
| 401-450 | Coxsackievirus A24 | 94% |
| 451-500 | Coxsackievirus A21 | 100% |
| 501-550 | Coxsackievirus A21 | 98% |
| 551-600 | Human echovirus 18 | 97% |
| 601-650 | No hint for virus found | |
| 651-700 | Coxsackievirus B2 | 42% |
| 701-750 | Human rhinovirus | 58% |
| 751-800 | Enterovirus 71 | 88% |
| 801-850 | Poliovirus type 1 | 72% |
| 851-900 | No hint for virus found | |
| 901-950 | Coxsackievirus A2 | 54% |
| 951-1000 | Porcine enterovirus 9 | 64% |
| 1001-1050 | Coxsackievirus A14 | 48% |
| 1051-1100 | Enterovirus 71 | 56% |
| 1101-1134 | Poliovirus type 1 | 53% |

Amino acid sequence homology between prima 7 and human enterovirus

| Amino Acid Sequence Region (aa) | Target | Identity |
|---|---|---|
| 1-30 | Coxsackievirus A24 | 90% |
| 31-60 | Enterovirus 70 | 43% |
| 61-90 | Coxsackievirus A16 | 86% |
| 91-120 | Coxsackievirus A16 | 80% |
| 121-150 | Human en

Fig. 8

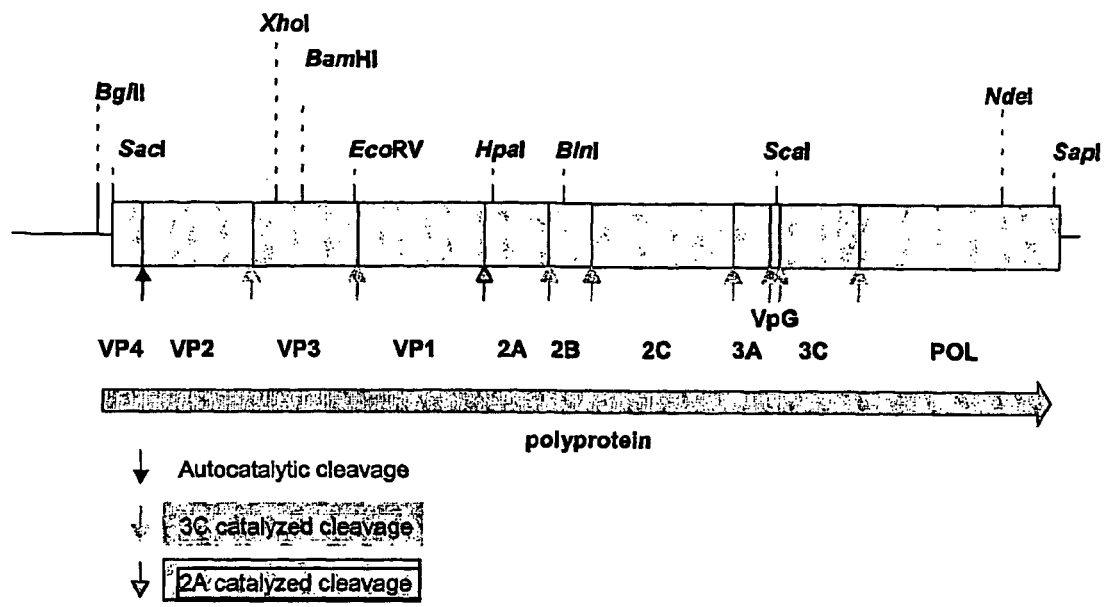

Genomic organisation of Enterovirus Prima 7

The Enterovirus Prima 7 genome comprises 7.419 KB and exhibits the typical organisation of a positive sense single stranded RNA virus. Depicted is a cDNA derivative of the genomic RNA with added restriction sites. The genome posses a single open reading (ORF) of 2193 amino acids (AA), flanked by 5' and 3' untranslated regions (UTR). Within the deduced amino acid sequence of the ORF, domains encoding capsid proteins VP1 to 4, proteases 2A and 3C, a helicase (2C), a RNA dependant polymerase (POL) and non-structural proteins 2B and 3A, were identified on the basis of homology. Between 3A and protease 3C, domain 3B encoding a 22 AA VPg that is covalently attached to the 5' end of the genomic RNA. Predicted 2A and 3C proteolytic cleavage sites separate all these domains, except VP4 and VP2. The cleavage between these two domains is predicted to occur autocatalyticly[2].

Fig. 9

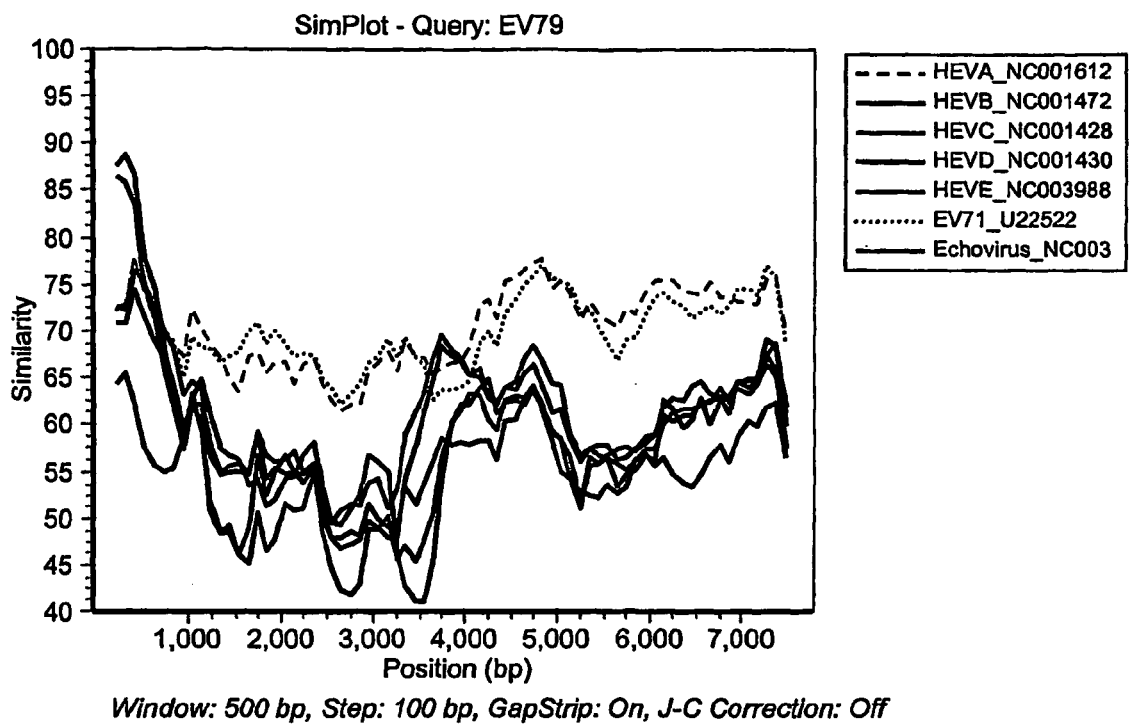

Window: 500 bp, Step: 100 bp, GapStrip: On, J-C Correction: Off

SimPlot analysis of PRIMA 7.
The similarity of the GenBank reference sequences for Coxsackie A16 (NC_001612) human enterovirus A, Coxsackie B1 (NC_001472) human enterovirus B, Coxsackie A21 (NC_001428) human enterovirus C, Enterovirus 70 (NC_001430) human enterovirus D, Plaque A2 virus (NC_003988) human enterovirus E and Enterovirus 71 (AF302996) to PRIMA 7 was determined in a window of 200 nt sliding along the Prima 7 genome in steps on 20 nt and plotted against its position in Prima 7.

Fig. 10

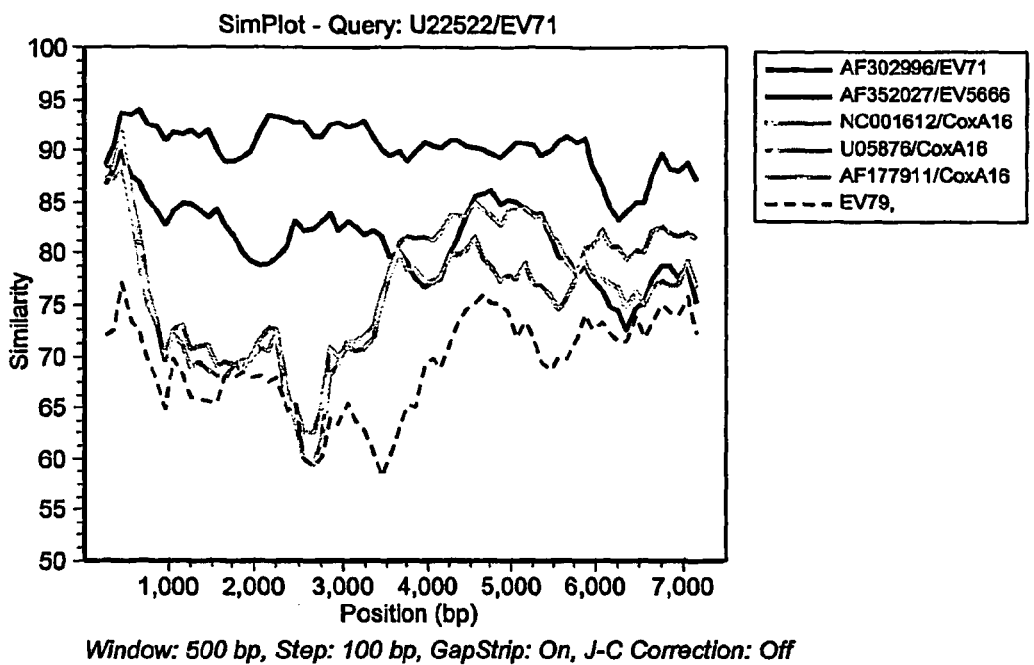

SimPlot analysis of Group A human enteroviruses.

A similar analysis was performed with an alignment all available full-length genome sequences of group A human enteroviruses. Coxsackie A16 Cox (NC_001612), Coxsackie A16 (CAU05876), Coxsackie A16 (AF177911), Enterovirus 71 strain TW/2272/98 (AF119795), Enterovirus71 (AF302996), Enterovirus 5666/sin/002209 (AF352027), and Enterovirus 71 (ETU22522). It is clear from this plot that even in a comparison of the most closely related group A enteroviruses, EV79 exhibits the low sequence identity throughout its genome.

Fig. 11

Hybrid genomes

The first chimeric genome (Fig 11) was generated by a reciprocal recombination in the VP3, fusing nucleotide 2187 of Coxsackie virus A16 (NC_001612) to nucleotide 2129 of EV79. Recombination occurred at the conserved sequence TGGGA, retaining the large open reading frame and generating a hybrid polyprotein.

hybrid CoxA16-EV79 cDNA Restriction map of Coxsackie A16-EV79 hybrid genome.

The Coxsackie A16 derived part is indicated with a single line, whereas the EV79 derived part is indicated with grey boxes. Below is depicted the recombination site with the Coxsackie part in bold capitals and the EV79 derived part is underlined.

ACTGCAATGCTGGGAACCCATGTGATATGGGATTTTGGTTTACAATCATC

Fig. 12

A second chimeric genome was generated by an imaginary reciprocal recombination fusing nucleotide 3773 of Enterovirus 71 (U22522) to nucleotide 3713 of EV79 again creating a hybrid 2b-encoding domain within polyprotein. Recombination could occur within the conserved sequence ATGGA hybrid EV71-EV79 cDNA restriction map of the Enterovirus 71-79 hybrid genome.

The Enterovirus 71 derived part is indicated by a single line and the EV79 derived part is indicated by grey boxes. Below is depicted the crossover site where the EV71 sequences are in bold print and the EV79 sequences are underlined.

TCTTATGGTTAGATGAAGAAGCCATGGAACAGGGGGTCACGGATTACATC

Fig. 13

SimPlot - Query: EV79

Legend:
- ........ hyb1
- − − − Hyb2
- ——— U22522
- ▬▬▬ NC_001612

Window: 200 bp, Step: 20 bp, GapStrip: On, J-C Correction: Off

Similarity plot comparing hybrid- to parental genomes

Hybrid 1 is the result of a crossover between Coxsackie A16 (NC_001612) and EV79. Hybrid 2 is a chimera of Enterovirus 71 (U022522) and EV79. The actual recombination sites can be deduced from the SimPlot graph.

Fig. 14

ENERGY = -215.9

Secondary structure prediction 5' UTR

The predicted secondary structure of nucleotides 1 and 752 (ATG). Five major stem loops are predicted of which nucleotides 456 to 564 correspond to Poliovirus loop V. This particular stem loop confers to Poliovirus the ability to translate efficiency in neuronal cells. This region folds in slightly different secondary structures, differing slightly in enthalpy. Obviously, the presence of RNA-binding proteins could stabilise certain secondary structures in a manner Mfold is unable to predict.

Fig. 15

Multiple 5' UTR sequence alignment of human enteroviruses

```
                       351                                                                      420
D00538CXA21  (329)  CAC-TCCCCACCGGCGACGGTGGCCCAGGCTGCGTTGGCGGCCTACCCATGGCTGAT-GCCGTGGGACGC
D00820EV70   (335)  CAC-CCCACACCGGCGAC-GTGGTCCAGGCTGCGTTGGCGGCCTACCCATGGCT-AGCACCATGGGACGC
D00625PV2    (334)  CGT-TCCTCACCGGCGACGGTGGTCCAGGCTGCGTTGGCGGCCTACCTGTGGCCCAAAGCCACAGGACGC
AJ293918PV3  (334)  CAC-GCCCCACCGGCGACGGTGGCCCAGGCTGCGTTGGCGGCCTACCCATGGCT-ATCACCATGGGACGC
U05876CXA16  (339)  CGATC-CCCACGGGCGACCGTGGCAGTGGCTGCGTTGGCGGCCTGCCTGTGGGGTAA-CCCACAGGACGC
U22521EN71   (335)  CATTC-GCCACGGGCGACCGTGGCGGTGGCTGCGTTGGCGGCCTGCGTATGGGGTAA-CCCATAGGACGG
AY056702PV1  (141)  CGT-TCCCCACCGGTGACGGTGGCCCAGGCTGCGTTGGCGGCCTACCCATGGCT-CACGCCATGGGACGC
EV79         (270)  CGA-TCCTCACTGGCGACAGTGGTCCAGGCTGCGTTGGCGGCCTACCTGTGGCG-AAAGCCACAGGACGC 421                                                                      490
D00538CXA21  (397)  TA-GTTGTGAACAAGGTGTGAAGAGCCTATTGAGCTACTCAAGAGTCCTCCGGCCCCTGAATGCGGCTAA
D00820EV70   (402)  TA-GTTGTGAACAAGGTGCGAAGAGCCTATTGAGCTACCTGAGAGTCCTCCGGCCCCTGAATGCGGCTAA
D00625PV2    (403)  TA-GTTGTGAACAAGGTGTGAAGAGCCTATTGAGCTACCTGAGAGTCCTCCGGCCCCTGAATGCGGCTAA
AJ293918PV3  (402)  TA-GTTGTGAACAAGGTGTGAAGAGCCTATTGAGCTACCCAAGAGTCCTCCGGCCCCTGAATGCGGCTAA
U05876CXA16  (407)  TCTAATATGGACATGGTGCAAAGAGTCTATTCAGCTAGTTAGTAGTCCTCCGGCCCCTGAATGCGGCTAA
U22521EN71   (403)  TCTAATACGGACATGGCGTAGAGTCTATTGAGCTAGTTAGTAGTCCTCCGGCCCCTGAATGCGGCTAA
AY056702PV1  (209)  TA-GTTGTGAACAAGGTGTGAACAGCCTATTGAGCTACCTAAGAGTCCTCCGGCCCCTGAATGCGGCTAA
EV79         (338)  TA-GTTGTGAACAAGGTGTGAAGAGTCTATTGAGCTACCAAAGAGTCCTCCGGCCCCTGAATGCGGCTAA

Attenuated Polio    U           GA
                       491                                                                      560
D00538CXA21  (466)  TCCTAACGACGGAGCAATCGCTCACGACCCAGTGAG--TAGGTTGTCGTAATGCGTAAG-TCTGTGGCGG
D00820EV70   (471)  TCCCAACCACGGAGCAAATGCTCACAATCCAGTGAG--TGGTTTGTCGTAATGCGCAAG-TCTGTGGCGG
D00625PV2    (472)  TCCTAACCACGGAGCAGGCAGTGGCAATCGAGCGAC--CAGCCTGTCGTAACGCGCAAG-TTCGTGGCGG
AJ293918PV3  (471)  TGCTAACCACGGAGCAAGTGTCCTCAACCCAGGGGA--TGGCTTGTCGTAACGCGAAAG-TCTGTGGCGG
U05876CXA16  (477)  TCCTAACTGCGGAGCACATACCCTGGACCCAGGGCG--CAGTGTGTCGTAACGGGCAAC-TCTGCAGCGG
U22521EN71   (473)  TCCTAACTGCGGAGCACATACCCTTAATCCAAAGG---CAGTGTGTCGTAACGGGCAAC-TCTGCAGCGG
AY056702PV1  (278)  TCCTAACGACGGAGCAAGTGCCTTCAGCCCAGAAGG--TAGCTTGTCGTAACGCGAAGGTCTGTGGCGG
EV79         (407)  TCCCAACCACGGAGCAAGTGCCGACAAACCAGTGGG--TGGCTTGTCGTAATGCGTAAG-TCTGTGGCGG 561                                                                      630
D00538CXA21  (533)  AACCGACTACTTTGGGTGTCCGTGTTTCCCTTTATATGCATA--CTGGCTGCTTATGGTGACAATTTACG
D00820EV70   (538)  AACCGACTACTTTGGGTGTCCGTGTTTCCTTTTATTTTATT--ATGGCTGCTTATGGTGACAATCTGAG
D00625PV2    (539)  AACCGACTACTTTGGGTGTCCGTGTTTCCTTTTATTTTACA--ATGGCTGCTTATGGTGACAATTATTG
AJ293918PV3  (538)  AACCGACTACTTTGGGTGTCCGTGTTTCCTTTTATTTTATGTATGGCTGCTTATGGTGACAATCAAAGG
U05876CXA16  (544)  AACCGACTACTTTGGGTGTCCGTGTTTCCTTTTATTCTTATA--CTGGCTGCTTATGGTGACAATTGAAA
U22521EN71   (540)  AACCGACTACTTTGGGTGTCCGTGTTTCTTTTTATTCTTGTA--TTGGCTGCTTATGGTGACAATTAAAG
AY056702PV1  (346)  AACCGACTACTTTGGGTGTCCCGTGTTTGCCCTTATTTTCATT-GTGGCTGCTTGCGG-GACTATAATTG
EV79         (474)  AACCGACTACTTTGGGTGTCCGTGTTTCCTTTTATTTTTATC-ATGGCTGCTTATGGTGA-CAATCTAAG 631                                                                      700
D00538CXA21  (601)  AATTGTTACCATATAGCTA-TTGGATTGGCCACCCAGTGCTGTGCAATAT-ATTTGAGTGCTTCTTCAT
D00820EV70   (606)  A-TTGTTATCATATAGCTA-TTGGATTAGCCATCCGGTGATATCTTGAAATTTGCCATAACTTTTTCAC
D00625PV2    (607)  A-TAGTTATCATAAAGCAAATTGGATTGGCCATCCGGTGA-GAATTTGAT-TATTAAATTACTCTCTTGT
AJ293918PV3  (608)  --TTGTTACCATAAAGCAATTGGATTGGCCATCCGGTGA-GAATCAAACATATTATCTACCTGT-TTGT
U05876CXA16  (612)  GATTGTTACCATATAGCTA-TTGGATTGGCCATCCGGTGTGC-AACAGAGCTATTATTTACCTAT-TTGT
U22521EN71   (608)  AATTGTTACCATATAGCTA-TTGGATTGGCCATCCAGTGTCA-AACAGAGCTATTGTATATCTCT-TTGT
AY056702PV1  (414)  A-TTGCCATCATAAAGCGATTTGGATTGGCCATCCGGAGA-AAGTTAAACACGTTGTTTATTTAT-TCGT
EV79         (542)  A-TTGTTATCATATAGCTA-TTGGATTGGCCATCCGGTGA-CTAACAGAGATCTTGTATACCTGT-TTGT
```

Fig. 15, contd.

Untranslated regions.
The strongest sequence conservation is encountered in the 5'untranslated region (5'UTR), probably because this region plays a pivotal role in the replication and initiation of protein synthesis[22]. Inverted repeats in the 5'UTR allow extensive internal base pairing and the resulting secondary structure can be predicted using the M-Fold program[14]. The putative initiation codon resides immediately downstream of a CT rich tract (position 643-660) which is part of a putative Internal Ribosome Entry Site (IRES) or ribosome landing pad. This ATG corresponds to the one we identified as initiation codon on the basis of homology. All seven other ATGs preceding the putative initiation codon are out of frame and, according to the M-fold prediction, sequestered in hairpin loops.

The region encompassing the fifth stem-loop in the 5' UTRs from Polioviruses 1 (AY056702), 2 (D00625), 3(AJ29398), Enterovirus 70 (D00820), Enterovirus 71 (U022521), Coxsackie A16 (U05876), Coxsackie A21 (D00538) and Enterovirus 79 were aligned with ClustalW. Specific mutations in the stem-loop V (indicated in bold print above the alignment) of polioviruses, preventing proper base pairing in the stem-loop, reduce transcription[20] and decrease neurovirulence[10]. Such attenuated polio strains are used for vaccine production. The implicated nucleotides (marker in yellow) have been conserved in EV79, hence could also be used to create attenuated strains.

Restriction maps of expression plasmids pEV1 and 2

Upon introduction into a suitable *E. coli* host, production of a HisTrx-StrepII bearing VP1 or VP2 fusion protein can be induced by addition of IPTG to the culture medium.

After cell lysis, the expressed proteins can be detected and purified with the appropriate affinity matrices by virtue of their His, Thioredoxin and StrepII affinity tags

Fig. 17

SimPlot – Query: EV79

Legend:
- CoxA16_AAD55085
- Entero5865_AAK1
- HEVA_NP0042242
- Entero5666_AAK3
- HEVB_NP040958
- Polio1_AAM09804
- HEVE_NP653149
- CoxB6S
- HEVC_NP040759
- HEVD_NP040760

Window: 200 bp, Step: 20bp, GapStrip: On, J-C Correction: Off

Similarity distribution in the polyproteins of human Enteroviruses.

The deduced amino acid sequences of Coxsackie A16 (NP_0042242 and AAD55085), Coxsackie B1 (NP_040958), Coxsackie A21 (NP_040759), Coxsackie B6 (Q9QL88), Plaque A2 (NP_653149), Polio 1 (AAM09804), Enterovirus 70 (NP_040760), Enterovirus 5666 (AAB30618) and Enterovirus 5865 (AAK13008) were aligned with ClustalW. The local protein similarity to EV79 to the group A enteroviruses varies from 61 to 92%.

Fig. 18

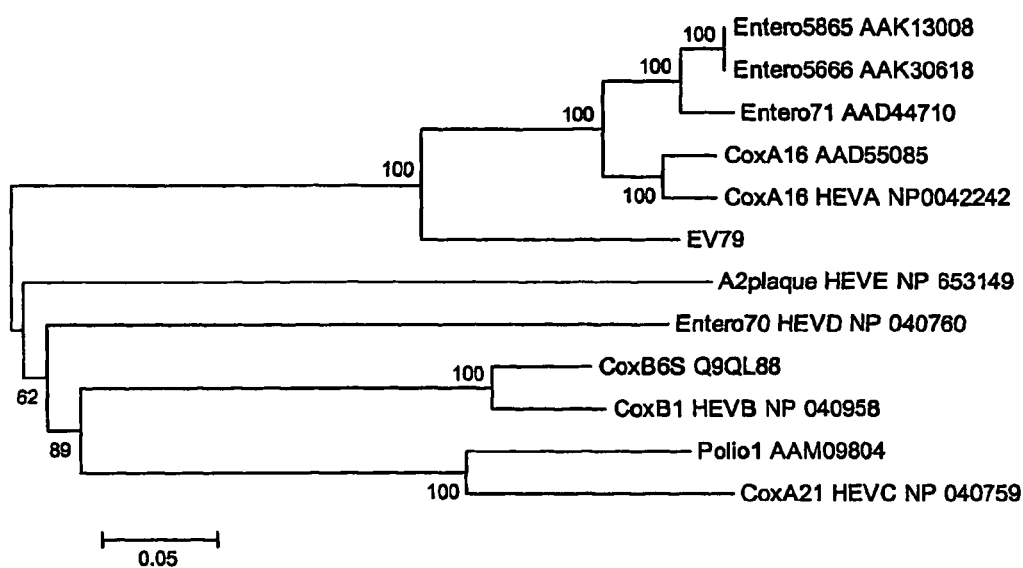

Phylogenetic tree

Sequences were aligned using Clustal-W included in the Vector NTI suite 7 software package (InforMax, Bethesda, U.S.A.). Phylogenetic analyses were performed by the Neighbour-Joining (NJ) method, as implemented in the MEGA 2.1 software package[12]. Kimura's 2-parameter distances[11] were estimated for the nucleotide sequences, and P-distances were used for amino acid sequences. Five hundred bootstrap replicates were analysed. The distance data deduced from the polyprotein alignment was used to construct a phylogenetic tree. Bootstrap values are indicated at the nodes. The distance bar indicates 5% sequence divergence.

Fig. 19

Prima 7 (EV79) nucleotide sequence
TTTAAAACAGCTCTAGGGTTGTTCCCACCCTAGAGGCCCAAGTGGCGGCTAGCACTCTGG
TATTACGGTACCTTTGTGCGCCTGTTTTATATCCCTTCCCCCATGTAACTTAGAAGATAT
TAAACAAAGTTCAATAGGAGGGGGTACAAACCAGTGCCACCACGAACAAACACTTCTGTT
TCCCCGGTGAAGCTACATAGACTGTTCCCACGGTTGAAAGTGGCAGATCCGTTATCCGCT
TTGGTACTTCGAGAAACCTAGTACCACCTTGGAATCTTCGATGCGTTGCGCTCAGCACTC
AACCCCAGAGTGTAGCTTAGGTCGATGAGTCTGGACGATCCTCACTGGCGACAGTGGTCC
AGGCTGCGTTGGCGGCCTACCTGTGGCGAAAGCCACAGGACGCTAGTTGTGAACAAGGTG
TGAAGAGTCTATTGAGCTACCAAAGAGTCCTCCGGCCCCTGAATGCGGCTAATCCCAACC
ACGGAGCAAGTGCCCACAAACCAGTGGGTGGCTTGTCGTAATGCGTAAGTCTGTGGCGGA
ACCGACTACTTTGGGTGTCCGTGTTTCCTTTTATTTTTATCATGGCTGCTTATGGTGACA
ATCTAAGATTGTTATCATATAGCTATTGGATTGGCCATCCGGTGACTAACAGAGATCTTG
CATACCTGTTTGTTGGTTTTACTAAACTAGATATAGTTACATTTAAAACTCTTCTTTATA
TCATACAGTTGAATAGTAGAAAGAGAAAATGGGAGCTCAAGTTTCAACCCAAAAGACTGG
ATCTCATGAGAACCAGAACATAGCTGCTAGCGGCTCCACTATAAATTACACAACCATCAA
CTACTACAAGGATTCCTATGCCGCTTCAGCCGCAAAGCAGGATTTCTCCCAAGACCCCTC
CAAATTCACTCAACCTGTTGTGGATGCTCTCAAAGAAACGGCTCCACCACTCAAATCACC
ATCAGCTGAAGCATGTGGCTATAGTGATAGGGTTGCCCAGCTAACACTGGGTAATTCCAC
TATCACAACTCAGGAGGCTGCCAACATCACAGTCGGATATGGTGAGTGGCCCGAATATTC
CAAGGATACTGAGGCCACTGCAGTGGACAAGCCTACTAGACCAGATGTGTCAGTCAATAG
GTTCTACACACTCCCGGCAAAATTATGGGCCAACAACTCTAAAGGATGGTATTGGAAGTT
TCCAGATGTTCTCTGCGAGCTGGGAGTGTTTGGTCAAAACGCACAGTACCATTACTTGTA
TAGGTCCGGGTTCTGCATACATGTCCAATGTAATGCTAGTAAGTTTCATCAAGGCACACT
CTTGGTGGCTGCTATACCAGAATTAATGCTTGCCAGATCGAGTAATGACACTAACCCAGC
CACTGCCCCCCACCCACCATATAATGCAACACAACCTGGGGAGGCAGGCAAGGAATTTGC
TTACCCCTACATTCTTGACTCCGGCATCCCACTGTCTCAAGCTCTGATCTTCCCTCATCA
GTGGATCAACTTGCGCACTAACAACTGTGCTACCATAGTTATGCCCTATATCAACTGCTT
GCCCTTTGACTCAGCCCTGAACCACTGCAACTTTTCCTTGGTGGTCATACCAGTTGCACC
ACTCGCTTACAATGAAGGAGCCACTACAGCTATACCCATTACTGTAACTGTTGCCCCAAT
GTGCTCGGAATTCAGTGGTCTTAGGCAAGCTGTGGTTCAAGGACTACCGGCAGAATTAAA
ACCTGGGACTAATCAATTTTTAACTACAGATGATGGTGTCTCAGCACCAATTTTACCTGG
TTTCCACCCAACCCCAGAGATGCACATCCCAGGTGAAGTGAAGAACCTCTTAGAAATTTG
CCAAGTGGAGTCTATTCTCGAGGTCAACAACCTTACCACCAATAAAGCAGCTAGCCAACT
CATGACACGCCTGTTGATACCAGTGGAAGCGCAAACTGCAGTGGATGCACTCTGTGCAGC
TTTCAAAGTTGATCCTGGGCGCGATGGGCCTTGGCAATCTACATTAGTGGGTCAGATATG
CAGATACTACACCCAATGGTCAGGATCCCTCGAAGTGACATTCATGTTCACTGGTAGTTT

Fig. 19, contd.

```
TATGGCAACGGGGAAAATGCTCATTGCCTACACCCCACCAGGTGCGCCGCAACCCGCTAA
CAGAAGAATTGCAATGTTAGGGACACATGTAATCTGGGATTTTGGTTTACAATCATCTGT
CACCTTGGTCATCCCCTGGATCAGCAACACGCATTACAGAGCCATGGGTAGTAATGATTA
TTTTGACTACTACTCTGCAGGTATTGTAACAATTTGGTATCAGACCAACTTTGTGGTGCC
ATCAGGAGCCCCAACATCAGCTTACATTATCGCCCTTGCTGCTGCTCAGAAGAACTTTAC
ATTGAGGTTGCCCAAGGACACTGGCGATATCTCACAAACCGCCATCCTGCAAGGTGACCC
TATTGAAGAGGCCATCAACAACACAGTCGCTGGAACACTGAATCGAGCACTGGGAAGTGC
ATCACACACCACAGCCCAAAACACACAGCAAAGTAGCCATCAGATTGGAACAGGAGAAGT
CCCCGCCCTGCAAGCAGCAGAGACTGGGGCTACATCCAACACTTCAGATGAGAACATGTT
GGAAACCCGTTGTGTGATCAACTCCCATAGTGTGGCTGAGACTAGTATCTCGCATTTCTT
CTCCAGAGCTGGGTTAGTTGGTATGCTTGACCTGCTAACGTCAGGGGATACTGATATAGG
GTTCACATCCTGGGACATTGACATCATGGGATTTGTTCAACAGCGTAGGAAACTGGAGAT
GTTCACATACATGAGGTTTGATGCAGAGTTCACTTTCTTAACTGTGGGAGCGACTGGTGC
TGCGCCAGCCACTGTTATCCAATATATGTATGTACCACCAGGTGCACCCAAACCCACCCA
ACGTGATTCCTTTGAATGGCAGACTTCAACTAATCCTTCCATCTTTGTCAAGGTTAGTGA
TCCCCCAGCCCAGGTCTCGGTACCCTTCATGTCACCTGCAGCAGCATATCAATGGTTTTA
TGATGGATACCCTACATTTGGCAATCACCCAACCAATCAAGACTTCAGATACGGAATCTG
TCCCAATAATCTCATGGGACTTTCTGCGTGCGAGTTCTTGGTTCAGAGAAGCTCACCGA
GGCCCTCAGAGTGCGCATCTACATGCGCATCAAGCACGTCAGAGCATGGATTCCTAGACC
ACTTAGGTCGCAGAAATATCTTCTGAAGAATTATCCAAACTTCGATGGGGCTGATGTCAC
ACCTACTAGTGCATCTAGAGCCAATATCACAACAGCTGGCGTGTTTGGTCAACAGTCAGG
GGCAGTCTATGTTGGGAATTATAAAATAGTTAACAGACATCTGGCAACTGAAGCAGACTG
GAATAGTTTAGTCTGGGAAAGCTACAACAGGGACCTCTTAGTGACCAGTGTGAATGCACA
AGGTTGCGATACCATAGCACGTTGCTCGTGCAAGGCAGGTGTTTATTTCTGCAAGTCCAT
GAACAAGCATTATCCTGTCAGTTTCCAAGGACCTGGAATTGTCGAGGTCCAAGCCAATGA
ATTCTATCCACACAGATACCAAACCCACGTTCTACTCGGGCATGGTACATCGATACCAGG
GGACTGTGGTGGTATCCTCAGATGCCAACACGGTGTCATTGGCCTAGTGACCATGGGAGG
TGATGGCTTGGTTGGTTTTGCAGACCTCAGAGACCTGTTTTGGCTCGACGATGAAGCGAT
GGAACAGGGGTCACGGATTACATCAAGGGACTTGGTGATGCTTTTGGTACAGGGTTCAC
TGATTCCATCTCTAGGGAGATCCAGCAACTTAAAAACTACCTCCTAGGTTCAGAAAATGT
GGTAGAGAAGATCCTTAAAGCACTAATCAAAGTAGTTTCAGCATTGGTGATAGTTGTTAG
GAGTGACTATGACCTGGTCACCCTGACCGCAACCCTCGCTTTAATTGGGTGTCACGGAAG
TCCCTGGGCCTGGCTCAAATCCAAAGTTTCCAATCTACTTGACATTCCTATTGCACAAAA
GCAGAGTGACTCATGGCTCAAGAAATTCACAGAAATGGCTAATGCTGCTAGAGGTCTTGA
ATGGATTGCAAATAAAATTAGCAAGTTTATAGACTGGGTGAAAGAGAAGATTGTCCCAGC
```

Fig. 19, contd.

```
AGCTAAAGAAAAGGTGGAGTTCCTCTCCAATCTCAAGCAATTGCCCTTATTAGAGTCCCA
GATCGCCAACATTGAACAGTCAGCAGCTAGTCAGGAAGATTTAGAAAATCTATTCAGTAA
TGTTGCCTACCTAGCCCATTATTGCAGAAAGTTCCAGCCACTCTACGCCTCAGAGGCGAA
GAGGATCTACGCCATGGAGAAAAGAATCAATAATTACATGCAGTTCAAGAGCAAACACCG
AATTGAACCCGTATGTTTAATAATTAGAGGACCCCTGGCACCGGAAAGTCACTGGCAAC
AGGCATTATTGGTAGAGCTATTGCAGAGAAATACCACTCCAGTGTATATTCCTTGCCCCC
AGACCCAGATCACTTTGATGGTTACAAGCAACAAGTGGTTACAGTGATGGATGACCTTTG
CCAAAACCCAGACGGGAAGACATGTCACTCTTTGCCAGATGGTTTCTACAGTAGAGTT
TATACCACCCATGGCTAGCCTAGAGGAAAAGGGTGTCTCATTCACCTCAAAATTTGTGAT
TGCTTCCACCAACTCATCTAACATCATAGTCCCGACTGTCTCAGACAGTGACGCCATTAG
AAGAAGGTTCTACATGGATTGTGACATCGAGGTTCCTGAATCGTTTAGGACACCCCAGGG
AAGGCTAGATGCTGCTAGAGCTGCCAAACTTTGTTCAGAGAACAACACTGCTAACTTCAA
AAAGTGCAGTCCTCTGGTTTGTGGCAAAGCCATTCAACTTAGGGATAGGAAATCAGGAGT
CAGGTACGGTTTGGATTCTGTCGTCTCAGAGCTAATCAGAGAGTACAACAACCGCTCGGC
AGTTGGTAACACTATTGAGGCACTCTTTCAAGGTCCACCCCAATTTAAACCAATTAGAAT
AACCCTTGACAAACCAGCGCCAGATGCAATTAGTGATCTTTTAGCAAGTGTGGATAGTGA
GGAGGTTAGACAATATTGTAGGCACCAGGGGTGGATTATTCCAGAGAAGCCTACCAACAT
TGAAAGACACGTAAATAGGGCTCTGATGATTCTACAATCAGTTACCACTGTGGTTGCAGT
GATTTCACTTGTGTATGTCATCTACAAACTCTTTGCCGGTTTCCAAGGTGCCTACTCGGG
GATGCCCAAGACAGCGGTCAAGAAACCAGTACTGAGAACTGCTGTAGCTCAGGGACCTGG
GCTAGACTTTGCTCTCTCTCTACTGAAGAAGAACATCAGAAAATGCCAGACAGACCAGGG
GCACTTCACCTTGTTAGGAATTAGGGATAGATTAGCTGTGCTCCCAAGACATGCTTCACC
AGGAGACTCAATTTGGATTGAACACAAGCAAATTAAAATTCTGGACGCCGTTGAGCTGGT
CGATGAACAACAAGTCAATCTTGAGCTTACACTGATCACCCTCGACACCAATGAAAAGTT
CAGAGACATTACAAAGTTTATTCCTGAGCAAATTGAAGGGACTGCAGATGCCACCCTTGT
CATCAACACAGAGGCTATGCCATCAATGTTTGTTCCAGTCGGTGATGTCCAGCAATATGG
CTTTCTTAACCTCAGTGGCAAACCAACACACAGAACCATGATGTATAACTTCCCAACCAA
AGCAGGACAGTGTGGAGGAGTGGTCACCTCAGTGGGAAGAATTGTGGGCATCCACATTGG
AGGCAATGGCCGCCAGGGCTTCTGCGCTGCACTCAAACGCAGTTATTTTGCTTCTGAACA
AGGTGAGATTCAATGGATGAAATCCAATAAAGAGACAGGCAATTTCAATATCAATGGTCC
CACTAAAACTAAACTTGAACCCAGTGTTTTCCACGATGTGTTTGAAGGAGTCAAAGAACC
AGCAGTCCTTCACTCCAAAGACAAGAGACTTGAGGTTGATTTGAGACTGCTCTTTTCTC
CAAATACATAGGGAACAAGATGCATGAGCCAGATGAGTACATGATCCAGGCCGCGAACCA
TTATGCAGACCAGCTTAAACAATTGGACATCGATACATCAAAAATGAGCATGGAGGATGC
CTGTTATGGAACAGAATTCCTAGAAGGAATTGATTTGGCAACAAGTGCGGGGTACCCCTA
```

Fig. 19, contd.

```
CAACGCATTAGGCATAAAGAAAAAGGACATTCTGAACCCCCAAACCAGGGATGTGACTAA
AATGAAGATGTACTTGGACAAATATGGTATTGACCTCCCTTACTCCACTTATGTCAAAGA
TGAACTTAGAGCTAAGGATAAAATCAAGAAGGGAAATCTAGACTGATTGAGGCCAGTAG
CATTAATGACTCAGTCTACCTTAGAATGTGCTTTGGCCACTTGTATGAGAAATTCCATGC
AAATCCAGGGACGATCACTGGCTCGGCAGTTGGTTGTAACCCAGACACTTTCTGGAGTAA
AATCCCTATAATGCTTCCTGGTTCCCTCTTTGCCTTTGATTATACTGGGTATGATGCTAG
TCTTTCTCCTGCTTGGTTTAGGGCTTTAGAAATCGTTCTTAAAAGATTAGGTTATGATCA
AGATGCTATCTCACTAATTGAGGGAATCAATCACTCCCATCACATTTACAGAAACCAAAC
GTACTGTGTAATGGGTGGGATGCCATCTGGGTGTTCTGGTACTAGCATTTTCAATTCTAT
GATTAACAACATTATTATCAGGACTCTTCTAATCAGAACCTTTAAAGGAATTGATTTGGA
TGAATTAAATATGATTGCATATGGAGATGATGTTCTTGCTAGTTACCCTTTCCCTATTGA
TTGTGCTGAACTTGCAAAAACAGGATTGGAATATGGTTTAGTCATGACACCGGCTGACAA
ATCTACTTGTTTCAATGAGGTAAATTGGGAAAATGCAACGTTCCTCAAGAGGGGATTCAA
ACCAGATGAGCAATATCCGTTCCTCATCCACCCAACCATGCCGATGAAGGAAATACACGA
GTCCATTCGTTGGACTAAAGACCCACGTAACACACAAGATCACGTGCGGTCACTGTGCCT
CCTAGCATGGCATAATGGTAGGGAAACCTATGAGGAATTTGTTGACAAAATTAGAACTGT
ACCAATTGGCAAAGTCTTAGCTCTTCCAAATTATGATAACTTGAGAAGAAATTGGCTTGA
ACTGTTTTAAATAATGATCTAAAATAGTTTCAATTGGCAACATCTTTGGTGCCCCCTGGG
CTTGACAAAGTCACCAAAGCTCAATTCCCCCAACCCAGTGGGTAAAAAAAAAAAAAA
```

Fig. 20

Deduced amino acid sequence EV79

MGAQVSTQKTGSHENQNIAASGSTINYTTINYYKDSYAASAAKQDFSQDPSKFTQPVVDA
LKETAPPLKSPSAEACGYSDRVAQLTLGNSTITTQEAANITVGYGEWPEYSKDTEATAVD
KPTRPDVSVNRFYTLPAKLWANNSKGWYWKFPDVLCELGVFGQNAQYHYLYRSGFCIHVQ
CNASKFHQGTLLVAAIPELMLARSSNDTNPATAPHPPYNATQPGEAGKEFAYPYILDSGI
PLSQALIFPHQWINLRTNNCATIVMPYINCLPFDSALNHCNFSLVVIPVAPLAYNEGATT
AIPITVTVAPMCSEFSGLRQAVVQGLPAELKPGTNQFLTTDDGVSAPILPGFHPTPEMHI
PGEVKNLLEICQVESILEVNNLTTNKAASQLMTRLLIPVEAQTAVDALCAAFKVDPGRDG
PWQSTLVGQICRYYTQWSGSLEVTFMFTGSFMATGKMLIAYTPPGAPQPANRRIAMLGTH
VIWDFGLQSSVTLVIPWISNTHYRAMGSNDYFDYYSAGIVTIWYQTNFVVPSGAPTSAYI
IALAAAQKNFTLRLPKDTGDISQTAILQGDPIEEAINNTVAGTLNRALGSASHTTAQNTQ
QSSHQIGTGEVPALQAAETGATSNTSDENMLETRCVINSHSVAETSISHFFSRAGLVGML
DLLTSGDTDIGFTSWDIDIMGFVQQRRKLEMFTYMRFDAEFTFLTVGATGAAPATVIQYM
YVPPGAPKPTQRDSFEWQTSTNPSIFVKVSDPPAQVSVPFMSPAAAYQWFYDGYPTFGNH
PTNQDFRYGICPNNLMGTFCVRVLGSEKLTEALRVRIYMRIKHVRAWIPRPLRSQKYLLK
NYPNFDGADVTPTSASRANITTAGVFGQQSGAVYVGNYKIVNRHLATEADWNSLVWESYN
RDLLVTSVNAQGCDTIARCSCKAGVYFCKSMNKHYPVSFQGPGIVEVQANEFYPHRYQTH
VLLGHGTSIPGDCGGILRCQHGVIGLVTMGGDGLVGFADLRDLFWLDDEAMEQGVTDYIK
GLGDAFGTGFTDSISREIQQLKNYLLGSENVVEKILKALIKVVSALVIVVRSDYDLVTLT
ATLALIGCHGSPWAWLKSKVSNLLDIPIAQKQSDSWLKKFTEMANAARGLEWIANKISKF
IDWVKEKIVPAAKEKVEFLSNLKQLPLLESQIANIEQSAASQEDLENLFSNVAYLAHYCR
KFQPLYASEAKRIYAMEKRINNYMQFKSKHRIEPVCLIIRGPPGTGKSLATGIIGRAIAE
KYHSSVYSLPPDPDHFDGYKQQVVTVMDDLCQNPDGKDMSLFCQMVSTVEFIPPMASLEE
KGVSFTSKFVIASTNSSNIIVPTVSDSDAIRRRFYMDCDIEVPESFRTPQGRLDAARAAK
LCSENNTANFKKCSPLVCGKAIQLRDRKSGVRYGLDSVVSELIREYNNRSAVGNTIEALF
QGPPQFKPIRITLDKPAPDAISDLLASVDSEEVRQYCRHQGWIIPEKPTNIERHVNRALM
ILQSVTTVVAVISLVYVIYKLFAGFQGAYSGMPKTAVKKPVLRTAVAQGPGLDFALSLLK
KNIRKCQTDQGHFTLLGIRDRLAVLPRHASPGDSIWIEHKQIKILDAVELVDEQQVNLEL
TLITLDTNEKFRDITKFIPEQIEGTADATLVINTEAMPSMFVPVGDVQQYGFLNLSGKPT
HRTMMYNFPTKAGQCGGVVTSVGRIVGIHIGGNGRQGFCAALKRSYFASEQGEIQWMKSN
KETGNFNINGPTKTKLEPSVFHDVFEGVKEPAVLHSKDKRLEVDFETALFSKYIGNKMHE
PDEYMIQAANHYADQLKQLDIDTSKMSMEDACYGTEFLEGIDLATSAGYPYNALGIKKKD
ILNPQTRDVTKMKMYLDKYGIDLPYSTYVKDELRAKDKIKKGKSRLIEASSINDSVYLRM
CFGHLYEKFHANPGTITGSAVGCNPDTFWSKIPIMLPGSLFAFDYTGYDASLSPAWFRAL
EIVLKRLGYDQDAISLIEGINHSHHIYRNQTYCVMGGMPSGCSGTSIFNSMINNIIIRTL
LIRTFKGIDLDELNMIAYGDDVLASYPFPIDCAELAKTGLEYGLVMTPADKSTCFNEVNW
ENATFLKRGFKPDEQYPFLIHPTMPMKEIHESIRWTKDPRNTQDHVRSLCLLAWHNGRET
YEEFVDKIRTVPIGKVLALPNYDNLRRNWLELF

Fig. 21
Restriction maps of pLXRN and its derivative pEV79
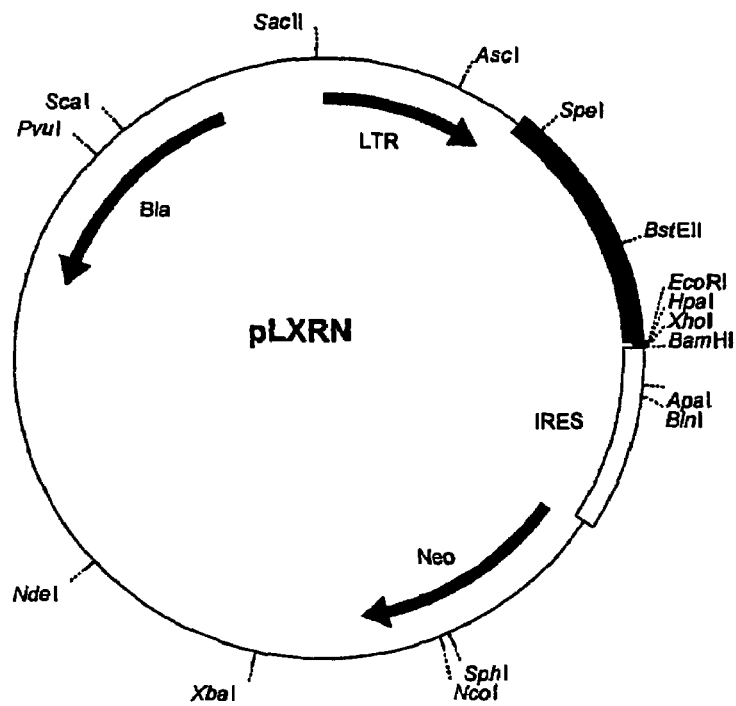
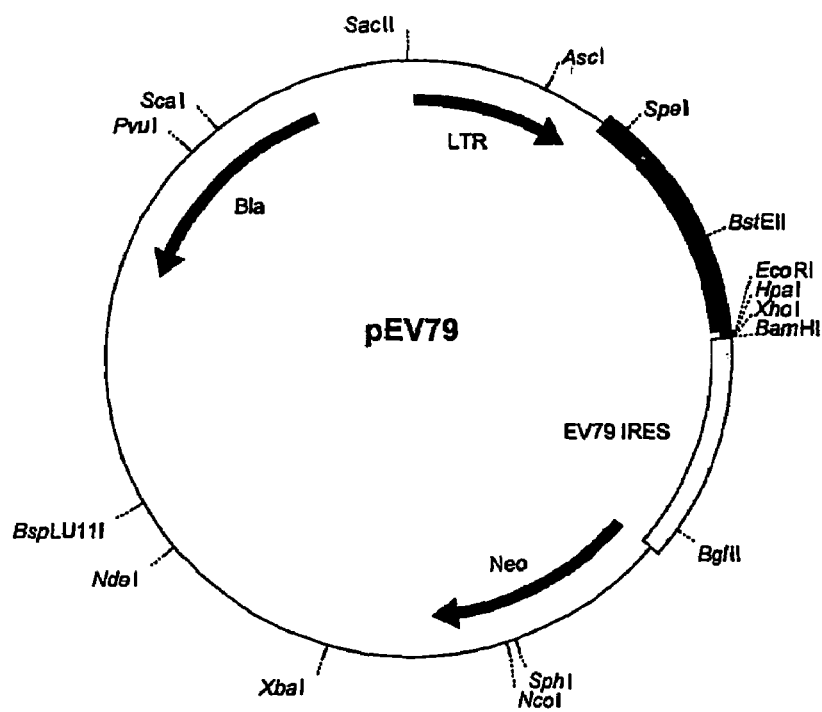

SEQUENCE LISTING

<160> NUMBER OF SEQ ID NOS: 84

<210> SEQ ID NO 1
<211> LENGTH: 19
<212> TYPE: DNA
<213> ORGANISM: Artificial Sequence
<220> FEATURE:
<223> OTHER INFORMATION: Primer PICG2U1

<400> SEQUENCE: 1
ggtacctttg trcgcctgt                                                  19

<210> SEQ ID NO 2
<211> LENGTH: 18
<212> TYPE: DNA
<213> ORGANISM: Artificial Sequence
<220> FEATURE:
<223> OTHER INFORMATION: Primer PICG2D1

<400> SEQUENCE: 2
gacacccaaa gtagtcgg                                                   18

<210> SEQ ID NO 3
<211> LENGTH: 19
<212> TYPE: DNA
<213> ORGANISM: Artificial Sequence
<220> FEATURE:
<223> OTHER INFORMATION: Primer PICG2U1'

<400> SEQUENCE: 3
caagcacttc tgtttcccc                                                  19

<210> SEQ ID NO 4
<211> LENGTH: 18
<212> TYPE: DNA
<213> ORGANISM: Artificial Sequence
<220> FEATURE:
<223> OTHER INFORMATION: Primer PICG2D1'

<400> SEQUENCE: 4
catcgrcctg atctacac                                                   18

<210> SEQ ID NO 5
<211> LENGTH: 17
<212> TYPE: DNA
<213> ORGANISM: Artificial Sequence
<220> FEATURE:
<223> OTHER INFORMATION: Oligonucleotide 07VP4D1

<400> SEQUENCE: 5
agcttccacc accaccc                                                    17

<210> SEQ ID NO 6
<211> LENGTH: 11
<212> TYPE: PRT
<213> ORGANISM: Artificial Sequence

```
<220> FEATURE:
<223> OTHER INFORMATION: Conserved domain within Prima 7 open reading
      frame

<400> SEQUENCE: 6

Gly Tyr Asp Ala Ser Leu Ser Pro Val Trp Phe
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Conserved domain within Prima 7 open reading
      frame

<400> SEQUENCE: 7

Ala Gly Gln Cys Gly Gly Val Val Thr
1               5

<210> SEQ ID NO 8
<211> LENGTH: 7
<212> TYPE: PRT
<213> ORGANISM: Artificial Sequence
<220> FEATURE:
<223> OTHER INFORMATION: Conserved domain within Prima 7 open reading
      frame

<400> SEQUENCE: 8

Asn Glu Lys Phe Arg Asp Ile
1               5

<210> SEQ ID NO 9
<211> LENGTH: 7
<212> TYPE: PRT
<213> ORGANISM: Artificial Sequence
<220> FEATURE:
<223> OTHER INFORMATION: Conserved domain within Prima 7 open reading
      frame

<400> SEQUENCE: 9

Gln Met Val Ser Thr Val Asp
1               5

<210> SEQ ID NO 10
<211> LENGTH: 7
<212> TYPE: PRT
<213> ORGANISM: Artificial Sequence
<220> FEATURE:
<223> OTHER INFORMATION: Conserved domain within Prima 7 open reading
      frame

<400> SEQUENCE: 10

Phe Asp Gly Tyr Lys Gln Gln
1               5

<210> SEQ ID NO 11
<211> LENGTH: 7
<212> TYPE: PRT
<213> ORGANISM: Artificial Sequence
<220> FEATURE:
<223> OTHER INFORMATION: Conserved domain within Prima 7 open reading
      frame

<400> SEQUENCE: 11

Gly Ser Pro Gly Thr Gly Lys
1               5
```

<210> SEQ ID NO 12
<211> LENGTH: 7
<212> TYPE: PRT
<213> ORGANISM: Artificial Sequence
<220> FEATURE:
<223> OTHER INFORMATION: Conserved domain within Prima 7 open reading
      frame

<400> SEQUENCE: 12

Ala Phe Gly Thr Gly Phe Thr
1               5

<210> SEQ ID NO 13
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (27)..(27)
<223> OTHER INFORMATION: "N" on pos. 27 stands for unknown nucleotide
<220> FEATURE:
<221> NAME/KEY: misc_feature
<222> LOCATION: (3)..(33)
<223> OTHER INFORMATION: "R" stands for A or G; "Y" stands for C or T;
      "W" stands for A or T; "S" stands for C or G; "B" stands for C or
      G or T; "M" stands for A or C; and "V" stands for A or C or G

<400> SEQUENCE: 13
garatycayg arwsbatymg vtggacnaar gay                               33

<210> SEQ ID NO 14
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(33)
<223> OTHER INFORMATION: "R" stands for A or G; "Y" stands for C or T;
      "W" stands for A or T; and "M" stands for A or C

<400> SEQUENCE: 14
garatycayg artcwatwmg atggacmaar gay                               33

<210> SEQ ID NO 15
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(27)
<223> OTHER INFORMATION: "N" on pos. 3, 6, 15, 18, 27 stands for unknown
      nucleotide
<220> FEATURE:
<221> NAME/KEY: misc_feature
<222> LOCATION: (3)..(24)
<223> OTHER INFORMATION: "R" stands for A or G; "Y" stands for C or T;
      "S" stands for C or G

<400> SEQUENCE: 15
gcnggncart gyggnggngt sgtsacn                                      27

<210> SEQ ID NO 16
<211> LENGTH: 27
<212> TYPE: DNA

```
<213> ORGANISM: Artificial Sequence
<220> FEATURE:
<223> OTHER INFORMATION: Primer
<220> FEATURE:
<221> NAME/KEY: misc_feature
<222> LOCATION: (3)..(18)
<223> OTHER INFORMATION: "N" on pos. 3 and 18 stands "I" for Inosine
<220> FEATURE:
<221> NAME/KEY: misc_feature
<222> LOCATION: (6)..(27)
<223> OTHER INFORMATION: "R" stands for A or G; "W" stands for A or T;
      "S" stands for C or G; and "M" stands for A or C

<400> SEQUENCE: 16
gcnggrcart gtggwggngt ggtsacm                                27

<210> SEQ ID NO 17
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(21)
<223> OTHER INFORMATION: "R" stands for A or G; "Y" stands for C or T;
      and "M" stands for A or C

<400> SEQUENCE: 17
aaygaraart tymgvgayat y                                     21

<210> SEQ ID NO 18
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(23)
<223> OTHER INFORMATION: "R" stands for A or G; "Y" stands for C or T;
      and "S" stands for C or G

<400> SEQUENCE: 18
aatgaraart tyagrgayat cas                                   23

<210> SEQ ID NO 19
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (9)..(18)
<223> OTHER INFORMATION: "N" on pos. 9, 12, 15, 18 stands for unknown
      nucleotide
<220> FEATURE:
<221> NAME/KEY: misc_feature
<222> LOCATION: (3)..(21)
<223> OTHER INFORMATION: "R" stands for A or G; "Y" stands for C or T;
      and "W" stands for A or T

<400> SEQUENCE: 19
caratggtnw snacngtnga y                                     21

<210> SEQ ID NO 20
<211> LENGTH: 21
<212> TYPE: DNA
<213> ORGANISM: Artificial Sequence
<220> FEATURE:
```

```
<223> OTHER INFORMATION: Primer
<220> FEATURE:
<221> NAME/KEY: misc_feature
<222> LOCATION: (3)..(21)
<223> OTHER INFORMATION: "R" stands for A or G; and "Y" stands for C or
      T

<400> SEQUENCE: 20
caratggtrt cyacygtrga y                                              21

<210> SEQ ID NO 21
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: "N" on pos. 9 stands for unknown nucleotide
<220> FEATURE:
<221> NAME/KEY: misc_feature
<222> LOCATION: (3)..(21)
<223> OTHER INFORMATION: "R" stands for A or G; and "Y" stands for C or
      T

<400> SEQUENCE: 21
ttygayggnt ayaarcarca r                                              21

<210> SEQ ID NO 22
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(21)
<223> OTHER INFORMATION: "R" stands for A or G; and "Y" stands for C or
      T

<400> SEQUENCE: 22
tttgayggrt ayaaacarca r                                              21

<210> SEQ ID NO 23
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(18)
<223> OTHER INFORMATION: "N" on pos. 3, 6, 9, 12, 15, 18 stands for
      unknown nucleotide
<220> FEATURE:
<221> NAME/KEY: misc_feature
<222> LOCATION: (4)..(21)
<223> OTHER INFORMATION: "R" stands for A or G; "W" stands for A or T;
      and "S" stands for C or G

<400> SEQUENCE: 23
ggnwsnccng gnacnggnaa r                                              21

<210> SEQ ID NO 24
<211> LENGTH: 23
<212> TYPE: DNA
<213> ORGANISM: Artificial Sequence
<220> FEATURE:
<223> OTHER INFORMATION: Primer
<220> FEATURE:
```

```
<221> NAME/KEY: misc_feature
<222> LOCATION: (3)..(21)
<223> OTHER INFORMATION: "R" stands for A or G; "Y" stands for C or T;
      "W" stands for A or T; and "M" stands for A or C

<400> SEQUENCE: 24
ggmtcwccag gyactggraa rtc                                               23

<210> SEQ ID NO 25
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(21)
<223> OTHER INFORMATION: "N" on pos. 3, 9, 12, 15, 21 stands for unknown
      nucleotide
<220> FEATURE:
<221> NAME/KEY: misc_feature
<222> LOCATION: (6)..(18)
<223> OTHER INFORMATION: "Y" stands for C or T

<400> SEQUENCE: 25
gcnttyggna cnggnttyac n                                                 21

<210> SEQ ID NO 26
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(15)
<223> OTHER INFORMATION: "N" stands for "I" for Inosine
<220> FEATURE:
<221> NAME/KEY: misc_feature
<222> LOCATION: (6)..(18)
<223> OTHER INFORMATION: "Y" stands for C or T; "R" stands for A or G;
      and "W" stands for A or T

<400> SEQUENCE: 26
gcnttyggra cwggnttyac tga                                               23

<210> SEQ ID NO 27
<211> LENGTH: 24
<212> TYPE: DNA
<213> ORGANISM: Artificial Sequence
<220> FEATURE:
<223> OTHER INFORMATION: Oligonucleotide JZH2R
<220> FEATURE:
<221> NAME/KEY: misc_feature
<222> LOCATION: (19)..(24)
<223> OTHER INFORMATION: "N" on pos. 19-23 stands for unknown nucleotide

<400> SEQUENCE: 27
gctatcatca caatggacnn nnng                                              24

<210> SEQ ID NO 28
<211> LENGTH: 18
<212> TYPE: DNA
<213> ORGANISM: Artificial Sequence
<220> FEATURE:
<223> OTHER INFORMATION: Oligonucleotide JZH1

<400> SEQUENCE: 28
gctatcatca caatggac                                                     18
```

<210> SEQ ID NO 29
<211> LENGTH: 19
<212> TYPE: DNA
<213> ORGANISM: Artificial Sequence
<220> FEATURE:
<223> OTHER INFORMATION: Oligonucleotide 07UVP01

<400> SEQUENCE: 29
ttcactcaac ctgttgtgg                                               19

<210> SEQ ID NO 30
<211> LENGTH: 19
<212> TYPE: DNA
<213> ORGANISM: Artificial Sequence
<220> FEATURE:
<223> OTHER INFORMATION: Oligonucleotide 07UVP02

<400> SEQUENCE: 30
cactcaaatc accatcagc                                               19

<210> SEQ ID NO 31
<211> LENGTH: 20
<212> TYPE: DNA
<213> ORGANISM: Artificial Sequence
<220> FEATURE:
<223> OTHER INFORMATION: Oligonucleotide 07UVP03

<400> SEQUENCE: 31
gccagatcga gtagacacta                                              20

<210> SEQ ID NO 32
<211> LENGTH: 16
<212> TYPE: DNA
<213> ORGANISM: Artificial Sequence
<220> FEATURE:
<223> OTHER INFORMATION: Oligonucleotide 07UVP04

<400> SEQUENCE: 32
atgcaacaca acctgg                                                  16

<210> SEQ ID NO 33
<211> LENGTH: 24
<212> TYPE: DNA
<213> ORGANISM: Artificial Sequence
<220> FEATURE:
<223> OTHER INFORMATION: Oligonucleotide 07UVP05

<400> SEQUENCE: 33
tgaaggagcc actacagcta tacc                                         24

<210> SEQ ID NO 34
<211> LENGTH: 24
<212> TYPE: DNA
<213> ORGANISM: Artificial Sequence
<220> FEATURE:
<223> OTHER INFORMATION: Oligonucleotide 07UVP06

<400> SEQUENCE: 34
actgcagatg atggtgtctc agca                                         24

<210> SEQ ID NO 35
<211> LENGTH: 20
<212> TYPE: DNA
<213> ORGANISM: Artificial Sequence
<220> FEATURE:
<223> OTHER INFORMATION: Primer EV07U1

```
<400> SEQUENCE: 35
cagagatctt gcatacctgt                                                      20

<210> SEQ ID NO 36
<211> LENGTH: 22
<212> TYPE: DNA
<213> ORGANISM: Artificial Sequence
<220> FEATURE:
<223> OTHER INFORMATION: Primer EV07D1

<400> SEQUENCE: 36
agtatccttg gagtattcgg gc                                                   22

<210> SEQ ID NO 37
<211> LENGTH: 22
<212> TYPE: DNA
<213> ORGANISM: Artificial Sequence
<220> FEATURE:
<223> OTHER INFORMATION: Primer EV07U2

<400> SEQUENCE: 37
gaaccagaac atagctgcta gc                                                   22

<210> SEQ ID NO 38
<211> LENGTH: 20
<212> TYPE: DNA
<213> ORGANISM: Artificial Sequence
<220> FEATURE:
<223> OTHER INFORMATION: Primer EV07D2

<400> SEQUENCE: 38
caccatatcc gactgtgatg                                                      20

<210> SEQ ID NO 39
<211> LENGTH: 69
<212> TYPE: PRT
<213> ORGANISM: Artificial Sequence
<220> FEATURE:
<223> OTHER INFORMATION: VP4 capsid protein (PFAM02226), synthetic

<400> SEQUENCE: 39
```

Met Gly Ala Gln Val Ser Thr Gln Lys Thr Gly Ser His Glu Asn Gln
1               5                   10                  15

Asn Ile Ala Ala Ser Gly Ser Thr Ile Asn Tyr Thr Thr Ile Asn Tyr
            20                  25                  30

Tyr Lys Asp Ser Tyr Ala Ala Ser Ala Ala Lys Gln Asp Phe Ser Gln
        35                  40                  45

Asp Pro Ser Lys Phe Thr Gln Pro Val Val Asp Ala Leu Lys Glu Thr
    50                  55                  60

Ala Pro Pro Leu Lys
65

```
<210> SEQ ID NO 40
<211> LENGTH: 255
<212> TYPE: PRT
<213> ORGANISM: Artificial Sequence
<220> FEATURE:
<223> OTHER INFORMATION: VP2 capsid protein (CD00205, PFAM00073),
      synthetic

<400> SEQUENCE: 40
```

Ser Pro Ser Ala Glu Ala Cys Gly Tyr Ser Asp Arg Val Ala Gln Leu
1               5                   10                  15

-continued

```
Thr Leu Gly Asn Ser Thr Ile Thr Thr Gln Glu Ala Ala Asn Ile Thr
            20                  25                  30

Val Gly Tyr Gly Glu Trp Pro Glu Tyr Ser Lys Asp Thr Glu Ala Thr
        35                  40                  45

Ala Val Asp Lys Pro Thr Arg Pro Asp Val Ser Val Asn Arg Phe Tyr
    50                  55                  60

Thr Leu Pro Ala Lys Leu Trp Ala Asn Asn Ser Lys Gly Trp Tyr Trp
65                  70                  75                  80

Lys Phe Pro Asp Val Leu Cys Glu Leu Gly Val Phe Gly Gln Asn Ala
                85                  90                  95

Gln Tyr His Tyr Leu Tyr Arg Ser Gly Phe Cys Ile His Val Gln Cys
            100                 105                 110

Asn Ala Ser Lys Phe His Gln Gly Thr Leu Leu Val Ala Ala Ile Pro
        115                 120                 125

Glu Leu Met Leu Ala Arg Ser Ser Asn Asp Thr Asn Pro Ala Thr Ala
    130                 135                 140

Pro His Pro Pro Tyr Asn Ala Thr Gln Pro Gly Glu Ala Gly Lys Glu
145                 150                 155                 160

Phe Ala Tyr Pro Tyr Ile Leu Asp Ser Gly Ile Pro Leu Ser Gln Ala
                165                 170                 175

Leu Ile Phe Pro His Gln Trp Ile Asn Leu Arg Thr Asn Asn Cys Ala
            180                 185                 190

Thr Ile Val Met Pro Tyr Ile Asn Cys Leu Pro Phe Asp Ser Ala Leu
        195                 200                 205

Asn His Cys Asn Phe Ser Leu Val Val Ile Pro Val Ala Pro Leu Ala
    210                 215                 220

Tyr Asn Glu Gly Ala Thr Thr Ala Ile Pro Ile Thr Val Thr Val Ala
225                 230                 235                 240

Pro Met Cys Ser Glu Phe Ser Gly Leu Arg Gln Ala Val Val Gln
                245                 250                 255

<210> SEQ ID NO 41
<211> LENGTH: 244
<212> TYPE: PRT
<213> ORGANISM: Artificial Sequence
<220> FEATURE:
<223> OTHER INFORMATION: VP3 capsid protein (CD00205, PFAM00073),
      synthetic

<400> SEQUENCE: 41

Gly Leu Pro Ala Glu Leu Lys Pro Gly Thr Asn Gln Phe Leu Thr Thr
1               5                   10                  15

Asp Asp Gly Val Ser Ala Pro Ile Leu Pro Gly Phe His Pro Thr Pro
            20                  25                  30

Glu Met His Ile Pro Gly Glu Val Lys Asn Leu Leu Glu Ile Cys Gln
        35                  40                  45

Val Glu Ser Ile Leu Glu Val Asn Asn Leu Thr Thr Asn Lys Ala Ala
    50                  55                  60

Ser Gln Leu Met Thr Arg Leu Leu Ile Pro Val Glu Ala Gln Thr Ala
65                  70                  75                  80

Val Asp Ala Leu Cys Ala Ala Phe Lys Val Asp Pro Gly Arg Asp Gly
                85                  90                  95

Pro Trp Gln Ser Thr Leu Val Gly Gln Ile Cys Arg Tyr Tyr Thr Gln
            100                 105                 110

Trp Ser Gly Ser Leu Glu Val Thr Phe Met Phe Thr Gly Ser Phe Met
```

-continued

```
        115                 120                 125

Ala Thr Gly Lys Met Leu Ile Ala Tyr Thr Pro Pro Gly Ala Pro Gln
    130                 135                 140
Pro Ala Asn Arg Arg Ile Ala Met Leu Gly Thr His Val Ile Trp Asp
145                 150                 155                 160
Phe Gly Leu Gln Ser Ser Val Thr Leu Val Ile Pro Trp Ile Ser Asn
                165                 170                 175
Thr His Tyr Arg Ala Met Gly Ser Asn Asp Tyr Phe Asp Tyr Tyr Ser
            180                 185                 190

Ala Gly Ile Val Thr Ile Trp Tyr Gln Thr Asn Phe Val Val Pro Ser
        195                 200                 205

Gly Ala Pro Thr Ser Ala Tyr Ile Ile Ala Leu Ala Ala Ala Gln Lys
    210                 215                 220

Asn Phe Thr Leu Arg Leu Pro Lys Asp Thr Gly Asp Ile Ser Gln Thr
225                 230                 235                 240
Ala Ile Leu Gln

<210> SEQ ID NO 42
<211> LENGTH: 295
<212> TYPE: PRT
<213> ORGANISM: Artificial Sequence
<220> FEATURE:
<223> OTHER INFORMATION: VP1 capsid protein (CD00205), synthetic

<400> SEQUENCE: 42

Gly Asp Pro Ile Glu Glu Ala Ile Asn Asn Thr Val Ala Gly Thr Leu
1               5                   10                  15

Asn Arg Ala Leu Gly Ser Ala Ser His Thr Thr Ala Gln Asn Thr Gln
            20                  25                  30

Gln Ser Ser His Gln Ile Gly Thr Gly Glu Val Pro Ala Leu Gln Ala
        35                  40                  45

Ala Glu Thr Gly Ala Thr Ser Asn Thr Ser Asp Glu Asn Met Leu Glu
    50                  55                  60

Thr Arg Cys Val Ile Asn Ser His Ser Val Ala Glu Thr Ser Ile Ser
65                  70                  75                  80

His Phe Phe Ser Arg Ala Gly Leu Val Gly Met Leu Asp Leu Leu Thr
                85                  90                  95

Ser Gly Asp Thr Asp Ile Gly Phe Thr Ser Trp Asp Ile Asp Ile Met
            100                 105                 110

Gly Phe Val Gln Gln Arg Arg Lys Leu Glu Met Phe Thr Tyr Met Arg
        115                 120                 125

Phe Asp Ala Glu Phe Thr Phe Leu Thr Val Gly Ala Thr Gly Ala Ala
    130                 135                 140

Pro Ala Thr Val Ile Gln Tyr Met Tyr Val Pro Pro Gly Ala Pro Lys
145                 150                 155                 160

Pro Thr Gln Arg Asp Ser Phe Glu Trp Gln Thr Ser Thr Asn Pro Ser
                165                 170                 175

Ile Phe Val Lys Val Ser Asp Pro Pro Ala Gln Val Ser Val Pro Phe
            180                 185                 190

Met Ser Pro Ala Ala Ala Tyr Gln Trp Phe Tyr Asp Gly Tyr Pro Thr
        195                 200                 205

Phe Gly Asn His Pro Thr Asn Gln Asp Phe Arg Tyr Gly Ile Cys Pro
    210                 215                 220

Asn Asn Leu Met Gly Thr Phe Cys Val Arg Val Leu Gly Ser Glu Lys
225                 230                 235                 240
```

```
Leu Thr Glu Ala Leu Arg Val Arg Ile Tyr Met Arg Ile Lys His Val
                245                 250                 255

Arg Ala Trp Ile Pro Arg Pro Leu Arg Ser Gln Lys Tyr Leu Leu Lys
            260                 265                 270

Asn Tyr Pro Asn Phe Asp Gly Ala Asp Val Thr Pro Thr Ser Ala Ser
        275                 280                 285

Arg Ala Asn Ile Thr Thr Ala
        290                 295

<210> SEQ ID NO 43
<211> LENGTH: 11
<212> TYPE: PRT
<213> ORGANISM: Artificial Sequence
<220> FEATURE:
<223> OTHER INFORMATION: Conserved sequence motif

<400> SEQUENCE: 43

Pro Ala Leu Thr Ala Val Glu Thr Gly His Thr
1               5                   10

<210> SEQ ID NO 44
<211> LENGTH: 51
<212> TYPE: DNA
<213> ORGANISM: Artificial Sequence
<220> FEATURE:
<223> OTHER INFORMATION: Oligo P2F

<400> SEQUENCE: 44
acaagtttgt acaaaaaagc aggcttctca ccatcagctg aagcatgtgg c          51

<210> SEQ ID NO 45
<211> LENGTH: 50
<212> TYPE: DNA
<213> ORGANISM: Artificial Sequence
<220> FEATURE:
<223> OTHER INFORMATION: Oligo P2R

<400> SEQUENCE: 45
accactttgt acaagaaagc tgggtcttga accacagctt gcctaagacc            50

<210> SEQ ID NO 46
<211> LENGTH: 50
<212> TYPE: DNA
<213> ORGANISM: Artificial Sequence
<220> FEATURE:
<223> OTHER INFORMATION: Oligo P3F

<400> SEQUENCE: 46
acaagtttgt acaaaaaagc aggcttcgga ctaccggcag aattaaaacc            50

<210> SEQ ID NO 47
<211> LENGTH: 48
<212> TYPE: DNA
<213> ORGANISM: Artificial Sequence
<220> FEATURE:
<223> OTHER INFORMATION: Oligo P3R

<400> SEQUENCE: 47
accactttgt acaagaaagc tgggtcttgc aggatggcgg tttgtgag              48

<210> SEQ ID NO 48
<211> LENGTH: 51
<212> TYPE: DNA
<213> ORGANISM: Artificial Sequence
```

```
<220> FEATURE:
<223> OTHER INFORMATION: Oligo P1F

<400> SEQUENCE: 48
acaagtttgt acaaaaaagc aggcttcggt gaccctattg aagaggccat c          51

<210> SEQ ID NO 49
<211> LENGTH: 53
<212> TYPE: DNA
<213> ORGANISM: Artificial Sequence
<220> FEATURE:
<223> OTHER INFORMATION: Oligo P1R

<400> SEQUENCE: 49
accactttgt acaagaaagc tgggtcagct gttgtgatat ggctctaga tgc          53

<210> SEQ ID NO 50
<211> LENGTH: 150
<212> TYPE: PRT
<213> ORGANISM: Artificial Sequence
<220> FEATURE:
<223> OTHER INFORMATION: 2A protease (PFAM00947), synthetic

<400> SEQUENCE: 50
```

Gly Val Phe Gly Gln Gln Ser Gly Ala Val Tyr Val Gly Asn Tyr Lys
1               5                   10                  15

Ile Val Asn Arg His Leu Ala Thr Glu Ala Asp Trp Asn Ser Leu Val
            20                  25                  30

Trp Glu Ser Tyr Asn Arg Asp Leu Leu Val Thr Ser Val Asn Ala Gln
        35                  40                  45

Gly Cys Asp Thr Ile Ala Arg Cys Ser Cys Lys Ala Gly Val Tyr Phe
    50                  55                  60

Cys Lys Ser Met Asn Lys His Tyr Pro Val Ser Phe Gln Gly Pro Gly
65                  70                  75                  80

Ile Val Glu Val Gln Ala Asn Glu Phe Tyr Pro His Arg Tyr Gln Thr
                85                  90                  95

His Val Leu Leu Gly His Gly Thr Ser Ile Pro Gly Asp Cys Gly Gly
            100                 105                 110

Ile Leu Arg Cys Gln His Gly Val Ile Gly Leu Val Thr Met Gly Gly
        115                 120                 125

Asp Gly Leu Val Gly Phe Ala Asp Leu Arg Asp Leu Phe Trp Leu Asp
    130                 135                 140

Asp Glu Ala Met Glu Gln
145                 150

```
<210> SEQ ID NO 51
<211> LENGTH: 99
<212> TYPE: PRT
<213> ORGANISM: Artificial Sequence
<220> FEATURE:
<223> OTHER INFORMATION: 2B (Pico_2B PFAM01552) permeability enhancing
      protein, synthetic

<400> SEQUENCE: 51
```

Gly Val Thr Asp Tyr Ile Lys Gly Leu Gly Asp Ala Phe Gly Thr Gly
1               5                   10                  15

Phe Thr Asp Ser Ile Ser Arg Glu Ile Gln Gln Leu Lys Asn Tyr Leu
            20                  25                  30

Leu Gly Ser Glu Asn Val Val Glu Lys Ile Leu Lys Ala Leu Ile Lys
        35                  40                  45

```
Val Val Ser Ala Leu Val Ile Val Val Arg Ser Asp Tyr Asp Leu Val
 50                  55                  60

Thr Leu Thr Ala Thr Leu Ala Leu Ile Gly Cys His Gly Ser Pro Trp
 65                  70                  75                  80

Ala Trp Leu Lys Ser Lys Val Ser Asn Leu Leu Asp Ile Pro Ile Ala
                 85                  90                  95

Gln Lys Gln

<210> SEQ ID NO 52
<211> LENGTH: 329
<212> TYPE: PRT
<213> ORGANISM: Artificial Sequence
<220> FEATURE:
<223> OTHER INFORMATION: 2C (RNA helicase PFAM00910), synthetic

<400> SEQUENCE: 52

Ser Asp Ser Trp Leu Lys Lys Phe Thr Glu Met Ala Asn Ala Ala Arg
 1               5                  10                  15

Gly Leu Glu Trp Ile Ala Asn Lys Ile Ser Lys Phe Ile Asp Trp Val
                 20                  25                  30

Lys Glu Lys Ile Val Pro Ala Ala Lys Glu Lys Val Glu Phe Leu Ser
             35                  40                  45

Asn Leu Lys Gln Leu Pro Leu Leu Glu Ser Gln Ile Ala Asn Ile Glu
 50                  55                  60

Gln Ser Ala Ala Ser Gln Glu Asp Leu Glu Asn Leu Phe Ser Asn Val
 65                  70                  75                  80

Ala Tyr Leu Ala His Tyr Cys Arg Lys Phe Gln Pro Leu Tyr Ala Ser
                 85                  90                  95

Glu Ala Lys Arg Ile Tyr Ala Met Glu Lys Arg Ile Asn Asn Tyr Met
             100                 105                 110

Gln Phe Lys Ser Lys His Arg Ile Glu Pro Val Cys Leu Ile Ile Arg
         115                 120                 125

Gly Pro Pro Gly Thr Gly Lys Ser Leu Ala Thr Gly Ile Ile Gly Arg
130                 135                 140

Ala Ile Ala Glu Lys Tyr His Ser Ser Val Tyr Ser Leu Pro Pro Asp
145                 150                 155                 160

Pro Asp His Phe Asp Gly Tyr Lys Gln Gln Val Val Thr Val Met Asp
                165                 170                 175

Asp Leu Cys Gln Asn Pro Asp Gly Lys Asp Met Ser Leu Phe Cys Gln
            180                 185                 190

Met Val Ser Thr Val Glu Phe Ile Pro Pro Met Ala Ser Leu Glu Glu
        195                 200                 205

Lys Gly Val Ser Phe Thr Ser Lys Phe Val Ile Ala Ser Thr Asn Ser
    210                 215                 220

Ser Asn Ile Ile Val Pro Thr Val Ser Asp Ser Asp Ala Ile Arg Arg
225                 230                 235                 240

Arg Phe Tyr Met Asp Cys Asp Ile Glu Val Pro Glu Ser Phe Arg Thr
                245                 250                 255

Pro Gln Gly Arg Leu Asp Ala Ala Arg Ala Ala Lys Leu Cys Ser Glu
            260                 265                 270

Asn Asn Thr Ala Asn Phe Lys Lys Cys Ser Pro Leu Val Cys Gly Lys
        275                 280                 285

Ala Ile Gln Leu Arg Asp Arg Lys Ser Gly Val Arg Tyr Gly Leu Asp
    290                 295                 300

Ser Val Val Ser Glu Leu Ile Arg Glu Tyr Asn Asn Arg Ser Ala Val
```

```
                305                 310                 315                 320
Gly Asn Thr Ile Glu Ala Leu Phe Gln
                325

<210> SEQ ID NO 53
<211> LENGTH: 85
<212> TYPE: PRT
<213> ORGANISM: Artificial Sequence
<220> FEATURE:
<223> OTHER INFORMATION: 3A, synthetic

<400> SEQUENCE: 53

Gly Pro Pro Gln Phe Lys Pro Ile Arg Ile Thr Leu Asp Lys Pro Ala
1               5                   10                  15

Pro Asp Ala Ile Ser Asp Leu Leu Ala Ser Val Asp Ser Glu Glu Val
            20                  25                  30

Arg Gln Tyr Cys Arg His Gln Gly Trp Ile Ile Pro Glu Lys Pro Thr
        35                  40                  45

Asn Ile Glu Arg His Val Asn Arg Ala Leu Met Ile Leu Gln Ser Val
    50                  55                  60

Thr Thr Val Val Ala Val Ile Ser Leu Val Tyr Val Ile Tyr Lys Leu
65                  70                  75                  80

Phe Ala Gly Phe Gln
            85

<210> SEQ ID NO 54
<211> LENGTH: 22
<212> TYPE: PRT
<213> ORGANISM: Artificial Sequence
<220> FEATURE:
<223> OTHER INFORMATION: 3B or VPg, synthetic

<400> SEQUENCE: 54

Gly Ala Tyr Ser Gly Met Pro Lys Thr Ala Val Lys Lys Pro Val Leu
1               5                   10                  15

Arg Thr Ala Val Ala Gln
            20

<210> SEQ ID NO 55
<211> LENGTH: 183
<212> TYPE: PRT
<213> ORGANISM: Artificial Sequence
<220> FEATURE:
<223> OTHER INFORMATION: 3C protease (PFAM00548), synthetic

<400> SEQUENCE: 55

Gly Pro Gly Leu Asp Phe Ala Leu Ser Leu Leu Lys Lys Asn Ile Arg
1               5                   10                  15

Lys Cys Gln Thr Asp Gln Gly His Phe Thr Leu Leu Gly Ile Arg Asp
            20                  25                  30

Arg Leu Ala Val Leu Pro Arg His Ala Ser Pro Gly Asp Ser Ile Trp
        35                  40                  45

Ile Glu His Lys Gln Ile Lys Ile Leu Asp Ala Val Glu Leu Val Asp
    50                  55                  60

Glu Gln Gln Val Asn Leu Glu Leu Thr Leu Ile Thr Leu Asp Thr Asn
65                  70                  75                  80

Glu Lys Phe Arg Asp Ile Thr Lys Phe Ile Pro Glu Gln Ile Glu Gly
            85                  90                  95

Thr Ala Asp Ala Thr Leu Val Ile Asn Thr Glu Ala Met Pro Ser Met
            100                 105                 110
```

```
Phe Val Pro Val Gly Asp Val Gln Gln Tyr Gly Phe Leu Asn Leu Ser
            115                 120                 125
Gly Lys Pro Thr His Arg Thr Met Met Tyr Asn Phe Pro Thr Lys Ala
        130                 135                 140
Gly Gln Cys Gly Gly Val Val Thr Ser Val Gly Arg Ile Val Gly Ile
145                 150                 155                 160
His Ile Gly Gly Asn Gly Arg Gln Gly Phe Cys Ala Ala Leu Lys Arg
                165                 170                 175
Ser Tyr Phe Ala Ser Glu Gln
            180

<210> SEQ ID NO 56
<211> LENGTH: 462
<212> TYPE: PRT
<213> ORGANISM: Artificial Sequence
<220> FEATURE:
<223> OTHER INFORMATION: 3D or POL RNA dependant RNA Polymerase
      (PFAM00680), synthetic

<400> SEQUENCE: 56

Gly Glu Ile Gln Trp Met Lys Ser Asn Lys Thr Gly Asn Phe Asn
1               5                   10                  15
Ile Asn Gly Pro Thr Lys Thr Lys Leu Glu Pro Ser Val Phe His Asp
            20                  25                  30
Val Phe Glu Gly Val Lys Glu Pro Ala Val Leu His Ser Lys Asp Lys
        35                  40                  45
Arg Leu Glu Val Asp Phe Glu Thr Ala Leu Phe Ser Lys Tyr Ile Gly
    50                  55                  60
Asn Lys Met His Glu Pro Asp Glu Tyr Met Ile Gln Ala Ala Asn His
65                  70                  75                  80
Tyr Ala Asp Gln Leu Lys Gln Leu Asp Ile Asp Thr Ser Lys Met Ser
                85                  90                  95
Met Glu Asp Ala Cys Tyr Gly Thr Glu Phe Leu Glu Gly Ile Asp Leu
            100                 105                 110
Ala Thr Ser Ala Gly Tyr Pro Tyr Asn Ala Leu Gly Ile Lys Lys Lys
        115                 120                 125
Asp Ile Leu Asn Pro Gln Thr Arg Asp Val Thr Lys Met Lys Met Tyr
    130                 135                 140
Leu Asp Lys Tyr Gly Ile Asp Leu Pro Tyr Ser Thr Tyr Val Lys Asp
145                 150                 155                 160
Glu Leu Arg Ala Lys Asp Lys Ile Lys Lys Gly Lys Ser Arg Leu Ile
                165                 170                 175
Glu Ala Ser Ser Ile Asn Asp Ser Val Tyr Leu Arg Met Cys Phe Gly
            180                 185                 190
His Leu Tyr Glu Lys Phe His Ala Asn Pro Gly Thr Ile Thr Gly Ser
        195                 200                 205
Ala Val Gly Cys Asn Pro Asp Thr Phe Trp Ser Lys Ile Pro Ile Met
    210                 215                 220
Leu Pro Gly Ser Leu Phe Ala Phe Asp Tyr Thr Gly Tyr Asp Ala Ser
225                 230                 235                 240
Leu Ser Pro Ala Trp Phe Arg Ala Leu Glu Ile Val Leu Lys Arg Leu
                245                 250                 255
Gly Tyr Asp Gln Asp Ala Ile Ser Leu Ile Glu Gly Ile Asn His Ser
            260                 265                 270
His His Ile Tyr Arg Asn Gln Thr Tyr Cys Val Met Gly Gly Met Pro
```

```
                275                 280                 285
Ser Gly Cys Ser Gly Thr Ser Ile Phe Asn Ser Met Ile Asn Asn Ile
    290                 295                 300

Ile Ile Arg Thr Leu Leu Ile Arg Thr Phe Lys Gly Ile Asp Leu Asp
305                 310                 315                 320

Glu Leu Asn Met Ile Ala Tyr Gly Asp Asp Val Leu Ala Ser Tyr Pro
                325                 330                 335

Phe Pro Ile Asp Cys Ala Glu Leu Ala Lys Thr Gly Leu Glu Tyr Gly
            340                 345                 350

Leu Val Met Thr Pro Ala Asp Lys Ser Thr Cys Phe Asn Glu Val Asn
        355                 360                 365

Trp Glu Asn Ala Thr Phe Leu Lys Arg Gly Phe Lys Pro Asp Glu Gln
    370                 375                 380

Tyr Pro Phe Leu Ile His Pro Thr Met Pro Met Lys Glu Ile His Glu
385                 390                 395                 400

Ser Ile Arg Trp Thr Lys Asp Pro Arg Asn Thr Gln Asp His Val Arg
                405                 410                 415

Ser Leu Cys Leu Leu Ala Trp His Asn Gly Arg Glu Thr Tyr Glu Glu
            420                 425                 430

Phe Val Asp Lys Ile Arg Thr Val Pro Ile Gly Lys Val Leu Ala Leu
        435                 440                 445

Pro Asn Tyr Asp Asn Leu Arg Arg Asn Trp Leu Glu Leu Phe
    450                 455                 460

<210> SEQ ID NO 57
<211> LENGTH: 40
<212> TYPE: DNA
<213> ORGANISM: Artificial Sequence
<220> FEATURE:
<223> OTHER INFORMATION: Oligo PLXRN1, synthetic

<400> SEQUENCE: 57
gggataattc ctgcagccac catgggatcg gccattgaac                           40

<210> SEQ ID NO 58
<211> LENGTH: 40
<212> TYPE: DNA
<213> ORGANISM: Artificial Sequence
<220> FEATURE:
<223> OTHER INFORMATION: Oligo PLXRN2

<400> SEQUENCE: 58
gttcaatggc cgatcccatg gtggctgcag gaattatccc                           40

<210> SEQ ID NO 59
<211> LENGTH: 29
<212> TYPE: DNA
<213> ORGANISM: Artificial Sequence
<220> FEATURE:
<223> OTHER INFORMATION: Oligo IRES5

<400> SEQUENCE: 59
ggggatcctt taaaacagct ctagggttg                                       29

<210> SEQ ID NO 60
<211> LENGTH: 33
<212> TYPE: DNA
<213> ORGANISM: Artificial Sequence
<220> FEATURE:
<223> OTHER INFORMATION: Oligo IRES3
```

-continued

```
<400> SEQUENCE: 60
ccacatgttc tctttctact attcaactgt atg                                    33

<210> SEQ ID NO 61
<211> LENGTH: 682
<212> TYPE: DNA
<213> ORGANISM: Artificial Sequence
<220> FEATURE:
<223> OTHER INFORMATION: 5' UTR sequence of Prima 7, synthetic

<400> SEQUENCE: 61
ggtacctttg tacgcctgtt ttatatccct tcccccatgt aacttagaag atgttaaaca       60
aagttcaata ggagggggta caaaccagtg ccaccacgaa caaacacttc tgtttccccg      120
gtgaagctac atagactgtt cccacggttg aaagtggcag atccgttatc cgctttggta      180
cttcgagaaa cctagtacca ccttggaatc ttcgatgcgt tgcgctcagc actcaacccc      240
agagtgtagc ttaggtcgat gagtctggac gatcctcact ggcgacagtg gtccaggctg      300
cgttggcggc ctacctgtgg cgaaagccac aggacgctag ttgtgaacaa ggtgtgaaga      360
gtctattgag ctaccaaaga gtcctccggc ccctgaatgc ggctaatccc aaccacggag      420
caagtgccca caaaccagtg ggtggcttgt cgtaatgcgt aagtctgtgg cggaaccgac      480
tactttgggt gtccgtgttt cctttcattt ttatcatggc tgcttatggt gacaatctaa      540
gattgttatc atatagctat tgaattggcc atccggtgac taacagagat cttgcatacc      600
tgtttgttgg ttttactaaa ctagatataa ttacatttaa aactcttctt tatatcatac      660
agttgaatag tagaaagaga aa                                               682

<210> SEQ ID NO 62
<211> LENGTH: 1066
<212> TYPE: DNA
<213> ORGANISM: Artificial Sequence
<220> FEATURE:
<223> OTHER INFORMATION: Open reading frame sequence of Prima 7,
      synthetic

<400> SEQUENCE: 62
atgggagctc aagtttcaac ccaaaagact ggatctcatg agaaccagaa catagctgct       60
agcggctcca ctataaatta cacaaccatc aactactaca aggattccta tgccgcttca      120
gccgcaaagc agggtttctc ccaagacccc tccaaattca ctcaacctgt tgtggatgct      180
ctcaaagaaa cggctccacc actcaaatca ccatcagctg aagcatgtgg ctatagtgat      240
agggttgccc agctaacact gggtaattcc actatcacaa ctcaggaggc tgccaacatc      300
acagtcggat atggtgagtg gcccgaatat tccaaggata ctgaggccac tgcagtggac      360
aagcctacta gaccagatgt gtcagtcaat aggttctaca cactcccggc aaaattatgg      420
gccaacaact ctaaaggatg gtggtggaag tttccagatg ttctctgcga gctgggagtg      480
tttggtcaaa acgcacagta ccattacttg tataggtccg ggttctgcat acatgtccaa      540
tgtaatgcta gtaagtttca tcaaggcaca ctcttggtgg ctgctatacc agaattaatg      600
cttgccagat cgagtaatga cactaaccca gccactgccc cccacccacc atataatgca      660
acacaacctg gggaggcagg caaggaattt gcttacccct acattcttga ttccggcatc      720
ccactgtctc aagctctgat cttccctcat cagtggatca acttgcgcac taacaactgt      780
gctaccatag ttatgcccta tatcaactgc ttgccctttg actcagccct gaaccactgc      840 aactttttcct tggtggtcat accagttgca ccactcgctt acaatgaagg agccactaca      900
```

-continued

```
gctataccca ttactgtaac tgttgcccca atgtgctcgg aattcagtgg tcttaggcaa    960
gctgtggttc aaggactacc ggcagaatta aaacctggga ctaatcaatt tttaactaca   1020
gatgatggtg tctcagcacc aattttacct ggtttccacc caaccg                  1066

<210> SEQ ID NO 63
<211> LENGTH: 355
<212> TYPE: PRT
<213> ORGANISM: Artificial Sequence
<220> FEATURE:
<223> OTHER INFORMATION: Amino acid sequence of VP4 and VP2 region
      translated from Prima 7, synthetic

<400> SEQUENCE: 63

Met Gly Ala Gln Val Ser Thr Gln Lys Thr Gly Ser His Glu Asn Gln
1               5                   10                  15

Asn Ile Ala Ala Ser Gly Ser Thr Ile Asn Tyr Thr Thr Ile Asn Tyr
            20                  25                  30

Tyr Lys Asp Ser Tyr Ala Ala Ser Ala Ala Lys Gln Gly Phe Ser Gln
        35                  40                  45

Asp Pro Ser Lys Phe Thr Gln Pro Val Val Asp Ala Leu Lys Glu Thr
    50                  55                  60

Ala Pro Pro Leu Lys Ser Pro Ser Ala Glu Ala Cys Gly Tyr Ser Asp
65                  70                  75                  80

Arg Val Ala Gln Leu Thr Leu Gly Asn Ser Thr Ile Thr Thr Gln Glu
                85                  90                  95

Ala Ala Asn Ile Thr Val Gly Tyr Gly Glu Trp Pro Glu Tyr Ser Lys
            100                 105                 110

Asp Thr Glu Ala Thr Ala Val Asp Lys Pro Thr Arg Pro Asp Val Ser
        115                 120                 125

Val Asn Arg Phe Tyr Thr Leu Pro Ala Lys Leu Trp Ala Asn Asn Ser
    130                 135                 140

Lys Gly Trp Tyr Trp Lys Phe Pro Asp Val Leu Cys Glu Leu Gly Val
145                 150                 155                 160

Phe Gly Gln Asn Ala Gln Tyr His Tyr Leu Tyr Arg Ser Gly Phe Cys
                165                 170                 175

Ile His Val Gln Cys Asn Ala Ser Lys Phe His Gln Gly Thr Leu Leu
            180                 185                 190

Val Ala Ala Ile Pro Glu Leu Met Leu Ala Arg Ser Ser Asn Asp Thr
        195                 200                 205

Asn Pro Ala Thr Ala Pro His Pro Pro Tyr Asn Ala Thr Gln Pro Gly
    210                 215                 220

Glu Ala Gly Lys Glu Phe Ala Tyr Pro Tyr Ile Leu Asp Ser Gly Ile
225                 230                 235                 240

Pro Leu Ser Gln Ala Leu Ile Phe Pro His Gln Trp Ile Asn Leu Arg
                245                 250                 255

Thr Asn Asn Cys Ala Thr Ile Val Met Pro Tyr Ile Asn Cys Leu Pro
            260                 265                 270

Phe Asp Ser Ala Leu Asn His Cys Asn Phe Ser Leu Val Val Ile Pro
        275                 280                 285

Val Ala Pro Leu Ala Tyr Asn Glu Gly Ala Thr Thr Ala Ile Pro Ile
    290                 295                 300

Thr Val Thr Val Ala Pro Met Cys Ser Glu Phe Ser Gly Leu Arg Gln
305                 310                 315                 320

Ala Val Val Gln Gly Leu Pro Ala Glu Leu Lys Pro Gly Thr Asn Gln
                325                 330                 335
```

Phe Leu Thr Thr Asp Asp Gly Val Ser Ala Pro Ile Leu Gly Pro Phe
            340                 345                 350

His Pro Thr
        355

<210> SEQ ID NO 64
<211> LENGTH: 548
<212> TYPE: DNA
<213> ORGANISM: Artificial Sequence
<220> FEATURE:
<223> OTHER INFORMATION: PCR product of strain 07-1787

<400> SEQUENCE: 64 cctttatt ttatcatggc tgcttatggt gacaatctaa gattgttatc atatagctat     60
tgaattggcc atccggtgac taacagagat cttgcatacc tgtttgttgg ttttactaaa    120
ctagatataa ttacatttaa aactcttctt tatatcatac agttgaatag tagaaagaga    180
aaatgggagc tcaagtttca acccaaaaga ctggatctca tgagaaccag aacatagctg    240
ctagcggctc cactataaat tacacaacca tcaactacta caaggattcc tatgccgctt    300
cagccgcaaa gcagggtttc tcccaagacc cctccaaatt cactcaacct gttgtggatg    360
ctctcaaaga aacggctcca ccactcaaat caccatcagc tgaagcatgt ggctatagtg    420
atagggttgc ccagctaaca ctgggtaatt ccactatcac aactcaggag ctgccaaca    480 tcacagtcgg atatggtgag tggcccgaat attccaagga tactgaggcc actgcagtgg    540
acaagcct                                                             548

<210> SEQ ID NO 65
<211> LENGTH: 240
<212> TYPE: DNA
<213> ORGANISM: Artificial Sequence
<220> FEATURE:
<223> OTHER INFORMATION: PCR product of strain F26ko103

<400> SEQUENCE: 65
tgctagcggc tccactataa attacacaac catcaactat acaaggatt cctatgccgc     60 ttcagccgca aagcaggatt tctcccaaga cccctccaaa ttcactcaac ctgttgtaga    120
tgctctcaaa gaaacggctc caccactcaa atcaccatca gctgaagcat gtggctatag    180
tgatagggtt gcccagctaa cactgggtaa ttccactatt acaactcagg aggctgccaa    240

<210> SEQ ID NO 66
<211> LENGTH: 233
<212> TYPE: DNA
<213> ORGANISM: Artificial Sequence
<220> FEATURE:
<223> OTHER INFORMATION: PCR product of strain F26ko106

<400> SEQUENCE: 66
ggctccacta taaattacac aaccatcaac tattacaagg attcctatgc cgcttcagcc     60
gcaaagcagg atttctccca agaccccctcc aaattcactc aacctgttgt agatgctctc    120
aaagaaacgg ctccaccact caaatcacca tcagctgaag catgtggcta tagtgatagg    180
gttgcccagc taacactggg taattccact atcacaactc aggtggctgc cga            233

<210> SEQ ID NO 67
<211> LENGTH: 240
<212> TYPE: DNA
<213> ORGANISM: Artificial Sequence
<220> FEATURE:

<223> OTHER INFORMATION: PCR product of strain F26kol10

<400> SEQUENCE: 67

```
tgctagcggc tccactataa attacacaac catcaactat tacaaggatt cctatgccgc    60
ttcagccgca aagcaggatt tctcccaaga cccctccaaa ttcactcaac ctgttgtaga   120
tgctctcaga gaaacggctc caccactcaa atcaccatca gctgaagcat gtggctatag   180
tgatagggtt gcccagctaa cactgggtaa ttccactatc acaactcagg aggctgccaa   240
```

<210> SEQ ID NO 68
<211> LENGTH: 243
<212> TYPE: DNA
<213> ORGANISM: Artificial Sequence
<220> FEATURE:
<223> OTHER INFORMATION: PCR product of strain F27kol20

<400> SEQUENCE: 68

```
tgctagccgg ctccactata aattacacaa ccatcaacta ttacaaggat tcctatgccg    60
cttcagccgc aaagcaggat ttctcccaag acccctccaa attcactcaa cctgttgtgg   120
atgctctcaa agaaacggct ccaccactca aatcaccatc agctgaagca tgtggctata   180
ggtgacaagg gttgcccagc taacactggg taattccact atcacaactc aggaggctgc   240
caa                                                                 243
```

<210> SEQ ID NO 69
<211> LENGTH: 234
<212> TYPE: DNA
<213> ORGANISM: Artificial Sequence
<220> FEATURE:
<223> OTHER INFORMATION: PCR product of strain F27kol21

<400> SEQUENCE: 69

```
cggctccact ataaattaca caaccatcaa ctactacaag gattcctatg ccgcttcagc    60
cgcaaggcag gatttctccc aagacccttc caaattcact caacctgttg tagatgctct   120
caaagaaact gctccaccac tcaaatcacc atcagctgaa gcatgtggct atagtgatag   180
ggttgcccag ctaacactgg gtaattccac tatcacaact caggaggctg ccaa          234
```

<210> SEQ ID NO 70
<211> LENGTH: 233
<212> TYPE: DNA
<213> ORGANISM: Artificial Sequence
<220> FEATURE:
<223> OTHER INFORMATION: PCR product of strain F35kol32

<400> SEQUENCE: 70

```
ggctctacta taaattacac aaccatcaac tactacaagg attcctatgc cgcttcagcc    60
gcaaagcagg atttctccca agacccctcc aaattcactc aacctgttgt agatgctctc   120
aaagaaacgg ctccaccact caaatcacca tcagctgaag catgtggcta tagtgacagg   180
gttgcccagc taacactggg taattccact atcacaactc aggaggctgc caa           233
```

<210> SEQ ID NO 71
<211> LENGTH: 240
<212> TYPE: DNA
<213> ORGANISM: Artificial Sequence
<220> FEATURE:
<223> OTHER INFORMATION: PCR product of strain F35kol36

<400> SEQUENCE: 71

```
tgctagcggc tctactataa attacacaac catcaactac tacaaggatt cctatgccgc    60
```

-continued

```
ttcagccgca aagcaggatt tctcccaaga cccctccaaa ttcactcaac ctgttgtaga    120
tgctctcaaa gaaacggctc caccactcaa atcaccatca gctgaagcat gtggctatag    180
tgacagggtt gcccagctaa cactgggtaa ttccactatc acaactcagg aggctgccaa    240

<210> SEQ ID NO 72
<211> LENGTH: 50
<212> TYPE: DNA
<213> ORGANISM: Artificial Sequence
<220> FEATURE:
<223> OTHER INFORMATION: Recombination site with Coxsackie part and EV79
      derived part

<400> SEQUENCE: 72
actgcaatgc tgggaaccca tgtgatatgg gattttggtt tacaatcatc                50

<210> SEQ ID NO 73
<211> LENGTH: 50
<212> TYPE: DNA
<213> ORGANISM: Artificial Sequence
<220> FEATURE:
<223> OTHER INFORMATION: Crossover site with EV71 and EV79 sequences

<400> SEQUENCE: 73
tcttatggtt agatgaagaa gccatggaac agggggtcac ggattacatc                50

<210> SEQ ID NO 74
<211> LENGTH: 340
<212> TYPE: DNA
<213> ORGANISM: Artificial Sequence
<220> FEATURE:
<223> OTHER INFORMATION: 5' UTR sequence of human enterovirus
      D00538CXA21

<400> SEQUENCE: 74
cactccccac cggcgacggt ggcccaggct gcgttggcgg cctacccatg gctgatgccg     60
tgggacgcta gttgtgaaca aggtgtgaag agcctattga gctactcaag agtcctccgg    120
cccctgaatg cggctaatcc taaccacgga gcaatcgctc acgacccagt gagtaggttg    180
tcgtaatgcg taagtctgtg gcggaaccga ctactttggg tgtccgtgtt tccctttata    240
ttcatactgg ctgcttatgg tgacaattta cgaattgtta ccatatagct attggattgg    300
ccacccagtg ctgtgcaata tatttgagtg cttctttcat                          340

<210> SEQ ID NO 75
<211> LENGTH: 339
<212> TYPE: DNA
<213> ORGANISM: Artificial Sequence
<220> FEATURE:
<223> OTHER INFORMATION: 5' UTR sequence of human enterovirus D00820EV70

<400> SEQUENCE: 75
caccccacac cggcgacgtg gtccaggctg cgttggcggc ctacccatgg ctagcaccat     60
gggacgctag ttgtgaacaa ggtgcgaaga gcctattgag ctacctgaga gtcctccggc    120
ccctgaatgc ggctaatccc aaccacggag caaatgctca caatccagtg agtggtttgt    180
cgtaatgcgc aagtctgtgg cggaaccgac tactttgggt gtccgtgttt ccttttattt    240
ttattatggc tgcttatggt gacaatctga gattgttatc atatagctat tggattagcc    300
atccggtgat atcttgaaat tttgccataa ctttttcac                           339

<210> SEQ ID NO 76
```

```
<210> SEQ ID NO 76
<211> LENGTH: 340
<212> TYPE: DNA
<213> ORGANISM: Artificial Sequence
<220> FEATURE:
<223> OTHER INFORMATION: 5' UTR sequence of human enterovirus D00625PV2

<400> SEQUENCE: 76
cgttcctcac cggcgacggt ggtccaggct gcgttggcgg cctacctgtg gcccaaagcc      60
acaggacgct agttgtgaac aaggtgtgaa gagcctattg agctacctga gagtcctccg     120
gcccctgaat gcggctaatc ctaaccacgg agcaggcagt ggcaatccag cgaccagcct     180
gtcgtaacgc gcaagttcgt ggcggaaccg actactttgg gtgtccgtgt ttccttttat     240
ttttacaatg gctgcttatg gtgacaatta ttgatagtta tcataaagca aattggattg     300
gccatccggt gagaatttga ttattaaatt actctcttgt                           340

<210> SEQ ID NO 77
<211> LENGTH: 340
<212> TYPE: DNA
<213> ORGANISM: Artificial Sequence
<220> FEATURE:
<223> OTHER INFORMATION: 5' UTR sequence of human enterovirus
      AJ293918PV3

<400> SEQUENCE: 77
cacgccccac cggcgacggt ggcccaggct gcgttggcgg cctacccatg gctatcacca      60
tgggacgcta gttgtgaaca aggtgtgaag agcctattga gctacccaag agtcctccgg     120 ccccctgaatg cggctaatcc taaccacgga gcaagtgtcc tcaacccagg ggatggcttg    180
tcgtaacgcg aaagtctgtg gcggaaccga ctactttggg tgtccgtgtt ccttttatt     240 tttatgtatg gctgcttatg gtgacaatca aggttgtta ccataaagca atttggattg      300
gccatccggt gagaatcaaa catattatct acctgtttgt                           340

<210> SEQ ID NO 78
<211> LENGTH: 340
<212> TYPE: DNA
<213> ORGANISM: Artificial Sequence
<220> FEATURE:
<223> OTHER INFORMATION: 5' UTR sequence of human enterovirus
      U05876CXA16

<400> SEQUENCE: 78
cgatccccac gggcgaccgt ggcagtggct gcgttggcgg cctgcctgtg gggtaaccca      60
caggacgctc taatatggac atggtgcaaa gagtctattg agctagttag tagtcctccg     120
gcccctgaat gcggctaatc ctaactgcgg agcacatacc ctcgacccag ggggcagtgt     180
gtcgtaacgg gcaactctgc agcggaaccg actactttgg gtgtccgtgt ttccttttat     240
tcttatactg gctgcttatg gtgacaattg aaagattgtt accatatagc tattggattg     300
gccatccggt gtgcaacaga gctattattt acctatttgt                           340

<210> SEQ ID NO 79
<211> LENGTH: 340
<212> TYPE: DNA
<213> ORGANISM: Artificial Sequence
<220> FEATURE:
<223> OTHER INFORMATION: 5' UTR sequence of human enterovirus U22521EN71

<400> SEQUENCE: 79
cattccccac gggcgaccgt ggcggtggct gcgttggcgg cctgcctatg gggtaaccca      60
taggacgctc taatacggac atggcgtgaa gagtctattg agctagttag tagtcctccg     120
```

```
gcccctgaat gcggctaatc ctaactgcgg agcacatacc cttaatccaa agggcagtgt    180
gtcgtaacgg gcaactctgc agcggaaccg actactttgg gtgtccgtgt ttcttttat    240 tcttgtattg gctgcttatg gtgacaatta aagaattgtt accatatagc tattggattg    300
gccatccagt gtcaaacaga gctattgtat atctctttgt                         340

<210> SEQ ID NO 80
<211> LENGTH: 340
<212> TYPE: DNA
<213> ORGANISM: Artificial Sequence
<220> FEATURE:
<223> OTHER INFORMATION: 5' UTR sequence of human enterovirus
      AY056702PV1

<400> SEQUENCE: 80
cgttccccac cggtgacggt ggcccaggct gcgttggcgg cctacccatg gctcacgcca    60
tgggacgcta gttgtgaaca aggtgtgaag agcctattga gctacctaag agtcctccgg    120
cccctgaatg cggctaatcc taaccacgga gcaagtgcct tcagcccaga aggtagcttg    180
tcgtaacgcg caaggtctgt ggcggaaccg actactttgg gtgtcccgtg tttccccta    240 ttttcattgt ggctgcttgc gggactataa ttgattgcca tcataaagcg atttggattg    300
gccatccgga gaaagttaaa cacgttgttt atttattcgt                         340

<210> SEQ ID NO 81
<211> LENGTH: 338
<212> TYPE: DNA
<213> ORGANISM: Artificial Sequence
<220> FEATURE:
<223> OTHER INFORMATION: 5' UTR sequence of human EV79

<400> SEQUENCE: 81
cgatcctcac tggcgacagt ggtccaggct gcgttggcgg cctacctgtg gcgaaagcca    60
caggacgcta gttgtgaaca aggtgtgaag agtctattga gctaccaaag agtcctccgg    120
cccctgaatg cggctaatcc caaccacgga gcaagtgccc acaaaccagt gggtggcttg    180
tcgtaatgcg taagtctgtg gcggaaccga ctactttggg tgtccgtgtt tccttttatt    240
tttatcatgg ctgcttatgg tgacaatcta agattgttat catatagcta ttggattggc    300
catccggtga ctaacagaga tcttgtatac ctgtttgt                           338

<210> SEQ ID NO 82
<211> LENGTH: 7438
<212> TYPE: DNA
<213> ORGANISM: Artificial Sequence
<220> FEATURE:
<223> OTHER INFORMATION: Prima 7 (EV79) nucleotide sequence, synthetic

<400> SEQUENCE: 82
tttaaaacag ctctagggtt gttcccaccc tagaggccca agtggcggct agcactctgg    60
tattacggta cctttgtgcg cctgttttat atcccttccc ccatgtaact tagaagatat    120
taaacaaagt tcaataggag ggggtacaaa ccagtgccac cacgaacaaa cacttctgtt    180
tccccggtga agctacatag actgttccca cggttgaaag tggcagatcc gttatccgct    240
ttggtacttc gagaaaccta gtaccacctt ggaatcttcg atgcgttgcg ctcagcactc    300
aaccccagag tgtagcttag gtcgatgagt ctggacgatc ctcactggcg acagtggtcc    360
aggctgcgtt ggcggcctac ctgtggcgaa agccacagga cgctagttgt gaacaaggtg    420
tgaagagtct attgagctac caaagagtcc tccggcccct gaatgcggct aatcccaacc    480
```

```
acggagcaag tgcccacaaa ccagtgggtg gcttgtcgta atgcgtaagt ctgtggcgga      540
accgactact ttgggtgtcc gtgtttcctt ttatttttat catggctgct tatggtgaca      600
atctaagatt gttatcatat agctattgga ttggccatcc ggtgactaac agagatcttg      660
catacctgtt tgttggtttt actaaactag atatagttac atttaaaact cttctttata      720
tcatacagtt gaatagtaga aagagaaaat gggagctcaa gtttcaaccc aaaagactgg      780
atctcatgag aaccagaaca tagctgctag cggctccact ataaattaca caaccatcaa      840
ctactacaag gattcctatg ccgcttcagc cgcaaagcag gatttctccc aagacccctc      900
caaattcact caacctgttg tggatgctct caaagaaacg gctccaccac tcaaatcacc      960
atcagctgaa gcatgtggct atagtgtag ggttgcccag ctaacactgg gtaattccac      1020
tatcacaact caggaggctg ccaacatcac agtcggatat ggtgagtggc ccgaatattc      1080
caaggatact gaggccactg cagtggacaa gcctactaga ccagatgtgt cagtcaatag      1140
gttctacaca ctcccggcaa aattatgggc caacaactct aaaggatggt attggaagtt      1200
tccagatgtt ctctgcgagc tgggagtgtt tggtcaaaac gcacagtacc attacttgta      1260
taggtccggg ttctgcatac atgtccaatg taatgctagt aagtttcatc aaggcacact      1320
cttggtggct gctataccag aattaatgct tgccagatcg agtaatgaca ctaacccagc      1380
cactgccccc cacccaccat ataatgcaac acaacctggg gaggcaggca aggaatttgc      1440 ttaccccctac attcttgact ccggcatccc actgtctcaa gctctgatct tccctcatca      1500
gtggatcaac ttgcgcacta caactgtgc taccatagtt atgccctata tcaactgctt      1560 gcccttttgac tcagccctga accactgcaa cttttccttg gtggtcatac cagttgcacc      1620
actcgcttac aatgaaggag ccactacagc tatacccatt actgtaactg ttgccccaat      1680
gtgctcggaa ttcagtggtc ttaggcaagc tgtggttcaa ggactaccgg cagaattaaa      1740
acctgggact aatcaatttt taactacaga tgatggtgtc tcagcaccaa ttttacctgg      1800
tttccaccca accccagaga tgcacatccc aggtgaagtg aagaacctct tagaaatttg      1860
ccaagtggag tctattctcg aggtcaacaa ccttaccacc aataaagcag ctagccaact      1920
catgacacgc ctgttgatac cagtggaagc gcaaactgca gtggatgcac tctgtgcagc      1980
tttcaaagtt gatcctgggc gcgatgggcc ttggcaatct acattagtgg gtcagatatg      2040
cagatactac acccaatggt caggatccct cgaagtgaca ttcatgttca ctggtagttt      2100
tatggcaacg gggaaaatgc tcattgccta caccccacca ggtgcgccgc aacccgctaa      2160
cagaagaatt gcaatgttag ggacacatgt aatctgggat tttggtttac aatcatctgt      2220
caccttggtc atcccctgga tcagcaacac gcattacaga gccatgggta gtaatgatta      2280
ttttgactac tactctgcag gtattgtaac aatttggtat cagaccaact tgtggtgcc      2340 atcaggagcc ccaacatcag cttacattat cgcccttgct gctgctcaga gaactttac      2400 attgaggttg cccaaggaca ctggcgatat ctcacaaacc gccatcctgc aaggtgaccc      2460
tattgaagag gccatcaaca acacagtcgc tggaacactg aatcgagcac tgggaagtgc      2520
atcacacacc acagcccaaa acacacagca aagtagccat cagattggaa caggagaagt      2580
ccccgccctg caagcagcag agactggggc tacatccaac acttcagatg agaacatgtt      2640
ggaaacccgt tgtgtgatca actcccatag tgtggctgag actagtatct cgcatttctt      2700
ctccagagct gggttagttg gtatgcttga cctgctaacg tcaggggata ctgatatagg      2760
gttcacatcc tgggacattg acatcatggg atttgttcaa cagcgtagga aactggagat      2820
```

```
gttcacatac atgaggtttg atgcagagtt cactttctta actgtgggag cgactggtgc   2880
tgcgccagcc actgttatcc aatatatgta tgtaccacca ggtgcaccca aacccaccca   2940
acgtgattcc tttgaatggc agacttcaac taatccttcc atctttgtca aggttagtga   3000
tcccccagcc caggtctcgg taccctttcat gtcacctgca gcagcatatc aatggttta   3060 tgatggatac cctacatttg gcaatcaccc aaccaatcaa gacttcagat acggaatctg   3120
tcccaataat ctcatgggga cttttctgcgt gcgagttctt ggttcagaga agctcaccga   3180
ggccctcaga gtgcgcatct acatgcgcat caagcacgtc agagcatgga ttcctagacc   3240
acttaggtcg cagaaatatc ttctgaagaa ttatccaaac ttcgatgggg ctgatgtcac   3300
acctactagt gcatctagag ccaatatcac aacagctggc gtgtttggtc aacagtcagg   3360
ggcagtctat gttgggaatt ataaaatagt taacagacat ctggcaactg aagcagactg   3420
gaatagttta gtctgggaaa gctacaacag ggacctctta gtgaccagtg tgaatgcaca   3480
aggttgcgat accatagcac gttgctcgtg caaggcaggg gttatttct gcaagtccat   3540 gaacaagcat tatcctgtca gtttccaagg acctggaatt gtcgaggtcc aagccaatga   3600
attctatcca cacagatacc aaacccacgt tctactcggg catggtacat cgataccagg   3660
ggactgtggt ggtatcctca gatgccaaca cggtgtcatt ggcctagtga ccatgggagg   3720
tgatggcttg gttggttttg cagacctcag agacctgttt tggctcgacg atgaagcgat   3780
ggaacagggg gtcacggatt acatcaaggg acttggtgat gcttttggta cagggttcac   3840
tgattccatc tctagggaga tccagcaact taaaaactac ctcctaggtt cagaaaatgt   3900
ggtagagaag atccttaaag cactaatcaa agtagtttca gcattggtga tagttgttag   3960
gagtgactat gacctggtca ccctgaccgc aaccctcgct ttaattgggt gtcacggaag   4020
tccctgggcc tggctcaaat ccaaagtttc caatctactt gacattccta ttgcacaaaa   4080
gcagagtgac tcatggctca agaaattcac agaaatggct aatgctgcta gaggtcttga   4140
atggattgca aataaaatta gcaagtttat agactgggtg aaagagaaga ttgtcccagc   4200
agctaaagaa aaggtggagt tcctctccaa tctcaagcaa ttgccccttat tagagtccca   4260 gatcgccaac attgaacagt cagcagctag tcaggaagat ttagaaaatc tattcagtaa   4320
tgttgcctac ctagcccatt attgcagaaa gttccagcca ctctacgcct cagaggcgaa   4380
gaggatctac gccatggaga aaagaatcaa taattacatg cagttcaaga gcaaacaccg   4440
aattgaaccc gtatgtttaa taattagagg accccctggc accggaaagt cactggcaac   4500
aggcattatt ggtagagcta ttgcagagaa ataccactcc agtgtatatt ccttgccccc   4560
agacccagat cactttgatg gttacaagca acaagtggtt acagtgatgg atgacctttg   4620
ccaaaaccca gacgggaaag acatgtcact cttttgccag atggtttcta cagtagagtt   4680
tataccaccc atggctagcc tagaggaaaa gggtgtctca ttcacctcaa aatttgtgat   4740
tgcttccacc aactcatcta acatcatagt cccgactgtc tcagacagtg acgccattag   4800
aagaaggttc tacatggatt gtgacatcga ggttcctgaa tcgtttagga cacccccaggg   4860 aaggctagat gctgctagag ctgccaaact ttgttcagag aacaacactg ctaacttcaa   4920
aaagtgcagt cctctggttt gtggcaaagc cattcaactt agggatagga atcaggagt    4980 caggtacggt ttggattctg tcgtctcaga gctaatcaga gagtacaaca accgctcggc   5040
agttggtaac actattgagg cactctttca aggtccaccc caatttaaac caattagaat   5100
aacccttgac aaaccagcgc cagatgcaat tagtgatctt ttagcaagtg tggatagtga   5160
ggaggttaga caatattgta ggcaccaggg gtggattatt ccagagaagc ctaccaacat   5220
```

```
tgaaagacac gtaaataggg ctctgatgat tctacaatca gttaccactg tggttgcagt    5280
gatttcactt gtgtatgtca tctacaaact ctttgccggt ttccaaggtg cctactcggg    5340
gatgcccaag acagcggtca agaaaccagt actgagaact gctgtagctc agggacctgg    5400
gctagacttt gctctctctc tactgaagaa gaacatcaga aaatgccaga cagaccaggg    5460
gcacttcacc ttgttaggaa ttagggatag attagctgtg ctcccaagac atgcttcacc    5520
aggagactca atttggattg aacacaagca aattaaaatt ctggacgccg ttgagctggt    5580
cgatgaacaa caagtcaatc ttgagcttac actgatcacc ctcgacacca atgaaaagtt    5640
cagagacatt acaaagttta ttcctgagca aattgaaggg actgcagatg ccacccttgt    5700
catcaacaca gaggctatgc catcaatgtt tgttccagtc ggtgatgtcc agcaatatgg    5760
ctttcttaac ctcagtggca aaccaacaca cagaaccatg atgtataact cccaaccaa     5820
agcaggacag tgtggaggag tggtcacctc agtgggaaga attgtgggca tccacattgg    5880
aggcaatggc cgccagggct tctgcgctgc actcaaacgc agttattttg cttctgaaca    5940
aggtgagatt caatgatga aatccaataa agagacaggc aatttcaata tcaatggtcc     6000
cactaaaact aaacttgaac ccagtgtttt ccacgatgtg tttgaaggag tcaaagaacc    6060
agcagtcctt cactccaaag acaagagact tgaggttgat tttgagactg ctctttctc    6120
caaatacata gggaacaaga tgcatgagcc agatgagtac atgatccagg ccgcgaacca    6180
ttatgcagac cagcttaaac aattggacat cgatacatca aaaatgagca tggaggatgc    6240
ctgttatgga acagaattcc tagaaggaat tgatttggca acaagtgcgg ggtacccta     6300
caacgcatta ggcataaaga aaaggacat tctgaacccc caaaccaggg atgtgactaa     6360
aatgaagatg tacttggaca aatatggtat tgacctccct tactccactt atgtcaaaga    6420
tgaacttaga gctaaggata aaatcaagaa agggaaatct agactgattg aggccagtag    6480
cattaatgac tcagtctacc ttagaatgtg ctttggccac ttgtatgaga aattccatgc    6540
aaatccaggg acgatcactg gctcggcagt tggttgtaac ccagacactt tctggagtaa    6600
aatccctata atgcttcctg gttccctctt tgcctttgat tatactgggt atgatgctag    6660
tcttctcct gcttggttta gggctttaga aatcgttctt aaaagattag gttatgatca     6720
agatgctatc tcactaattg agggaatcaa tcactcccat cacatttaca gaaaccaaac    6780
gtactgtgta atgggtggga tgccatctgg gtgttctggt actagcattt tcaattctat    6840
gattaacaac attattatca ggactcttct aatcagaacc tttaaaggaa ttgatttgga    6900
tgaattaaat atgattgcat atggagatga tgttcttgct agttaccctt tccctattga    6960
ttgtgctgaa cttgcaaaaa caggattgga atatggttta gtcatgacac cggctgacaa    7020
atctacttgt ttcaatgagg taaattggga aaatgcaacg ttcctcaaga ggggattcaa    7080
accagatgag caatatccgt tcctcatcca cccaaccatg ccgatgaagg aaatacacga    7140
gtccattcgt tggactaaag acccacgtaa cacacaagat cacgtgcggt cactgtgcct    7200
cctagcatgg cataatggta gggaaaccta tgaggaattt gttgacaaaa ttagaactgt    7260
accaattggc aaagtcttag ctcttccaaa ttatgataac ttgagaagaa attggcttga    7320
actgttttaa ataatgatct aaaatagttt caattggcaa catctttggt gcccctggg     7380
cttgacaaag tcaccaaagc tcaattcccc caacccagtg gggtaaaaaa aaaaaaaa     7438
```

<210> SEQ ID NO 83
<211> LENGTH: 2193
<212> TYPE: PRT

<213> ORGANISM: Artificial Sequence
<220> FEATURE:
<223> OTHER INFORMATION: Deduced amino acid sequence EV79

<400> SEQUENCE: 83

```
Met Gly Ala Gln Val Ser Thr Gln Lys Thr Gly Ser His Glu Asn Gln
1               5                   10                  15

Asn Ile Ala Ala Ser Gly Ser Thr Ile Asn Tyr Thr Thr Ile Asn Tyr
            20                  25                  30

Tyr Lys Asp Ser Tyr Ala Ala Ser Ala Ala Lys Gln Asp Phe Ser Gln
        35                  40                  45

Asp Pro Ser Lys Phe Thr Gln Pro Val Val Asp Ala Leu Lys Glu Thr
    50                  55                  60

Ala Pro Pro Leu Lys Ser Pro Ser Ala Glu Ala Cys Gly Tyr Ser Asp
65                  70                  75                  80

Arg Val Ala Gln Leu Thr Leu Gly Asn Ser Thr Ile Thr Thr Gln Glu
                85                  90                  95

Ala Ala Asn Ile Thr Val Gly Tyr Gly Glu Trp Pro Glu Tyr Ser Lys
            100                 105                 110

Asp Thr Glu Ala Thr Ala Val Asp Lys Pro Thr Arg Pro Asp Val Ser
        115                 120                 125

Val Asn Arg Phe Tyr Thr Leu Pro Ala Lys Leu Trp Ala Asn Asn Ser
    130                 135                 140

Lys Gly Trp Tyr Trp Lys Phe Pro Asp Val Leu Cys Glu Leu Gly Val
145                 150                 155                 160

Phe Gly Gln Asn Ala Gln Tyr His Tyr Leu Tyr Arg Ser Gly Phe Cys
                165                 170                 175

Ile His Val Gln Cys Asn Ala Ser Lys Phe His Gln Gly Thr Leu Leu
            180                 185                 190

Val Ala Ala Ile Pro Glu Leu Met Leu Ala Arg Ser Ser Asn Asp Thr
        195                 200                 205

Asn Pro Ala Thr Ala Pro His Pro Pro Tyr Asn Ala Thr Gln Pro Gly
    210                 215                 220

Glu Ala Gly Lys Glu Phe Ala Tyr Pro Tyr Ile Leu Asp Ser Gly Ile
225                 230                 235                 240

Pro Leu Ser Gln Ala Leu Ile Phe Pro His Gln Trp Ile Asn Leu Arg
                245                 250                 255

Thr Asn Asn Cys Ala Thr Ile Val Met Pro Tyr Ile Asn Cys Leu Pro
            260                 265                 270

Phe Asp Ser Ala Leu Asn His Cys Asn Phe Ser Leu Val Val Ile Pro
        275                 280                 285

Val Ala Pro Leu Ala Tyr Asn Glu Gly Ala Thr Thr Ala Ile Pro Ile
    290                 295                 300

Thr Val Thr Val Ala Pro Met Cys Ser Glu Phe Ser Gly Leu Arg Gln
305                 310                 315                 320

Ala Val Val Gln Gly Leu Pro Ala Glu Leu Lys Pro Gly Thr Asn Gln
                325                 330                 335

Phe Leu Thr Thr Asp Asp Gly Val Ser Ala Pro Ile Leu Pro Gly Phe
            340                 345                 350

His Pro Thr Pro Glu Met His Ile Pro Gly Glu Val Lys Asn Leu Leu
        355                 360                 365

Glu Ile Cys Gln Val Glu Ser Ile Leu Glu Val Asn Asn Leu Thr Thr
    370                 375                 380

Asn Lys Ala Ala Ser Gln Leu Met Thr Arg Leu Leu Ile Pro Val Glu
```

```
                385                 390                 395                 400
Ala Gln Thr Ala Val Asp Ala Leu Cys Ala Ala Phe Lys Val Asp Pro
                    405                 410                 415
Gly Arg Asp Gly Pro Trp Gln Ser Thr Leu Val Gly Gln Ile Cys Arg
                420                 425                 430
Tyr Tyr Thr Gln Trp Ser Gly Ser Leu Glu Val Thr Phe Met Phe Thr
            435                 440                 445
Gly Ser Phe Met Ala Thr Gly Lys Met Leu Ile Ala Tyr Thr Pro Pro
        450                 455                 460
Gly Ala Pro Gln Pro Ala Asn Arg Arg Ile Ala Met Leu Gly Thr His
465                 470                 475                 480
Val Ile Trp Asp Phe Gly Leu Gln Ser Ser Val Thr Leu Val Ile Pro
                    485                 490                 495
Trp Ile Ser Asn Thr His Tyr Arg Ala Met Gly Ser Asn Asp Tyr Phe
                500                 505                 510
Asp Tyr Tyr Ser Ala Gly Ile Val Thr Ile Trp Tyr Gln Thr Asn Phe
            515                 520                 525
Val Val Pro Ser Gly Ala Pro Thr Ser Ala Tyr Ile Ile Ala Leu Ala
        530                 535                 540
Ala Ala Gln Lys Asn Phe Thr Leu Arg Leu Pro Lys Asp Thr Gly Asp
545                 550                 555                 560
Ile Ser Gln Thr Ala Ile Leu Gln Gly Asp Pro Ile Glu Glu Ala Ile
                    565                 570                 575
Asn Asn Thr Val Ala Gly Thr Leu Asn Arg Ala Leu Gly Ser Ala Ser
                580                 585                 590
His Thr Thr Ala Gln Asn Thr Gln Gln Ser Ser His Gln Ile Gly Thr
            595                 600                 605
Gly Glu Val Pro Ala Leu Gln Ala Ala Glu Thr Gly Ala Thr Ser Asn
        610                 615                 620
Thr Ser Asp Glu Asn Met Leu Glu Thr Arg Cys Val Ile Asn Ser His
625                 630                 635                 640
Ser Val Ala Glu Thr Ser Ile Ser His Phe Phe Ser Arg Ala Gly Leu
                    645                 650                 655
Val Gly Met Leu Asp Leu Leu Thr Ser Gly Asp Thr Asp Ile Gly Phe
                660                 665                 670
Thr Ser Trp Asp Ile Asp Ile Met Gly Phe Val Gln Gln Arg Arg Lys
            675                 680                 685
Leu Glu Met Phe Thr Tyr Met Arg Phe Asp Ala Glu Phe Thr Phe Leu
        690                 695                 700
Thr Val Gly Ala Thr Gly Ala Ala Pro Ala Thr Val Ile Gln Tyr Met
705                 710                 715                 720
Tyr Val Pro Pro Gly Ala Pro Lys Pro Thr Gln Arg Asp Ser Phe Glu
                    725                 730                 735
Trp Gln Thr Ser Thr Asn Pro Ser Ile Phe Val Lys Val Ser Asp Pro
                740                 745                 750
Pro Ala Gln Val Ser Val Pro Phe Met Ser Pro Ala Ala Ala Tyr Gln
            755                 760                 765
Trp Phe Tyr Asp Gly Tyr Pro Thr Phe Gly Asn His Pro Thr Asn Gln
        770                 775                 780
Asp Phe Arg Tyr Gly Ile Cys Pro Asn Asn Leu Met Gly Thr Phe Cys
785                 790                 795                 800
Val Arg Val Leu Gly Ser Glu Lys Leu Thr Glu Ala Leu Arg Val Arg
                    805                 810                 815
```

```
Ile Tyr Met Arg Ile Lys His Val Arg Ala Trp Ile Pro Arg Pro Leu
            820                 825                 830

Arg Ser Gln Lys Tyr Leu Leu Lys Asn Tyr Pro Asn Phe Asp Gly Ala
            835                 840                 845

Asp Val Thr Pro Thr Ser Ala Ser Arg Ala Asn Ile Thr Thr Ala Gly
            850                 855                 860

Val Phe Gly Gln Gln Ser Gly Ala Val Tyr Val Gly Asn Tyr Lys Ile
865                 870                 875                 880

Val Asn Arg His Leu Ala Thr Glu Ala Asp Trp Asn Ser Leu Val Trp
                885                 890                 895

Glu Ser Tyr Asn Arg Asp Leu Leu Val Thr Ser Val Asn Ala Gln Gly
                900                 905                 910

Cys Asp Thr Ile Ala Arg Cys Ser Cys Lys Ala Gly Val Tyr Phe Cys
                915                 920                 925

Lys Ser Met Asn Lys His Tyr Pro Val Ser Phe Gln Gly Pro Gly Ile
            930                 935                 940

Val Glu Val Gln Ala Asn Glu Phe Tyr Pro His Arg Tyr Gln Thr His
945                 950                 955                 960

Val Leu Leu Gly His Gly Thr Ser Ile Pro Gly Asp Cys Gly Gly Ile
                965                 970                 975

Leu Arg Cys Gln His Gly Val Ile Gly Leu Val Thr Met Gly Gly Asp
            980                 985                 990

Gly Leu Val Gly Phe Ala Asp Leu  Arg Asp Leu Phe  Trp  Leu Asp Asp
            995                 1000                1005

Glu Ala  Met Glu Gln Gly Val  Thr Asp Tyr Ile Lys  Gly Leu Gly
     1010            1015                1020

Asp Ala  Phe Gly Thr Gly Phe  Thr Asp Ser Ile Ser  Arg Glu Ile
     1025            1030                1035

Gln Gln  Leu Lys Asn Tyr Leu  Leu Gly Ser Glu Asn  Val Val Glu
     1040            1045                1050

Lys Ile  Leu Lys Ala Leu Ile  Lys Val Val Ser Ala  Leu Val Ile
     1055            1060                1065

Val Val  Arg Ser Asp Tyr Asp  Leu Val Thr Leu Thr  Ala Thr Leu
     1070            1075                1080

Ala Leu  Ile Gly Cys His Gly  Ser Pro Trp Ala Trp  Leu Lys Ser
     1085            1090                1095

Lys Val  Ser Asn Leu Leu Asp  Ile Pro Ile Ala Gln  Lys Gln Ser
     1100            1105                1110

Asp Ser  Trp Leu Lys Lys Phe  Thr Glu Met Ala Asn  Ala Ala Arg
     1115            1120                1125

Gly Leu  Glu Trp Ile Ala Asn  Lys Ile Ser Lys Phe  Ile Asp Trp
     1130            1135                1140

Val Lys  Glu Lys Ile Val Pro  Ala Ala Lys Glu Lys  Val Glu Phe
     1145            1150                1155

Leu Ser  Asn Leu Lys Gln Leu  Pro Leu Leu Glu Ser  Gln Ile Ala
     1160            1165                1170

Asn Ile  Glu Gln Ser Ala Ala  Ser Gln Glu Asp Leu  Glu Asn Leu
     1175            1180                1185

Phe Ser  Asn Val Ala Tyr Leu  Ala His Tyr Cys Arg  Lys Phe Gln
     1190            1195                1200

Pro Leu  Tyr Ala Ser Glu Ala  Lys Arg Ile Tyr Ala  Met Glu Lys
     1205            1210                1215
```

-continued

| | | | | | | | | | | | |
|---|---|---|---|---|---|---|---|---|---|---|---|
| Arg | Ile | Asn | Asn | Tyr | Met | Gln | Phe | Lys | Ser | Lys | His | Arg | Ile | Glu |
| 1220 | | | | | 1225 | | | | 1230 | | |

Arg Ile Asn Asn Tyr Met Gln Phe Lys Ser Lys His Arg Ile Glu
1220                 1225              1230

Pro Val Cys Leu Ile Ile Arg Gly Pro Gly Thr Gly Lys Ser
1235                 1240              1245

Leu Ala Thr Gly Ile Ile Gly Arg Ala Ile Ala Glu Lys Tyr His
1250                 1255              1260

Ser Ser Val Tyr Ser Leu Pro Pro Asp Pro Asp His Phe Asp Gly
1265                 1270              1275

Tyr Lys Gln Gln Val Val Thr Val Met Asp Asp Leu Cys Gln Asn
1280                 1285              1290

Pro Asp Gly Lys Asp Met Ser Leu Phe Cys Gln Met Val Ser Thr
1295                 1300              1305

Val Glu Phe Ile Pro Pro Met Ala Ser Leu Glu Glu Lys Gly Val
1310                 1315              1320

Ser Phe Thr Ser Lys Phe Val Ile Ala Ser Thr Asn Ser Ser Asn
1325                 1330              1335

Ile Ile Val Pro Thr Val Ser Asp Ser Asp Ala Ile Arg Arg Arg
1340                 1345              1350

Phe Tyr Met Asp Cys Asp Ile Glu Val Pro Glu Ser Phe Arg Thr
1355                 1360              1365

Pro Gln Gly Arg Leu Asp Ala Ala Arg Ala Ala Lys Leu Cys Ser
1370                 1375              1380

Glu Asn Asn Thr Ala Asn Phe Lys Lys Cys Ser Pro Leu Val Cys
1385                 1390              1395

Gly Lys Ala Ile Gln Leu Arg Asp Arg Lys Ser Gly Val Arg Tyr
1400                 1405              1410

Gly Leu Asp Ser Val Val Ser Glu Leu Ile Arg Glu Tyr Asn Asn
1415                 1420              1425

Arg Ser Ala Val Gly Asn Thr Ile Glu Ala Leu Phe Gln Gly Pro
1430                 1435              1440

Pro Gln Phe Lys Pro Ile Arg Ile Thr Leu Asp Lys Pro Ala Pro
1445                 1450              1455

Asp Ala Ile Ser Asp Leu Leu Ala Ser Val Asp Ser Glu Glu Val
1460                 1465              1470

Arg Gln Tyr Cys Arg His Gln Gly Trp Ile Ile Pro Glu Lys Pro
1475                 1480              1485

Thr Asn Ile Glu Arg His Val Asn Arg Ala Leu Met Ile Leu Gln
1490                 1495              1500

Ser Val Thr Thr Val Val Ala Val Ile Ser Leu Val Tyr Val Ile
1505                 1510              1515

Tyr Lys Leu Phe Ala Gly Phe Gln Gly Ala Tyr Ser Gly Met Pro
1520                 1525              1530

Lys Thr Ala Val Lys Lys Pro Val Leu Arg Thr Ala Val Ala Gln
1535                 1540              1545

Gly Pro Gly Leu Asp Phe Ala Leu Ser Leu Leu Lys Lys Asn Ile
1550                 1555              1560

Arg Lys Cys Gln Thr Asp Gln Gly His Phe Thr Leu Leu Gly Ile
1565                 1570              1575

Arg Asp Arg Leu Ala Val Leu Pro Arg His Ala Ser Pro Gly Asp
1580                 1585              1590

Ser Ile Trp Ile Glu His Lys Gln Ile Lys Ile Leu Asp Ala Val
1595                 1600              1605

Glu Leu Val Asp Glu Gln Gln Val Asn Leu Glu Leu Thr Leu Ile

```
                 1610                1615                1620

Thr Leu Asp Thr Asn Glu Lys Phe Arg Asp Ile Thr Lys Phe Ile
        1625                1630                1635

Pro Glu Gln Ile Glu Gly Thr Ala Asp Ala Thr Leu Val Ile Asn
        1640                1645                1650

Thr Glu Ala Met Pro Ser Met Phe Val Pro Val Gly Asp Val Gln
        1655                1660                1665

Gln Tyr Gly Phe Leu Asn Leu Ser Gly Lys Pro Thr His Arg Thr
        1670                1675                1680

Met Met Tyr Asn Phe Pro Thr Lys Ala Gly Gln Cys Gly Gly Val
        1685                1690                1695

Val Thr Ser Val Gly Arg Ile Val Gly Ile His Ile Gly Gly Asn
        1700                1705                1710

Gly Arg Gln Gly Phe Cys Ala Ala Leu Lys Arg Ser Tyr Phe Ala
        1715                1720                1725

Ser Glu Gln Gly Glu Ile Gln Trp Met Lys Ser Asn Lys Glu Thr
        1730                1735                1740

Gly Asn Phe Asn Ile Asn Gly Pro Thr Lys Thr Lys Leu Glu Pro
        1745                1750                1755

Ser Val Phe His Asp Val Phe Glu Gly Val Lys Glu Pro Ala Val
        1760                1765                1770

Leu His Ser Lys Asp Lys Arg Leu Glu Val Asp Phe Glu Thr Ala
        1775                1780                1785

Leu Phe Ser Lys Tyr Ile Gly Asn Lys Met His Glu Pro Asp Glu
        1790                1795                1800

Tyr Met Ile Gln Ala Ala Asn His Tyr Ala Asp Gln Leu Lys Gln
        1805                1810                1815

Leu Asp Ile Asp Thr Ser Lys Met Ser Met Glu Asp Ala Cys Tyr
        1820                1825                1830

Gly Thr Glu Phe Leu Glu Gly Ile Asp Leu Ala Thr Ser Ala Gly
        1835                1840                1845

Tyr Pro Tyr Asn Ala Leu Gly Ile Lys Lys Lys Asp Ile Leu Asn
        1850                1855                1860

Pro Gln Thr Arg Asp Val Thr Lys Met Lys Met Tyr Leu Asp Lys
        1865                1870                1875

Tyr Gly Ile Asp Leu Pro Tyr Ser Thr Tyr Val Lys Asp Glu Leu
        1880                1885                1890

Arg Ala Lys Asp Lys Ile Lys Lys Gly Lys Ser Arg Leu Ile Glu
        1895                1900                1905

Ala Ser Ser Ile Asn Asp Ser Val Tyr Leu Arg Met Cys Phe Gly
        1910                1915                1920

His Leu Tyr Glu Lys Phe His Ala Asn Pro Gly Thr Ile Thr Gly
        1925                1930                1935

Ser Ala Val Gly Cys Asn Pro Asp Thr Phe Trp Ser Lys Ile Pro
        1940                1945                1950

Ile Met Leu Pro Gly Ser Leu Phe Ala Phe Asp Tyr Thr Gly Tyr
        1955                1960                1965

Asp Ala Ser Leu Ser Pro Ala Trp Phe Arg Ala Leu Glu Ile Val
        1970                1975                1980

Leu Lys Arg Leu Gly Tyr Asp Gln Asp Ala Ile Ser Leu Ile Glu
        1985                1990                1995

Gly Ile Asn His Ser His His Ile Tyr Arg Asn Gln Thr Tyr Cys
        2000                2005                2010
```

```
Val Met Gly Gly Met Pro Ser Gly Cys Ser Gly Thr Ser Ile Phe
    2015            2020                2025

Asn Ser Met Ile Asn Asn Ile Ile Ile Arg Thr Leu Leu Ile Arg
    2030            2035                2040

Thr Phe Lys Gly Ile Asp Leu Asp Glu Leu Asn Met Ile Ala Tyr
    2045            2050                2055

Gly Asp Asp Val Leu Ala Ser Tyr Pro Phe Pro Ile Asp Cys Ala
    2060            2065                2070

Glu Leu Ala Lys Thr Gly Leu Glu Tyr Gly Leu Val Met Thr Pro
    2075            2080                2085

Ala Asp Lys Ser Thr Cys Phe Asn Glu Val Asn Trp Glu Asn Ala
    2090            2095                2100

Thr Phe Leu Lys Arg Gly Phe Lys Pro Asp Glu Gln Tyr Pro Phe
    2105            2110                2115

Leu Ile His Pro Thr Met Pro Met Lys Glu Ile His Glu Ser Ile
    2120            2125                2130

Arg Trp Thr Lys Asp Pro Arg Asn Thr Gln Asp His Val Arg Ser
    2135            2140                2145

Leu Cys Leu Leu Ala Trp His Asn Gly Arg Glu Thr Tyr Glu Glu
    2150            2155                2160

Phe Val Asp Lys Ile Arg Thr Val Pro Ile Gly Lys Val Leu Ala
    2165            2170                2175

Leu Pro Asn Tyr Asp Asn Leu Arg Arg Asn Trp Leu Glu Leu Phe
    2180            2185                2190

<210> SEQ ID NO 84
<211> LENGTH: 5
<212> TYPE: PRT
<213> ORGANISM: Artificial Sequence
<220> FEATURE:
<223> OTHER INFORMATION: N-terminal myristylation concensus site
<220> FEATURE:
<221> NAME/KEY: misc_feature
<222> LOCATION: (1)..(5)
<223> OTHER INFORMATION: "Xaa" on positions 2-4 stands for unknown amino
      acid, "Xaa" on position 5 stands for Ser or Thr

<400> SEQUENCE: 84

Gly Xaa Xaa Xaa Xaa
1               5
```

ENTEROVIRUS, VACCINES, MEDICAMENTS AND DIAGNOSTIC KITS

CROSS-REFERENCE TO RELATED APPLICATION

This application is a continuation of PCT International Patent Application No. PCT/NL2004/000184 filed on Mar. 12, 2004, designating the United States of America, and published in English, as PCT International Publication No. WO 2004/104189 A1 on Dec. 2, 2004 the contents of the entirety of which are incorporated herein by this reference.

BACKGROUND

The invention relates to the field of medicine. The invention particularly relates to the isolation of a new enterovirus and methods for detection, identification, diagnosis, treatment and prevention of the enterovirus.

According to the most recent classification of viruses, the family of the Picornaviridae is divided in six genera, among which are the human enteroviruses, rhinoviruses, parechoviruses, aphthoviruses, cardioviruses, and hepatoviruses. The genus enterovirus includes the following human virus species: polioviruses and human enterovirus groups A to D. Poliovirus (PV) consists of three serotypes: poliovirus 1 (PV-1), PV-2 and PV-3. Human enterovirus A (HEV-A) consists of 12 serotypes, including coxsackievirus A2, A16 and enterovirus 71 (more details concerning these viral strains are listed in Table 1). Human enterovirus B (HEV-B) consists of 37 serotypes; human enterovirus C (HEV-C) consists of 11 serotypes and human enterovirus D (HEV-D) consists of 2 serotypes. Enteroviruses are single strand RNA viruses. Their genomes comprise approximately 7500 nt.

Enteroviruses cause a wide spectrum of clinical syndromes ranging from mild fever to respiratory infections, meningitis, encephalitis, paralytic poliomyelitis and myocarditis. An estimated 10 to 30 million enteroviral infections occur annually in America, causing significant short-term mobility and economic impact. Life-threatening enteroviral infections may occur, especially in high-risk individuals such as immunocompromised patients.

Hence, enteroviruses cause a wide spectrum of clinical syndromes. Enteroviral infections often result in "general" symptoms, such as diarrhoea and fever, which are involved in many different kinds of disease. Therefore, symptoms of an enteroviral infection cannot be directly correlated to an enteroviral genus-related disease. Characterization of the causative agent is therefore often necessary in order to provide adequate treatment. Once a causative agent is known, efficient diagnosis, prevention and/or treatment becomes possible.

DISCLOSURE OF THE INVENTION

The newly found enterovirus, (designated EV79) was characterized and sequenced. A nucleic acid sequence of a prototype EV79 is provided in FIG. 19 and parts thereof in FIG. 2B. In one aspect, the invention therefore provides an isolated and/or recombinant nucleic acid comprising a sequence as depicted in FIG. 19 and/or FIG. 2B, or a functional part, derivative and/or analogue thereof. The virus EV79 is characterized by the prototype, however, many natural variants of the prototype EV79 virus exist. The existence of such natural variants is normal for RNA viruses that undergo frequent mutation through, for instance, the introduction of mistakes by the polymerases that copy the genome.

EV79 viruses that have a slightly divergent nucleic acid sequence are thus also provided by the present invention. Such viruses are considered to be a derivative of the nucleic acid having the prototype nucleic acid sequence. The variant does not necessarily have to be a natural variant. It is very well possible to generate variants through recombinant means. For instance, many parts of the virus can be altered through nucleotide substitution to make use of the redundancy in the triplet genetic code for particular amino acids, thus, without altering the amino acid sequence of the encoded proteins. However, even amino acid alterations can typically be introduced without affecting the replicating and coding potential of the viruses. For instance, conservative amino acid substitutions are often tolerated.

Alterations in the prototype virus may be up to 70% of the nucleic acid sequence without altering the replicating potential of the virus. Thus, in one embodiment, the invention provides an isolated and/or recombinant nucleic acid that is at least 70% homologous to a nucleic acid of the prototype EV79. Most of the viable variants however are at least 95% homologous and more preferably at least 99% to a nucleic acid according to the prototype EV79. The homology between different enteroviruses in the UTR regions is typically high, for this reason, the homology in this application is measured in a region outside the UTR regions, preferably in a protein coding region. Thus, the invention provides a derivative of EV79 virus comprising at least 95% homology and preferably at least 99% homology (on the nucleic acid level or on the protein level) in at least one protein coding region depicted in FIG. 20, FIG. 3, Table 10 or Table 11.

The nucleic acid of the virus or parts thereof can be cloned and used as a probe to detect the virus in samples. Thus the present invention further provides an isolated and/or recombinant nucleic acid comprising a stretch of 100 consecutive nucleotides of a nucleic acid of the prototype virus, or a region that is at least 95% and preferably at least 99% homologous to 100 consecutive nucleotides, wherein the 100 nucleotides are outside the UTR region. In a preferred embodiment, the part essentially does not overlap with a UTR region. In a preferred embodiment, the part is in a protein coding domain. A stretch of 100 consecutive nucleotides is considered to be a functional part of the virus of the present invention.

A preferred part of EV79 is a nucleic acid encoding a protein as depicted in FIG. 20, Tables 10 and 11, or FIG. 3. Further provided is a bacterial vector comprising a nucleic acid of EV79 or a functional part, derivative and/or analogue thereof. Further provided is a bacterium comprising the bacterial vector. Considering the divergence with other known enteroviruses, the sequence of EV79 or a part thereof can be used to generate a primer that is specific for EV79 and thus capable of specifically replicating EV79 nucleic acid. Similarly, a probe can be generated that specifically hybridizes to EV79 nucleic acid under stringent conditions. Thus, the invention further provides a primer and/or probe, capable of specifically hybridizing to a nucleic acid of an EV79 virus or functional part, derivative or analogue thereof. Preferably, the primer or probe is capable of hybridizing to the nucleic acid under stringent conditions.

In a preferred embodiment, the primer comprises a consecutive stretch of between 10 and 50 nucleotides of a sequence as depicted in FIG. 19, preferably between 15 and 25 nucleotides. The person skilled in the art is well capable of determining the conditions needed for specific hybridization of a nucleic acid to a nucleic acid of EV79. Typically, the specificity increases with increasing size of overlap with and homology with the nucleic acid depicted in FIG. 19. A typical probe specific for a nucleic acid depicted in FIG. 19, comprises at least 20 consecutive nucleotides. A probe may essentially comprise the entire EV79 sequence. However, a probe specific for EV79 has a size of between 20 and 2000 nucleotides and a homology of at least 95, and preferably at least 99% with the nucleic acid depicted in FIG. 19. Probes may be labeled directly or indirectly via an intermediate. Primers may be generated for sequences throughout the genome of EV79, however when a specific amplification of EV79 sequences (or variants thereof) is desired preferably at least one primer is chosen outside the UTR region.

In a particularly preferred embodiment, both primers are chosen outside the UTR region. In a preferred embodiment, a primer comprises sufficient sequence divergence with related enteroviruses, in this way specificity for EV79 sequences or variants thereof is warranted. Typically this is achieved by having at least one and preferably at least between 2-5 nucleotide differences in the primer compared to the sequence it intends to discriminate from, typically a related human enterovirus.

In a particularly preferred embodiment, the primer and/or probe comprises a sequence as depicted in FIG. 2B or Table 4.

The nucleic acid of the prototype virus encodes various proteins and polyproteins. These proteins are expressed, for instance, in cells producing the virus or transformed with a nucleic acid encoding the (poly)protein. The invention thus further provides an isolated and/or recombinant proteinaceous molecule comprising a sequence as depicted in FIG. 20, Table 10, Table 11, or FIG. 3, or a functional part, derivative and/or analogue thereof. Many different variants of the proteins having the same function in kind, not necessarily in amount are, as mentioned above, present in nature and can be generated artificially, thus the invention further provides an isolated and/or recombinant proteinaceous molecule that is at least 70% homologous to a proteinaceous molecule mentioned above. Such homologous proteins are considered derivatives of a protein encoded by the prototype. Preferably, a derivative protein comprises at least 95% and more preferably at least 99% homology with a protein encoded by the prototype EV79.

Fragments and parts of a proteinaceous molecule encoded by the prototype virus can be generated, such parts are therefore also provided by the present invention. In a preferred embodiment, provided is an isolated and/or recombinant proteinaceous molecule comprising a stretch of at least 30 consecutive amino acids of a proteinaceous molecule encoded by the prototype virus. A protein encoded by the prototype virus can be encoded through a variety of different nucleic acid sequences using the redundancy of the genetic code. Thus the invention further provides a nucleic acid encoding a protein depicted in FIG. 20, Table 10, Table 11, or FIG. 3.

The invention thus further provides an isolated or recombinant virus comprising an EV79 nucleic acid sequence or a functional part, derivative and/or analogue thereof. Also provided is an isolated or recombinant virus comprising a proteinaceous molecule as depicted in FIG. 20, Table 10, Table 11, or FIG. 3, or a functional part, derivative and/or analogue thereof. Subjects that have become infected with EV79 can display a number of different clinical and/or subclinical symptoms. Thus further provided is an isolated or recombinant virus or a functional part, derivative or analogue thereof capable of inducing an EV79-related disease, particularly diarrhea. The virus comprises substances that can be used to generate specific binding partners that are able to specifically bind the substance of the virus. Binding partners can, for instance, be generated by means of injection of the virus into an immuno-competent subject.

As a result of the immunization, the serum obtained from the subject will typically contain a number of different antibodies specific for the virus or an immunogenic part, derivative and/or analogue thereof. Specific binding partners (specific binding molecules) can of course be generated through a large variety of different technologies. For instance, phage display technologies could be generated. The method of producing the specific binding partner is not limited herein. The binding is typically specific for a proteinaceous part of the virus, but can, of course, also be specific for a virus specific post-translation modification of a protein contained in the virus.

Thus, the present invention further provides an isolated binding molecule capable of specifically binding a substance (preferably a proteinaceous molecule) of an EV79 virus, preferably against a proteinaceous molecule encoded by a nucleic acid of the prototype EV79. Preferably, a proteinaceous molecule comprising an amino acid sequence as depicted in FIG. 20, Table 10, Table 11, or FIG. 3, or a functional part, derivative and/or analogue thereof. The binding molecule can be capable of specifically binding a nucleic acid sequence of an EV79, preferably of FIG. 19 or FIG. 2B. The binding molecule is preferably a proteinaceous molecule. However, other binding molecules are also within the scope of the present invention. For instance, it is possible to generate protein mimetics or analogues having the same binding quality as a protein in kind not necessarily in amount.

Provided is a further method for producing a binding molecule according to the invention comprising—producing molecules capable of binding an EV79 virus or functional part, derivative or analogue thereof or an isolated and/or recombinant proteinaceous molecule encoded by a prototype nucleic acid of EV79, and—selecting a proteinaceous binding molecule that is specific for this virus and/or this proteinaceous molecule.

The overall homology of EV79 virus with other human enteroviruses is not very high. Thus many different binding molecules capable of specifically binding to EV79 virus can be generated. Such binding molecules can be used to detect EV79 virus in a sample. The invention thus further provides an isolated or recombinant virus, which is immune-reactive with a binding molecule capable of specifically binding EV79 virus. Similarly, the invention provides the use of an isolated and/or recombinant proteinaceous molecule as depicted in FIG. 20, Table 10, Table 11 or FIG. 3, or a functional part, derivative and/or analogue thereof, for detecting a binding molecule capable of specifically binding EV79 virus, or functional part, derivative and/or analogue of the virus in a sample. Vise versa, EV79 virus can be used to detect a molecule capable of specifically binding the virus in a sample.

Binding of EV79 virus to a susceptible target cell occurs via a specific receptor. This receptor can be used as a binding molecule of the invention. Preferably, the binding molecule comprises an antibody or functional equivalent thereof. The detection methods can be used to diagnose EV79-related disease in a subject. In one embodiment is provided a method for detecting an EV79 virus or functional part, derivative or analogue thereof in a sample, comprising hybridizing and/or amplifying a nucleic acid of the virus or functional part, derivative or analogue with an EV79 specific primer and/or probe and detecting hybridized and/or amplified product. Further provided is a kit, preferably a diagnostic kit comprising an EV79 virus or functional part, derivative or analogue thereof, a binding molecule according to the invention, and/or an EV79 virus specific primer/probe according to invention.

In a particular preferred embodiment is provided the use of a primer or probe capable of specifically hybridizing to a nucleic acid of an EV79 virus or functional part, derivative or analogue thereof, or a binding molecule capable of specifically binding a proteinaceous molecule depicted in FIG. 20, Table 10, Table 11 or FIG. 3, or an EV79 virus and/or a nucleic acid or functional part, derivative or analogue of a prototype EV79 for detecting and/or identifying an EV79 enterovirus in a sample. Preferably, the nucleic acid comprises a sequence as depicted in FIG. 19 or FIG. 2B.

The invention further provides a vaccine comprising EV79 virus or functional part, derivative or analogue thereof. Further provided is a vaccine comprising a proteinaceous molecule depicted in FIG. 20, Table 10, Table 11, or FIG. 3, or functional part, derivative and/or analogue of such a proteinaceous molecule. A proteinaceous molecule of the invention may be provided in the vaccine by itself or as a part of the protein or as derivatives or analogues thereof. A suitable analogue is a nucleic acid encoding an EV79 virus proteinaceous molecule or a functional part or derivative thereof. The nucleic acid may be used in a DNA vaccine approach, which is also provided in the present invention.

Further provided is a composition for immunizing a subject against at least one EV79 protein, this composition comprising a nucleic acid encoding an EV70 prototype protein, or a protein of a variant of EV79, or an immunogenic part, derivative and/or analogue of the EV79 prototype. As carrier for the DNA vaccine it is often suitable to incorporate an expressible EV79 virus nucleic acid in a viral replicon allowing replication of the EV79 virus nucleic acid in the target cell and thereby allowing amplification of the provided immune response. EV79 virus encoded proteins that are particularly suited for such a DNA vaccine approach are the VP1, VP2 and VP3 proteins depicted in FIG. 20, Table 10, Table 11, or FIG. 3, or a functional part, derivative and/or analogue thereof. A part of a VP protein preferably comprises an immunogenic part of the VP protein.

Other suitable candidates are the VP4, 2a, 2b and 3C protein or a functional part, derivative and/or analogue thereof. Typically a vaccine includes an appropriate adjuvant. Apart from the use in a vaccine the mentioned virus and/or proteinaceous molecules can also be used to generate and/or boost an EV79 virus specific immune response in a subject. The immune response can be either cellular or humoral. Thus, further provided is an isolated T-cell comprising a T-cell receptor that is specific for EV79 virus or a proteinaceous molecule encoded by a prototype EV79 virus. Further provided is an isolated B-cell producing an antibody specific for EV79 virus or a proteinaceous molecule encoded by an EV79 virus. The antibody or T-cell receptor can be cloned whereupon a cell line can be provided with an expression cassette comprising the nucleic acid encoding the cloned receptor or antibody. Thus, the invention further provides a cell producing such a receptor or antibody. Such a cell is preferably a cell that is suitable for large scale production of the mentioned proteins such as CHO cells.

It is also possible to provide a subject with passive immunity to EV79 virus. To this end the subject can be provided with an EV79 specific binding molecule of the invention. Such immunity can be used to provide a barrier for (further) infection with EV79 virus in the subject, thus further provided is a vaccine comprising an EV79 virus specific binding molecule according to the invention. In a preferred embodiment, passive immunity is provided by a human or humanized antibody capable of specifically binding an EV79 virus of the invention. Preferably, the antibody is produced by a human cell line, preferably the cell line comprises an adenovirus E1 region, preferably at least an E1A region of adenovirus 2 or adenovirus 5. The barrier does not have to be perfect.

The presence of a binding molecule at least reduces the spread of the virus to other target cells in the subject. The passive immunity may be administered to a subject as prophylactic to at least reduce the spread of EV79 virus in the subject when exposed to the virus. Alternatively, the passive immunity may be provided to a subject already infected with the virus. In the latter case, one or more EV79 virus specific binding molecules of the invention are used as a medicament to at least reduce the spread of the virus in the subject and thereby at least in part combat the virus infection. The invention thus further provides a medicament comprising an EV79 virus specific binding molecule according to the invention.

Further provided is the use of a virus of the invention or functional part, derivative or analogue thereof or a proteinaceous molecule of the invention or an EV79 virus specific binding molecule of the invention, for the preparation of a vaccine against an enterovirus-related disease.

Further provided is a method for treating an individual suffering from, or at risk of suffering from, an EV79-related disease, comprising administering to the individual a vaccine or medicament according to the invention. In yet another embodiment, provided is a method for determining whether an individual suffers from an EV79-related disease, comprising obtaining a sample from the individual and detecting an EV79 virus or functional part, derivative or analogue thereof in the sample.

In yet another embodiment, provided is an isolated cell, or recombinant or cell line comprising EV79 virus, or a functional part, derivative and/or analogue thereof. Preferably, the cell is a primate cell, preferably a monkey cell. In a preferred embodiment, the cell is a cell that replicates the EV79 virus of the invention. In a particular embodiment, the cell is a kidney cell. The cell can be used to produce the EV79 virus of the invention or to attenuate EV79 such that it becomes less pathogenic. Virus attenuation is spontaneous upon continued culture of the virus on the mentioned preferred cell lines. Attenuated EV79 virus can be used as a vaccine.

EV79 virus encodes endoproteases called protease 2a and protease 3C. Sequences in the prototype EV79 virus are depicted in FIG. 20. Proteases are important for the processing of the polyproteins encoded by EV79. The action of the protease is at least in part inhibited by a viral protease inhibitor as further described herein. Thus, the invention further provides a compound for at least in part inhibiting EV79 virus replication.

Of these compounds, the protease inhibitors are particularly preferred. Since the 2a and 3C enzymes recognize peptide substrates with a glutamine residue at the P(1) site, ketone-containing glutamine analogs (e.g., azaglutamine) can be used as inhibitors. Additionally, nitric oxide (NO)-releasing compounds like S-nitroso-N-acetyl-penicillamine (SNAP), glyceryl trinitrate (GTN), isosorbide dinitrate (ISDN) or glycerrhizin can be used to inhibit 3C activity. Also 5-(3,4-dichlorophenyl)methylhydantoin interferes with the post-translational processing of the polyprotein.

The vinylogous ethyl ester (AG7088, see structural formula 1 depicted below,) that inhibits human rhinovirus (HRV) 3C protease activity.

Structure of formula I

P2 = p-fluoro-benzyl: AG7088

Analogues of such protease inhibitors that comprise the same activity in kind not necessarily in amount are also provided by the present invention. Such analogues include, compounds comprising a peptide with the preferred sequence, wherein the peptide comprises a modification. Other analogues include compounds having protein mimetic activity that mimic the preferred amino-acid sequence.

Enteroviral RNAs are not capped instead they carry a small protein called VPg (encoded by the 3B gene) covalently attached to their 5' end. The so-called WIN-compounds insert themselves in the hydrophobic pocket of the picornaviral nucleocapsid, preventing the virus from uncoating its genomic RNA are preferred. Preferred compounds are: Pleconaril, 3-methylthio-5-aryl-4-isothiazolecarbonitriles or pyridyl imidazolidinones. Also nucleotide analogs like Ribavirin, mycophenolic acid, 6-azauridine and pyrazofurin or other RNA synthesis inhibitors like 3-methylkaempferol inhibit the replication of Picornaviruses. The invention thus further provides the use of a WIN-compound for the (preparation of a medicament for the) treatment of an EV79 infection.

The invention further provides a method for the treatment of a subject suffering from or at risk of suffering from an EV79 infection comprising administering to the subject a compound selected from the group consisting of a peptide containing a ketone-containing glutamine analog (e.g., azaglutamine), a nitric oxide (NO)-releasing compounds like S-nitroso-N-acetyl-penicillamine (SNAP), glyceryl trinitrate (GTN), isosorbide dinitrate (ISDN) or glycerrhizin, 5-(3,4-dichlorophenyl)methylhydantoin, a vinylogous ethyl ester (AG7088, having structural formula 1 depicted below);

Structure of formula I

P2 = p-fluoro-benzyl: AG7088

A so-called WIN compound such as a Pleconaril, 3-methylthio-5-aryl-4-isothiazolecarbonitrile or a pyridyl imidazolidinone, a nucleotide analogue such as ribavirin, mycophenolic acid, 6-azauridine or pyrazofurin, or an RNA synthesis inhibitor such as 3-methylkaempferol.

The invention further provides a proteinaceous molecule encoded by EV79 nucleic acid, wherein the proteinaceous molecule is a 2a or 3C protease or a functional equivalent thereof. Functional equivalents include a proteolytically active part and/or derivative having one or more conservative amino acid substitutions. There are many methods known in the art to determine whether a compound has anti-enteroviral activity, preferably anti-proteolytic activity of an enterovirus. The invention thus further provides a method for determining whether a compound comprises anti-enterovirus replication activity characterized in that the method utilizes EV79-virus or an EV79 protein involved in replication of EV79 or a functional part, derivative and/or analogue thereof. Preferably, the invention provides a method for determining whether a compound is capable of at least in part inhibiting a viral protease characterized in that the protease is a 2a and/or 3C protease of EV79 or a functional part, derivative and/or analogue thereof. Preferred compounds that can be tested for 3CL inhibiting quality are peptides (preferably hexapeptides) located N-terminally of 2a and/or 3C pro-cleavage sites, preferably a hexapeptide comprises a sequence that is immediately N-terminal of the 2a or 3C pro-cleavage site, preferably the (hexa)peptide comprises a modification for additional stability. Compounds effective in at least in part inhibiting 2a and/or 3C proteolytic activity can be used for the preparation of a medicament for the treatment of an individual suffering or at risk of suffering from-an EV79 virus infection.

One or more of the preferred anti-enteroviral replication compounds can be used as a medicament for the treatment of a subject suffering from or at risk of suffering from an EV79 virus infection. The invention thus further provides a medicament for the treatment of an individual suffering from an enterovirus infection or an individual at risk of suffering therefrom comprising wherein the enterovirus comprises a nucleic acid sequence of an EV79 prototype virus or a functional part, derivative and/or analogue thereof.

In the present invention several different recombinant viruses are produced using EV79 virus nucleic acid as a backbone. Such replication competent or replication defective recombinant virus can be used, for instance, as gene delivery vehicles. On the other hand, parts of an EV79 virus can be used in gene delivery vehicles that are based on other means for delivering genetic material to a cell. Thus the invention further provides a gene delivery vehicle comprising at least part of an EV79 virus nucleic acid, preferably of the prototype virus. Preferably, the gene delivery vehicle comprises a nucleic acid encoding a protein of EV79 virus or a functional part, derivative and/or analogue thereof.

The invention also shows chimeric enteroviruses comprising nucleic acid derived from at least two enteroviruses wherein at least one of these parts is derived from an EV79 virus. The EV79 virus-derived part comprises preferably at least 50 nucleotides of a protein coding domain. More preferably, the EV79-derived part comprises at least 500 and more preferably at least 1000 nucleotides of the sequence as depicted in FIG. 19 or a functional derivative thereof. In a preferred embodiment, the invention provides a chimeric enterovirus comprising at least 1000 nucleotides of a sequence as depicted in FIG. 19 and at least 1000 nucleotides of another enterovirus wherein the latter 1000 nucleotides comprise a sequence that is more than 5% sequence divergent with a sequence as depicted in FIG. 19.

The sequences of a number of EV79 virus-fragments are depicted in FIG. 2B and FIG. 3. The location of the fragments in the large genomic RNA is depicted in FIG. 3. The invention therefore, in one aspect, provides an isolated or recombinant virus comprising a nucleic acid sequence as depicted in Tables 2B and/or 3, or a functional part, derivative or analogue of the virus. With the aid of the identifying prototype fragments it is possible to further sequence the genome. One way of doing this is by primer walking on the genome. A primer is directed to a region of which the sequence is known and this primer is used to sequence a flanking region that is as yet unknown. A subsequent primer can be generated against the newly identified sequence and a further region can be sequenced.

The present invention provides a new enteroviral species called EV79. The EV79 virus was isolated from an immunocompromised patient suffering from severe diarrhea. Of course, now that the existence of this EV79 virus is known, it is possible to screen individuals and non-human animals for the presence of EV79. In FIG. 2A, a 5'-UTR region of a virus of the invention is depicted. FIG. 2B depicts a part of the genome of the virus adjacent to the 5'-UTR. This sequence is capable of distinguishing EV79 from other enteroviruses.

In one aspect, the invention thus provides an isolated or recombinant virus comprising a nucleic acid sequence as depicted in FIG. 2B, or a functional part, derivative or analogue of the virus. Now that a nucleic acid sequence as depicted in FIG. 2B is provided, it is easily possible to sequence other parts of an EV79 genome using current methods in the art. For instance, a probe can be generated based on the sequence of FIG. 2B. The probe can be bound to a solid support, after which the support can be incubated with a sample comprising EV79. After EV79 virus is bound, the virus can be isolated and its genome can subsequently be amplified. By aligning genomic sequences of closely related viruses, conserved sequence domains can be identified allowing the design of synthetic oligonucleotides. These oligonucleotides can be used to amplify additional and overlapping parts of the EV79 genome.

Alternatively, the EV79 virus can be amplified as described above from a pool of total nucleic acid isolated from a clinical sample or in vitro cultured cells.

It is preferred to use a primer based on the sequence of FIG. 2B and/or a "universal primer" set comprising random primers, preferably as described in patent application EP1276901 owned by the present applicant (incorporated herein by reference). In one preferred embodiment, a combination of a primer based on the sequence of FIG. 2B and a universal primer set is used. The universal primers are capable of binding an upstream region, including unidentified parts of an EV79 genome, enabling amplification of (part of) the genome extending beyond the nucleic acid sequence of FIG. 2B. After amplification, obtained product can be sequenced using, for instance, the dideoxy method.[23] Of course many other methods for sequencing the remaining part of the viral nucleic acid are available to the skilled person and these may be used as well.

The invention also provides a composition of matter comprising isolated EV79, and/or a virus essentially corresponding to EV79.

The term "a virus essentially corresponding to EV79" refers to EV79 viruses which are either identical to the EV79 strain identifiable by a sequence as depicted in FIG. 2B or which comprise one or more mutations as compared to the EV79 strain. These mutations may include naturally occurring variations, since RNA viruses are prone to mutations. Moreover, the mutations may include artificially made mutations. Preferably, the mutations still allow for detection of the EV79 variants using common detection methods such as hybridization, NASBA, RT-PCR and ELISA with EV79 specific nucleic acid and/or antibody.

The composition of matter may comprise live, attenuated and/or killed EV79 virus. The composition may as well comprise a functional part, derivative and/or analogue of the virus. In one embodiment, the composition comprises a recombinant vector derived from EV79 virus.

The sequence of FIG. 2B comprises at least part of an open reading frame encoding an amino acid sequence as depicted in FIG. 3. This amino acid sequence is also part of the EV79 virus strain obtained by the present inventors. The sequence comprises the VP4 region and at least part of the VP2 region of EV79. Hence, in another aspect, the invention provides an isolated or recombinant virus comprising an amino acid sequence as depicted in FIG. 3, or a functional part, derivative or analogue of the virus. Phylogenetic analysis demonstrates that EV79 is distantly related to some HEV-A enteroviruses including human enterovirus 71, coxsackievirus A2 and A16 with approximately 70% identity (FIG. 1).

An amino acid sequence as depicted in FIG. 20, Table 10, Table 11, and/or FIG. 3 can be encoded by different nucleic acid sequences. It is, for instance, possible to replace the third nucleotide of a codon by another nucleotide without changing the encoded amino acid residue. For instance, serine can be encoded by codons TCT, TCC, TCA, and TCG. Hence, the last nucleotide in the codons can be replaced by any other nucleotide, according to the "wobble" theory. As different organisms often utilize different codon usage, a nucleic acid encoding (part of) an EV79 virus can be artificially adapted to a certain organism that is used for producing the virus. Moreover, since viruses, especially RNA viruses, are prone to mutations, naturally occurring EV79 virus strains may comprise changes in their genomes that do not significantly affect encoded amino acid product. In one embodiment, the invention therefore provides an isolated or recombinant virus comprising a nucleic acid encoding an amino acid sequence as depicted in FIG. 20, Table 10, Table 11 and/or FIG. 3, or a functional part, derivative or analogue of the virus.

Additionally, a virus of the invention is provided comprising an amino acid sequence that differs to some extent to an amino acid sequence as depicted in FIG. 20, Table 10, Table 11 and/or FIG. 3. The amino acid sequence may be either naturally or artificially mutated. Conservative amino acid substitution may be applied: substitution of one or more amino acid residue(s) with another residue with generally similar properties (size, hydrophobicity, etc), such that the overall functioning is likely not to be seriously affected. Alternatively, mutations may be present that do affect at least one property of a virus of the invention. For instance, a certain desired characteristic may be artificially improved. However, mutations affecting functioning of a virus of the invention also occur in nature. In one embodiment, the amino acid sequence is more than 45 percent homologous to at least part of an amino acid sequence as depicted in FIG. 20, Table 10, Table 11 and/or FIG. 3. The part preferably comprises at least 20, more preferably at least 30, most preferably at least 50 amino acid residues.

Preferably, the amino acid sequence is at least (85 percent, more preferably 95 percent, most preferably 98 percent homologous to at least part of an amino acid sequence as depicted in FIG. 3. One embodiment of the invention thus provides an isolated or recombinant virus comprising an amino acid sequence which is more than 45% homologous to at least part of an amino acid sequence as depicted in FIG. 3, the part having at least 20, preferably at least 30, amino acid residues.

In one aspect, the invention provides an isolated or recombinant virus comprising an amino acid sequence which is more than 43% homologous to at least part of an amino acid sequence position 31-60 as depicted in FIG. 3, this part having at least 20, preferably at least 30, amino acid residues. In another aspect, the invention provides an isolated or recombinant virus comprising an amino acid sequence which is more than 80% homologous to at least part of an amino acid sequence position 91-150 as depicted in FIG. 3, the part having at least 20, preferably at least 30, amino acid residues. In yet another aspect, the invention provides an isolated or recombinant virus comprising an amino acid sequence which is more than 86% homologous to at least part of an amino acid sequence position 61-90 as depicted in FIG. 3, this part having at least 20, preferably at least 30, amino acid residues. In yet another aspect, the invention provides an isolated or recombinant virus comprising an amino acid sequence which is more than 90% homologous to at least part of an amino acid sequence position 1-30 as depicted in FIG. 3, the part having at least 20, preferably at least 30, amino acid residues.

In one aspect, a virus of the invention is provided comprising a nucleic acid sequence that differs to some extent to a nucleic acid sequence as depicted in FIG. 2B. As indicated before, RNA viruses are prone to mutations. Therefore, many EV79 strains exist in nature that differ to some extent from the strain obtained by the inventors. Such strains, comprising variations as compared to the sequence as depicted in FIG. 2B are, for instance, depicted in FIG. 4. Since these strains belong to the same EV79 species, they can be isolated, amplified and/or identified with a nucleic acid sequence based on a nucleic acid sequence as depicted in FIG. 2B.

A nucleic acid "based on" a sequence as depicted in FIG. 2B means herein that the nucleic acid may comprise the whole sequence, or an essential part of the sequence, which sequence may be modified to some extent. Preferably, the sequence is at least 45 percent homologous, more preferably 55 percent, more preferably 65 percent, even more preferably 75 percent, most preferably 90 percent homologous to a sequence as depicted in FIG. 2B.

The minimal size of the "essential part" of course varies with varying functions. If a part of a nucleic acid sequence is to be used as a primer, the minimal size preferably comprises about 5 nucleotides, more preferably about 8 nucleotides, even more preferably about 14 nucleotides, most preferably about 20 nucleotides. If a part of the nucleic acid sequence is to be used as a probe, the minimal size preferably comprises about 15 nucleotides, more preferably about 20 nucleotides.

An EV79 virus comprising mutations in its genome can as well be artificially made, for instance, to adapt codon usage to an expression system of choice or to attenuate the virus for vaccination purposes. Preferably, an isolated or recombinant virus is provided comprising a nucleic acid sequence that is at least 45% homologous to a nucleic acid sequence as depicted in FIG. 2B, or a functional part thereof. In one embodiment, a virus of the invention is provided comprising a nucleic acid sequence that is at least 55 percent, preferably at least 65 percent, more preferably at least 75 percent, more preferably at least 85 percent, even more preferably at least 95 percent, most preferably at least 98 percent, homologous to a nucleic acid sequence as depicted in FIG. 2B, or a functional part thereof. In yet another embodiment, an isolated or recombinant virus is provided comprising a nucleic acid sequence that is at least 45 percent, preferably at least 55 percent, more preferably at least 65 percent, more preferably at least 75 percent, more preferably at least 85 percent, even more preferably at least 95 percent, most preferably at least 98 percent homologous to at least part of a nucleic acid sequence as depicted in FIG. 2B, the part preferably having at least 30, more preferably at least 40, more preferably at least 50, most preferably at least 70 nucleotides.

In a preferred embodiment, an isolated or recombinant virus is provided comprising a nucleic acid sequence that is at least 45% homologous to at least part of a nucleic acid sequence position 500 to 1134 as depicted in FIGS. 2A and 2B, the part preferably having at least 30, more preferably at least 40, more preferably at least 50, most preferably at least 70 nucleotides. More preferably, the nucleic acid sequence is at least 45% homologous to at least part of a nucleic acid sequence position 500 to 1748 as depicted in FIGS. 2A and 2B, the part having at least 30, more preferably at least 40, more preferably at least 50, most preferably at least 70 nucleotides. In a more preferred embodiment, an isolated or recombinant virus is provided comprising a nucleic acid sequence that is at least 45% homologous to at least part of a nucleic acid sequence position 683 to 1134 as depicted in FIG. 2B, the part having at least 30, more preferably at least 40, more preferably at least 50, most preferably at least 70 nucleotides. In yet another preferred embodiment, the nucleic acid sequence is at least 45% homologous to at least part of a nucleic acid sequence position 683 to 1748 as depicted in FIG. 2B, the part having at least 30, more preferably at least 40, more preferably at least 50, most preferably at least 70 nucleotides.

The invention also provides an isolated or recombinant virus comprising a nucleic acid sequence which is more than 42% homologous to at least part of a nucleic acid sequence position 651-700 as depicted in FIGS. 2A and 2B, the part having at least 20, preferably at least 30, more preferably at least 40, most preferably at least 50 nucleotides.

In another aspect, the invention provides an isolated or recombinant virus comprising a nucleic acid sequence which is more than 58% homologous to at least part of a nucleic acid sequence position 701-750 as depicted in FIG. 2B, the part having at least 20, preferably at least 30, more preferably at least 40, most preferably at least 50 nucleotides.

In yet another aspect, the invention provides an isolated or recombinant virus comprising a nucleic acid sequence which is more than 88% homologous to at least part of a nucleic acid sequence position 751-800 as depicted in FIG. 2B, the part having at least 20, preferably at least 30, more preferably at least 40, most preferably at least 50 nucleotides.

In another aspect, the invention provides an isolated or recombinant virus comprising a nucleic acid sequence which is more than 72% homologous to at least part of a nucleic acid sequence position 801-850 as depicted in FIG. 2B, the part having at least 20, preferably at least 30, more preferably at least 40, most preferably at least 50 nucleotides.

In another aspect, the invention provides an isolated or recombinant virus comprising a nucleic acid sequence which is more than 54% homologous to at least part of a nucleic acid sequence position 901-950 as depicted in FIG. 2B, the part having at least 20, preferably at least 30, more preferably at least 40, most preferably at least 50 nucleotides.

In another aspect, the invention provides an isolated or recombinant virus comprising a nucleic acid sequence which is more than 64% homologous to at least part of a nucleic acid sequence position 951-1000 as depicted in FIG. 2B, the part having at least 20, preferably at least 30, more preferably at least 40, most preferably at least 50 nucleotides.

In another in another aspect, the invention provides an isolated or recombinant virus comprising a nucleic acid sequence which is more than 48% homologous to at least part of a nucleic acid sequence position 1001-1050 as depicted in FIG. 2B, the part having at least 20, preferably at least 30, more preferably at least 40, most preferably at least 50 nucleotides.

In another aspect, the invention provides an isolated or recombinant virus comprising a nucleic acid sequence which is more than 56% homologous to at least part of a nucleic acid sequence position 1051-1100 as depicted in FIG. 2B, the part having at least 20, preferably at least 30, more preferably at least 40, most preferably at least 50 nucleotides.

In another aspect, the invention provides an isolated or recombinant virus comprising a nucleic acid sequence which is more than 53% homologous to at least part of a nucleic acid sequence position 1101-1134 as depicted in FIG. 2B, the part having at least 20, preferably at least 30, more preferably at least 40, most preferably at least 50 nucleotides.

With the teaching of the present invention it has become possible to ascribe "general" symptoms such as, for instance, diarrhea to an EV79-related disease. Hence, an EV79-related disease can now be diagnosed, for instance, by demonstrating the presence of EV79 virus, or antibodies against the virus, in a sample.

Now that a virus of the invention has been provided, a person skilled in the art is well capable of generating a functional part, derivative or analogue of the virus. A functional part of an EV79 virus is defined as a part that has the same EV79-specific properties in kind, although not necessarily in amount. Which properties need to be compared depends from a particular application. For instance, if the EV79 infection properties are concerned, a property to infect a cell should be considered, in which case a functional part of EV79 should also be capable of infecting a cell, eventually to a different extent. If however a capability of inducing an immune response in a host is considered, a single EV79-specific epitope of an EV79 virus can be considered to be a functional part.

A functional derivative of a virus is defined as a viral compound, which has been altered such that the properties of the compound are essentially the same in kind, but not necessarily in amount. A derivative can be provided in many ways, for instance, through nucleotide substitution (preferably "wobble" based), through (conservative) amino acid substitution, subsequent modification, etc.

Analogous compounds of a virus can also be generated using methods in the art. For instance, a chimeric virus can be produced, or an EV79 virus with a chimeric protein. For instance, EV79 can be rendered more immunogenic by generating a cell surface associated fusion protein comprising at least part of an EV79 cell surface protein and a non-EV79 immunogenic part. EV79 virus comprising such chimeric protein can be used for inducing an enhanced immune response in a host, for instance, for vaccination purposes.

As used herein, the term "a virus of the invention" is meant to also comprise a functional part, derivative and/or analogue of the virus.

A functional part of a protein is defined as a part that has the same kind of properties in kind, but not necessarily in amount. The properties may comprise immunogenic properties. By immunogenic properties is meant the capability to induce an immune response in a host. A functional derivative of a protein is defined as a protein, which has been altered such that the properties of the molecule are essentially the same in kind, but not necessarily in amount. A derivative can be provided in many ways, for instance, through conservative amino acid substitution.

A person skilled in the art is well able to generate analogous compounds of a protein. This can, for instance, be done through screening of a peptide library. Such an analogue has essentially the same properties of the protein in kind, but not necessarily in amount.

Now that an EV79 virus is provided, primers and/or probes capable of specifically hybridizing to a nucleic acid of a virus of the invention can be generated. By "specifically hybridizing" is meant herein that the primer and/or probe is capable of hybridizing to the nucleic acid because the primer and/or probe comprises a sequence of at least 3, preferably at least 5, nucleotides that is complementary to the nucleic acid of the virus. In a preferred embodiment, the primer and/or probe consists of a sequence that is complementary to the nucleic acid of the virus. Preferably, the primer and/or probe is capable of hybridizing with a nucleic acid of a virus of the invention under stringent conditions. A primer/probe of the invention is particularly suitable for amplifying/detecting at least part of the genome of an EV79 virus.

One embodiment provides a primer and/or probe capable of specifically hybridizing to a nucleic acid sequence as depicted in FIG. 2B. In Table 2, sequences of primers of the invention are provided.

The invention also provides an isolated molecule capable of specifically binding a virus or functional part, derivative and/or analogue of the invention. The isolated molecule preferably comprises a proteinaceous molecule. The molecule may be capable of specifically binding a nucleic acid of the virus, such as at least part of a sequence as depicted in FIG. 2B. The molecule is however preferably capable of specifically binding an amino acid sequence of the virus. The amino acid sequence may be located inside an EV79 virus particle, either partly or entirely. However, the amino acid sequence preferably comprises (part of) a protein associated with the surface of the virus, such as an epitope. By "associated with the surface" is meant a protein that is at least partly exposed to the surface of the virus. Such protein, for instance, comprises a viral capsid protein. In one embodiment, the amino acid sequence comprises at least part of an amino acid sequence as shown in FIG. 3. The part preferably comprises at least 5, more preferably at least 10 amino acid residues.

By a molecule capable of specifically binding a nucleic acid sequence is meant herein a molecule that is capable of distinguishing between related nucleic acid sequences under stringent conditions. A molecule capable of specifically binding a proteinaceous molecule is defined as a molecule that is capable of distinguishing between different proteinaceous molecules because it has more affinity for a specific amino acid sequence, a specific conformation of the proteinaceous molecule, etc. Non-specific "sticking" of a molecule is not considered specific binding.

A molecule of the invention preferably comprises an antibody or a functional part, derivative and/or analogue thereof. A functional part of an antibody has essentially the same properties of the antibody in kind, but not necessarily in amount. The functional part is preferably capable of specifically binding an antigen of EV79. However, the functional part may bind such antigen to a different extent as compared to the whole antibody. A functional part or derivative of an antibody, for instance, comprises a FAB fragment or a single chain antibody. An analogue of an antibody, for instance, comprises a chimeric antibody. As used herein, the term "antibody" is also meant to comprise a functional part, derivative and/or analogue of the antibody.

A molecule capable of specifically binding an EV79 virus can be obtained using current methods in the art. For instance, an EV79-directed antibody may be obtained from an infected individual. The antibody can, for instance, be isolated from a sample, such as, for instance, a blood, serum, sputum, saliva or tissue sample, obtained from the infected individual. Alternatively, a non-human animal can be inoculated with EV79 in order to induce an immune response. Produced antibodies can subsequently be collected from the animal. Collected antibodies often need to be purified, for instance, by affinity chromatography.

Furthermore, the antibody can be recombinantly produced, for instance, by micro-organisms, cell lines (i.e., monoclonal antibodies) or transgenic animals. In that case, codon optimization may be required. An EV79-directed antibody may as well be synthesized using common techniques such as solid phase synthesis.

Once a molecule of the invention is obtained, a desired property, such as its binding capacity, can be improved. For proteinaceous molecules this can, for instance, be done by an Ala-scan and/or replacement net mapping method. With these methods, many different proteinaceous molecules are generated, based on an original amino acid sequence but each molecule containing a substitution of at least one amino acid residue. The amino acid residue may either be replaced by Alanine (Ala-scan) or by any other amino acid residue (replacement net mapping). Each variant is subsequently screened for the desired property. Generated data are used to design an improved proteinaceous molecule.

Once a molecule of the invention, such as an antibody capable of specifically binding Prima-7, has been obtained, it may be necessary to test for EV79 specificity, because antibodies may cross react with other enteroviruses if they are directed against a conserved region of enteroviral species region. Specificity can, for instance, be tested by coating wells with the molecules, subsequently incubating the wells with different enteroviral species, and determining whether the molecules appear to specifically bind EV79 only, to a significant extent. Of course many alternative methods for testing specificity are available in the art. In one aspect, the invention thus provides a method for producing a molecule capable of specifically binding a virus or functional part, derivative or analogue of the invention comprising:

producing molecules capable of binding a virus or functional part, derivative or analogue of the invention, and selecting a molecule that is specific for the virus.

An antibody or functional part, derivative and/or analogue of the invention can be used to detect the presence of an EV79 virus in a sample. The sample may comprise a blood, serum, or tissue sample. Preferably, however, the sample comprises a feces, sputum or saliva sample. The antibody or functional part, derivative and/or analogue can, for instance, be used in an affinity column. The antibody or functional part, derivative and/or analogue may as well be coated on ELISA microtiter plates, after which the plate can be incubated with a sample from a human or non-human animal. If the antibody appears to specifically bind to some component of the sample, it is indicative for the presence of EV79 in the sample. Binding of an EV79 component can, for instance, be demonstrated by a second, labeled, antibody directed against EV79.

As an alternative for ELISA, optical biosensors (e.g., BiaCore 3000 or the Affinity Sensors IAsys) can be used to detect the interaction of EV79 encoded proteins and a ligand (e.g., antibody or Fab). These optical systems are equally sensitive as an ELISA but allow detection in real-time.

A typical biosensor experimental cycle is illustrated in FIG. 7. The first step is usually the immobilization of a given ligand and a control to the biosensor cuvette surface. Several surfaces are commercially available, which include, for instance, biotin, carboxylate, hydrophobic and amine surface types. The next step can be the addition of a sample wherein the operator would like to study the interaction of a specific ligate to the immobilized ligand. This step is termed the binding step. Buffer can then be added to dissociate any weakly and non-specific bound molecules. A fourth step may be a regeneration step, whereby the surface is brought back to its original state. After regeneration, the cuvette can either be re-used for another binding experiment or stored usually at 4° C.[7,27]).

A molecule of the invention is suitable for isolating EV79 present in a sample. The sample preferably comprises a feces sample from an individual suffering from diarrhea. A high throughput automated assay can be established wherein test samples are incubated with a molecule of the invention. Bound virus can, for instance, be detected and/or identified by staining of virus particles or detection of EV79 nucleic acid using a primer and/or probe of the invention. Such assay provides for easy and fast diagnosis. Moreover, different strains of EV79 can be obtained. The strains may be purified, after which they can be further investigated, for instance, in order to improve diagnostic protocols. In one aspect, the invention thus provides an isolated or recombinant virus that is immunoreactive with a (preferably proteinaceous) molecule of the invention capable of specifically binding EV79.

A primer and/or probe of the invention can also be used for detection and/or identification of a virus of the invention. After nucleic acid isolation, for instance, with the Boom method, a PCR reaction can be set up using at least one primer of the invention. In one embodiment, one (specific) primer of the invention is used in combination of one "universal" primer. In another embodiment, two specific primers of the invention are used. Subsequently, a probe of the invention can be used in order to determine whether amplified EV79 viral product is obtained. Alternatively, a nucleic acid of a virus of the invention can be used for detecting the presence of nucleic acid capable of hybridizing therewith. In one embodiment, the nucleic acid comprises a sequence as depicted in FIG. 2B. It will be acknowledged that an antisense strand should be used in order to detect a sense EV79 nucleic acid by way of hybridization.

It has become possible to detect a virus of the invention in a sample, for instance, using a molecule, primer and/or probe of the invention. Alternatively, it is possible to screen a sample for the presence of a molecule capable of specifically binding a virus of the invention, such as a specific ligand or an antibody directed against a virus of the invention. This is often desirable for diagnostic purposes because after viral infection of an individual, immunopathogenesis often changes over time. During the first stage an initial immune response of the cell mediated type is often invoked, which may switch into humoral responses over time. Because of the change, one kind of immunological diagnostic procedure may not be suitable for the whole period of infection. Alternating positive and negative results may be obtained.

Therefore, in addition to measuring the presence of EV79 virus, it is advantageous to determine the presence of antibodies against the virus in a sample of an individual as well. This can be performed by incubating a sample of the individual with a virus of the invention (or functional part, derivative and/or analogue thereof) and detecting bound antibodies using common methods in the art. A use of a virus or functional part, derivative and/or analogue of the invention for detecting a molecule capable of specifically binding a virus of the invention, such as a specific ligand or an antibody against the virus, in a sample is therefore also herewith provided. Of course, it is not necessary to use whole virus particles since a nucleic acid sequence and/or an amino acid sequence of the virus can also be used to detect antibodies. The amino acid sequence preferably comprises an epitope of a surface-associated protein of a virus of the invention, because an individual's immune system is directly exposed to such surface-associated proteins after viral infection. Therefore, antibodies against the surface-associated proteins are most likely to be present. In one embodiment, a sequence as depicted in FIG. 3 or a functional part, derivative or analogue thereof is used for detecting a molecule capable of specifically binding a virus of the invention, such as a specific ligand or an antibody against a virus of the invention.

A virus of the invention, or a functional part, derivative or analogue thereof, is particularly suitable for use as a vaccine, preferably against an EV79-related disease. In a preferred embodiment, an attenuated virus or a functional part such as a surface associated protein, an epitope thereof or a glycosylation bond is used. The vaccine preferably comprises a suitable adjuvant such as, for instance, Specol or a double oil emulsion. The virus or functional part may furthermore be coupled to a suitable carrier, such as keyhole limpet hemocyanin (KLH) or an immunogenic conjugate of a protein such as ovalbumin. Methods for generating a vaccine are known in the art. Since an EV79 virus of the invention is an enterovirus, a vaccine against EV79 may be generated by analogy with currently used vaccines against other enteroviruses, such as poliovirus. Methods for production of vaccines known to persons skilled in the art encompass, for instance, dead virus, live attenuated virus, viral subunits, DNA vaccines, DNA vaccines in suitable vaccine vectors like adenovirus or AAV and gene therapy approaches through integrating viral vectors. Administration of such vaccine to an individual provides protection against EV79 by way of activation of the individual's immune system.

A virus of the invention, or functional part, derivative and/or analogue thereof, is also suitable for use as a medicament. For instance, the virus may be provided with a nucleic acid encoding a proteinaceous molecule with beneficial properties for local treatment of the gastrointestinal tract.

In another embodiment, a molecule of the invention, preferably a proteinaceous molecule of the invention, is used as a vaccine or medicament. The vaccine or medicament is preferably used for protection and/or treatment of an EV79-related disease. The molecule can be administered to an individual, preferably in combination with a suitable adjuvant and/or carrier as described above, before an EV79 infection has taken place. Such passive immunization provides (often temporary) protection against subsequent infection. The molecule may also be administered as a medicament after an EV79 infection. The molecule, capable of specifically binding EV79, will at least in part counteract EV79 infection. A medicament comprising a molecule of the invention can of course be combined with one or more other medicaments, such as inflammation inhibitors. In one embodiment, several medicaments are separately administered to an individual. However, a molecule of the invention can also be combined with another pharmaceutically active compound in one pharmaceutical preparation.

The invention thus provides a vaccine comprising a virus or functional part, derivative or analogue and/or a molecule of the invention.

A medicament comprising a molecule of the invention is also herewith provided. The medicament preferably comprises a proteinaceous molecule of the invention. A vaccine or medicament of the invention is preferably used for at least in part preventing and/or treating an EV79-related disease.

Enteroviruses often induce symptoms, such as diarrhea, respiratory problems and fever that are involved with many kinds of diseases. Hence, these symptoms cannot directly be ascribed to an enteroviral infection. Now that a virus of the invention is provided, it has become possible to determine whether an individual suffers from an enteroviral genus-related disease. More specifically, it can be determined whether an EV79-related disease is involved. A virus or functional part, derivative or analogue of the invention can be used to determine whether a sample from an individual comprises antibodies against the enterovirus. Moreover, the presence of enterovirus in a sample can be determined using a proteinaceous molecule of the invention, for instance, using affinity chromatography or ELISA. The presence of enterovirus in a sample can as well be determined by subjecting nucleic acid of the sample to an amplification reaction such as PCR, RT-PCR, TMA or NASBA and determining whether amplified enteroviral nucleic acid is present, using at least one primer or probe of the invention. Once an enteroviral genus-related disease has been diagnosed, it is possible to provide adequate treatment, such as, for instance, antibodies specifically directed against the enterovirus. Alternatively, or in addition, general antiviral medicaments may be used.

A use of a virus, molecule and/or a primer/probe of the invention for diagnosis of an enteroviral genus-related disease is, therefore, also provided. Preferably, the enteroviral genus comprises an EV79 enterovirus.

The invention also provides a diagnostic kit comprising a virus or functional part, derivative or analogue, and/or a primer/probe of the invention. With a kit of the invention, an enterovirus-related disease can be diagnosed, for instance, by way of demonstrating the presence of enterovirus, or enterovirus-directed antibodies, in a sample. In one embodiment, the kit also comprises suitable means for nucleic acid isolation and/or amplification.

A diagnostic kit comprising a molecule, preferably a proteinaceous molecule, of the invention capable of specifically binding EV79 is also herewith provided. The molecule is preferably present on a suitable solid support, such as a microtiter plate. The kit, particularly suitable for demonstrating the presence of enterovirus in a sample, preferably comprises suitable means for staining enterovirus as well. Such means are commonly available in the art.

In one aspect, the invention provides a method for determining whether an individual suffers from an EV79-related disease, comprising obtaining a sample from the individual and detecting an EV79 virus or functional part, derivative or analogue thereof in the sample by hybridizing and/or amplifying a nucleic acid of the virus or functional part, derivative or analogue with a primer and/or probe of the invention and detecting hybridized and/or amplified product.

In another aspect, the invention provides a method for determining whether an individual suffers from an EV79-related disease, comprising obtaining a sample from the individual and detecting an EV79 virus or functional part, derivative or analogue thereof in the sample by specifically binding of the virus or functional part, derivative or analogue with a (proteinaceous) molecule of the invention and detecting bound product.

In yet another aspect, the invention provides a method for determining whether an individual suffers from an EV79-related disease, comprising obtaining a sample from the individual and detecting EV79-specific antibodies in the sample by specifically binding the antibodies with an EV79 virus or functional part, derivative or analogue of the invention and detecting bound product.

Once an EV79-related disease has been diagnosed, it can be treated with a medicament of the invention. Additionally, an individual at risk of obtaining an EV79 infection can be vaccinated with a vaccine of the invention in order to prevent an EV79-related disease. For instance, immunocompromised individuals can be provided with a vaccine comprising molecules of the invention capable of specifically binding EV79 virus.

A method for treating an individual suffering from, or at risk of suffering from, an EV79-related disease, comprising administering to the individual a vaccine or medicament of the invention is therefore also provided.

The invention is further illustrated by the following examples. The examples do not limit the scope of the invention in any way.

BRIEF DESCRIPTION OF THE SEVERAL VIEWS OF THE DRAWINGS

In the drawings, which illustrate what is currently considered to be the best mode for carrying out the invention:

Figure 1:
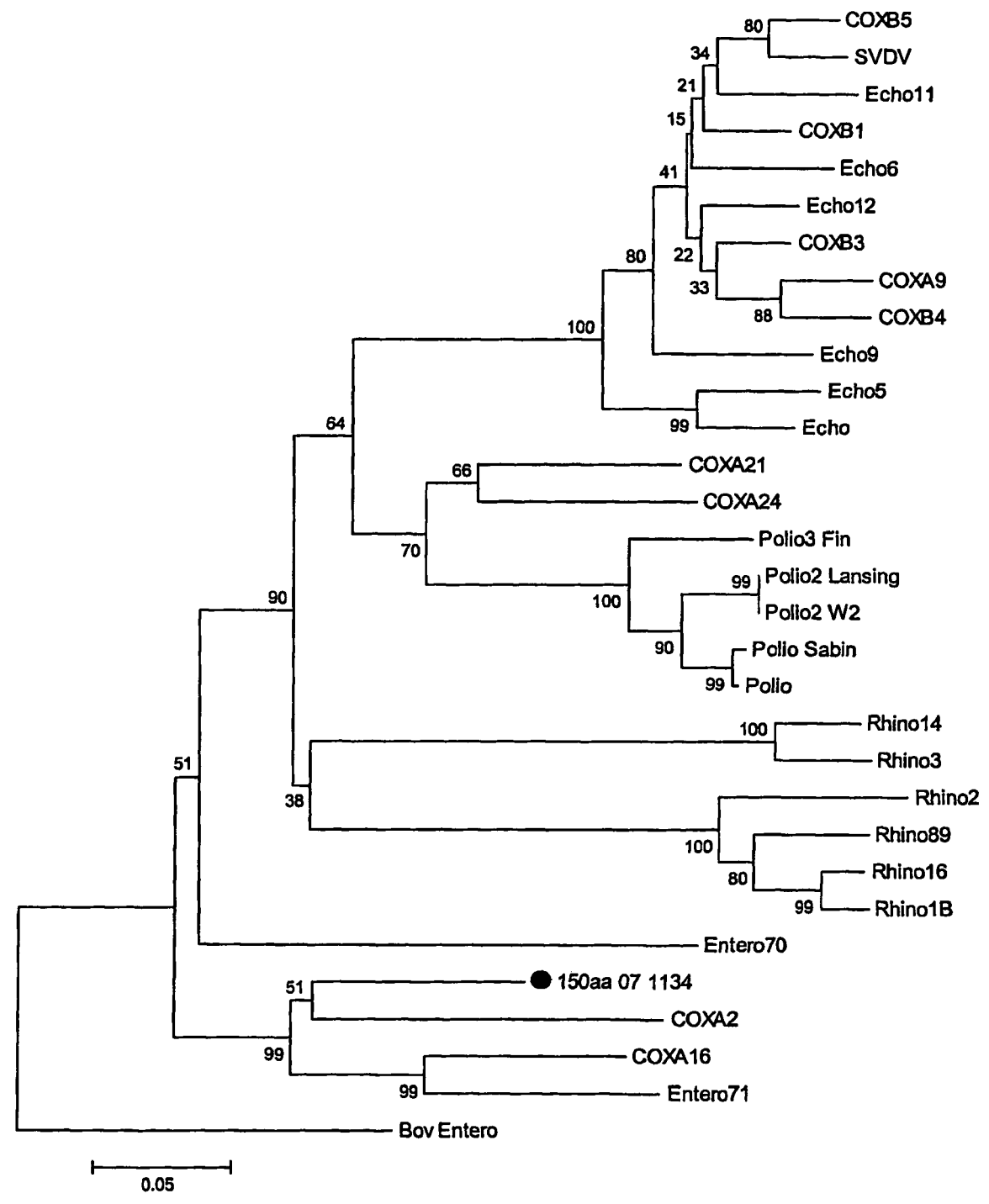

FIG. 1: The NJ tree of phylogenetic analysis based on the 150 aa peptide sequence of EV79. Distance: p-distance; bootstrap test: 500.

FIG. 2A: 5'-UTR region of EV79 (SEQ ID NO:61).

FIG. 2B: VP4 and VP2 region of EV79 (SEQ ID NO:61).

FIG. 3: Amino acid sequence of VP4 and VP2 region translated from EV79 (SEQ ID NO:63).

FIG. 4: Screening feces samples with specific RT-PCR, alignment of PCR product of strain 07-1787 (SEQ ID NO:64), PCR product of strain F26kol03 (SEQ ID NO:65), PCR product of strain F26kol06 (SEQ ID NO:66), PCR product of strain F26kol10 (SEQ ID NO:67), PCR product of strain F27kol20 (SEQ ID NO:68), PCR product of strain F27kol21 (SEQ ID NO:69), PCR product of strain F35kol32 (SEQ ID NO:70), and PCR product of strain F35kol36 (SEQ ID NO:71) are shown.

FIG. 6: Nucleic acid and amino acid sequence homology between EV79 and human enterovirus.

FIG. 8: The Enterovirus Prima 7 genome comprises 7.419 KB and exhibits the typical organization of a positive sense single stranded RNA virus. Depicted is a cDNA derivative of the genomic RNA with added restriction sites. The genome posses a single open reading (ORF) of 2193 amino acids (AA), flanked by 5' and 3' untranslated regions (UTR). Within the deduced amino acid sequence of the ORF, domains encoding capsid proteins VP1 to 4, proteases 2a and 3C, a helicase (2C), a RNA dependant polymerase (POL) and non-structural proteins 2b and 3A, were identified on the basis of homology. Between 3A and protease 3C, domain 3B encoding a 22 AA VPg that is covalently attached to the 5' end of the genomic RNA. Predicted 2a and 3C proteolytic cleavage sites separate all these domains, except VP4 and VP2. The cleavage between these two domains is predicted to occur autocatalyticly.[2]

FIG. 9: The similarity of the GenBank reference sequences for Coxsackie A16 (NC_001612) human enterovirus A, Coxsackie B1 (NC_001472) human enterovirus B, Coxsackie A21 (NC_001428) human enterovirus C, Enterovirus 70 (NC_001430) human enterovirus D, Plaque A2 virus (NC_003988) human enterovirus E and Enterovirus 71 (AF302996) to PRIMA 7 was determined in a window of 200 nt sliding along the Prima 7 genome in steps on 20 nt and plotted against its position in Prima 7.

FIG. 10: A similar analysis was performed with an alignment all available full-length genome sequences of group A human enteroviruses. Coxsackie A16 Cox (NC_001612), Coxsackie A16 (CAU05876), Coxsackie A16 (AF177911), Enterovirus 71 strain TW/2272198 (AF119795), Enterovirus71 (AF302996), Enterovirus 5666/sin/002209 (AF352027), and Enterovirus 71 (ETU22522). It is clear from this plot that even in a comparison of the most closely related group A enteroviruses, EV79 exhibits the low sequence identity throughout its genome.

FIG. 11: The first chimeric genome (FIG. 11) was generated by a reciprocal recombination in the VP3, fusing nucleotide 2187 of Coxsackie virus A16 (NC_001612) to nucleotide 2129 of EV79. Recombination occurred at the conserved sequence TGGGA, retaining the large open reading frame and generating a hybrid polyprotein. The Coxsackie A16 derived A16-derived part is indicated with a single line, whereas the EV79 derived EV79-derived part is indicated with grey boxes. Below is depicted the recombination site with the Coxsackie part in bold capitals and the EV79 derived EV79-derived part is underlined. ACTGCAATGCTGGGAACCCATGTGATA TGGGATTTTGGTTTACAATCATC (SEQ ID NO:72)

FIG. 12: A second chimeric genome was generated by an imaginary reciprocal recombination fusing nucleotide 3773 of Enterovirus 71 (U22522) to nucleotide 3713 of EV79 again creating a hybrid 2b-encoding domain within polyprotein. Recombination could occur within the conserved sequence ATGGA. The Enterovirus 71 derived 71-derived part is indicated by a single line and the EV79 derived EV79-derived part is indicated by grey boxes. Below is depicted the crossover site where the EV71 sequences are in bold print and the EV79 sequences are underlined. TCTTATGGTTAGATGAAGAAGCC ATGGAACAGGGGGTCACGGATTACATC (SEQ ID NO:73)

FIG. 13: Hybrid 1 is the result of a crossover between Coxsackie A16 (NC_001612) and EV79. Hybrid 2 is a chimera of Enterovirus 71 (U022522) and EV79. The actual recombination sites can be deduced from the SimPlot graph.

FIG. 14: The predicted secondary structure of nucleotides 1 and 752 (ATG). Five major stem loops are predicted of which nucleotides 456 to 564 correspond to Poliovirus loop V. This particular stem loop confers to Poliovirus the ability to translate efficiency in neuronal cells. This region folds in slightly different secondary structures, differing slightly in enthalpy. Obviously, the presence of RNA-binding proteins could stabilize certain secondary structures in a manner Mfold is unable to predict.

FIG. 15: The strongest sequence conservation is encountered in the 5'-untranslated region (5'-UTR), probably because this region plays a pivotal role in the replication and initiation of protein synthesis.[22] Inverted repeats in the 5'-UTR allow extensive internal base pairing and the resulting secondary structure can be predicted using the M-Fold program.[14] The putative initiation codon resides immediately downstream of a CT rich tract (position 643-660) which is part of a putative Internal Ribosome Entry Site (IRES) or ribosome landing pad. This ATG corresponds to the one we identified as initiation codon on the basis of homology. All seven other ATGs preceding the putative initiation codon are out of frame and, according to the M-fold prediction, sequestered in hairpin loops. The region encompassing the fifth stem-loop in the 5'-UTRs from Poliovinises 1 (AY056702), 2 (D00625), 3 (AJ29398), Enterovirus 70 (D00820), Enterovirus 71 (U022521), Coxsackie A16 (U05876), Coxsackie A21 (D00538) and Enterovirus 79 were aligned with ClustalW. Specific mutations in the stem-loop V (indicated in bold print above the alignment) of polioviruses, preventing proper base pairing in the stem-loop, reduce transcription[20] and decrease neurovirulence.[10] Such attenuated polio strains are used for vaccine production. The implicated nucleotides (marker in yellow) have been conserved in EV79, hence could also be used to create attenuated strains. Alignment of 5'-UTR sequence of human enterovirus D00538CXA21 (SEQ ID NO:74), 5'-UTR sequence of human enterovirus D00820EV70 (SEQ ID NO:75), 5'-UTR sequence of human enterovirus D00625PV2 (SEQ ID NO:76), 5'-UTR sequence of human enterovirus AJ293918PV3 (SEQ ID NO:77), 5'-UTR sequence of human enterovirus U05876CXA16 (SEQ ID NO:78), 5'-UTR sequence of human enterovirus U22521EN71 (SEQ ID NO: 79), 5'-UTR sequence of human enterovirus AY056702PV1 (SEQ ID NO:80), and 5'-UTR sequence of human EV79 (SEQ ID NO:81) are shown.

FIG. 17: The deduced amino acid sequences of Coxsackie A16 (NP_0042242 and AAD55085), Coxsackie B1 (NP_040958), Coxsackie A21 (NP_040759), Coxsackie B6 (Q9QL88), Plaque A2 (NP_653149), Polio 1 (AAM09804), Enterovirus 70 (NP_040760), Enterovirus 5666 (AAB30618) and Enterovirus 5865 (AAK13008) were aligned with ClustalW. The local protein similarity to EV79 to the group A enteroviruses varies from 61 to 92%.

FIG. 18: Sequences were aligned using Clustal-W included in the Vector NTI suite 7 software package (Infor-Max, Bethesda, U.S.A.). Phylogenetic analyses were performed by the Neighbor-Joining (NJ) method, as implemented in the MEGA 2.1 software package.[12] Kimura's 2-parameter distances[11] were estimated for the nucleotide sequences, and P-distances were used for amino acid sequences. Five hundred bootstrap replicates were analyzed. The distance data deduced from the polyprotein alignment was used to construct a phylogenetic tree. Bootstrap values are indicated at the nodes. The distance bar indicates 5% sequence divergence.

FIG. 19: Prima 7 (EV79) nucleotide sequence (SEQ ID NO:82).

FIG. 20: Deduced amino acid sequence EV79 (SEQ ID NO:83).

FIG. 21: Restriction maps of pLXRN and its derivative pEV79.

DETAILED DESCRIPTION OF THE INVENTION

Examples

Isolation of Prima 7

Figure 5:
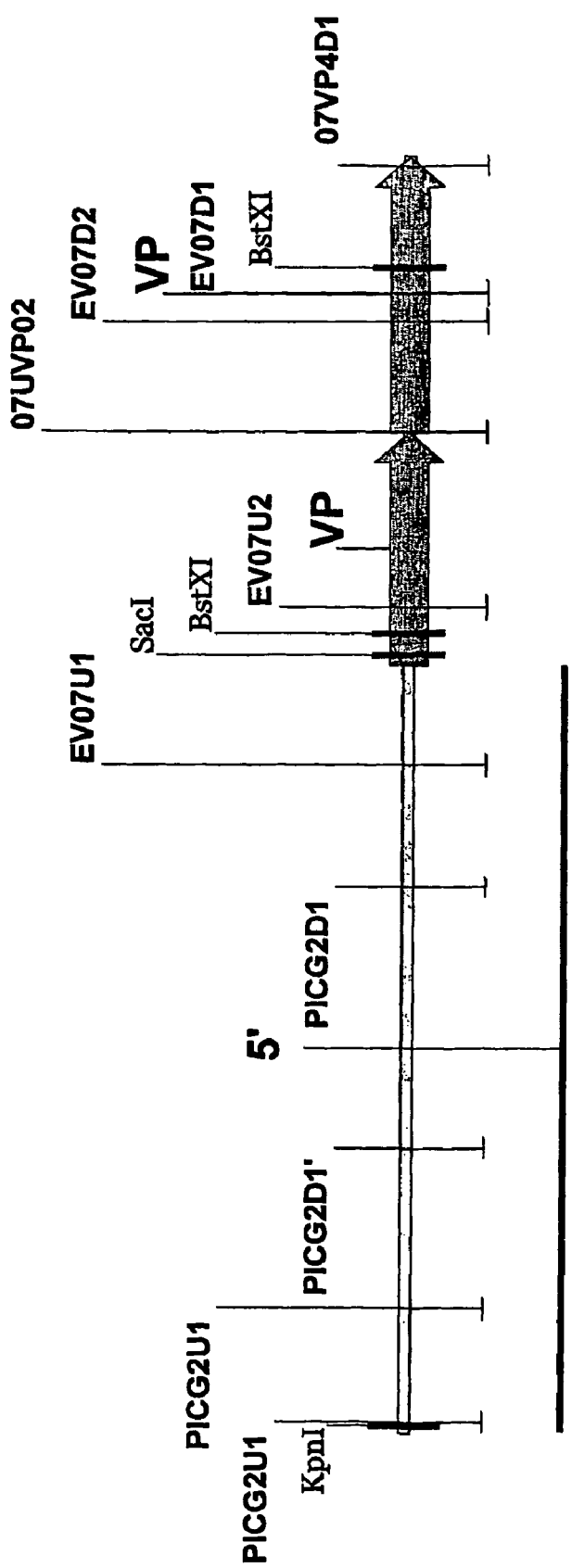
FIG. 5: Restriction map of partial Prima 7 genome showing the location of the oligonucleotides and the open reading frame.
Figure 7:
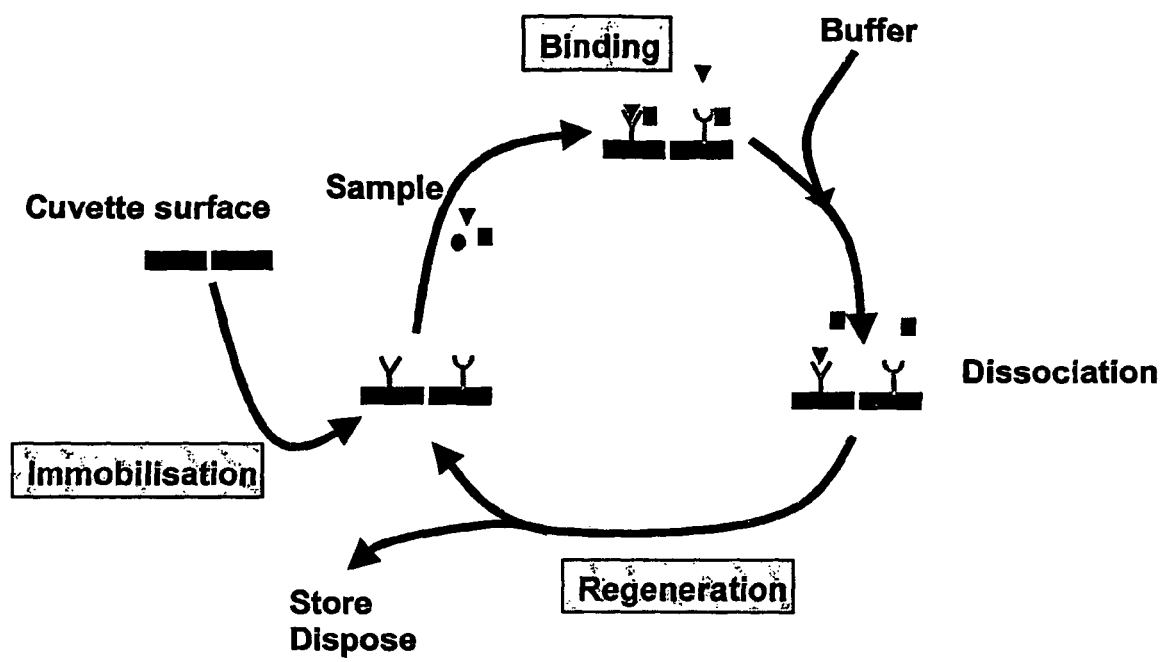
FIG. 7: Biosensor experimental cycle.
Figure 16:
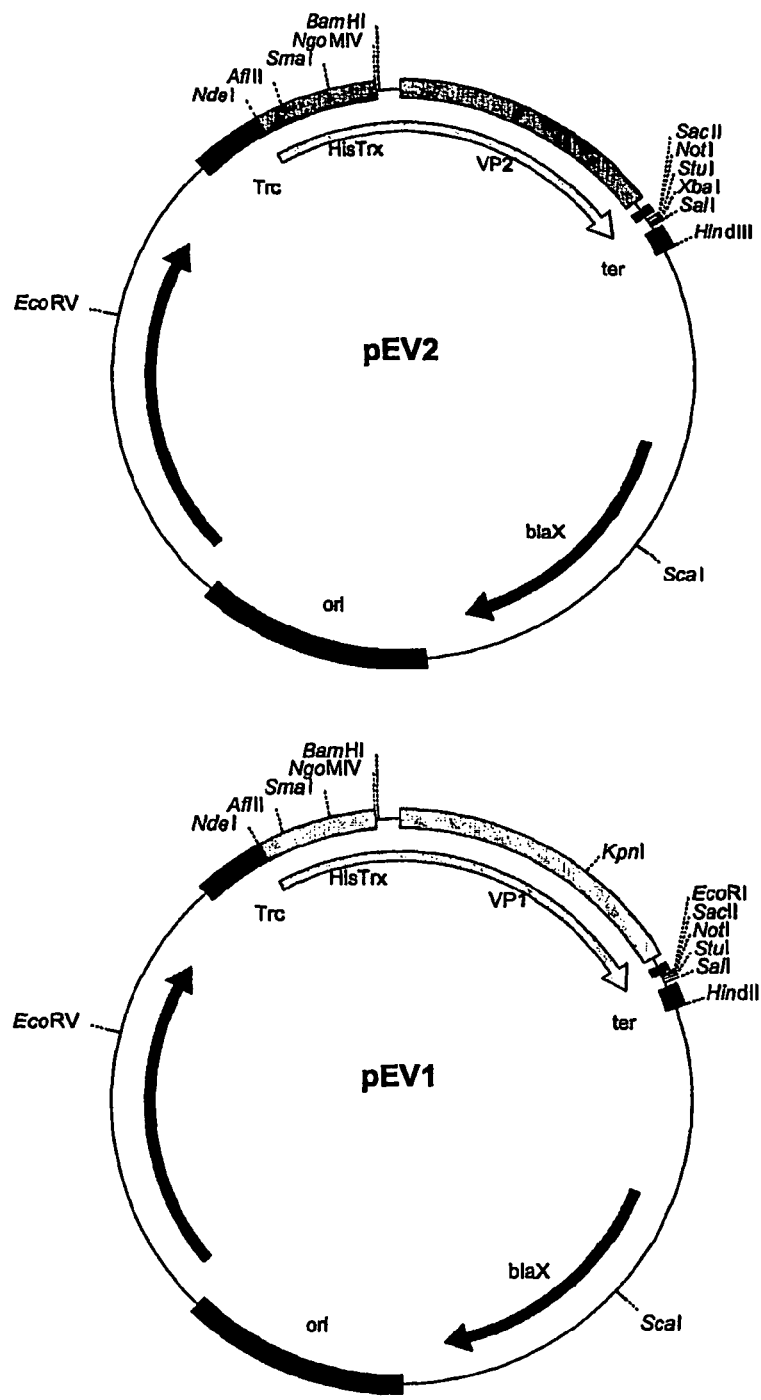
FIG. 16: Upon introduction into a suitable *E. coli* host, production of a HisTrx-StrepII bearing VP1 or VP2 fusion protein can be induced by addition of IPTG to the culture medium. After cell lysis, the expressed proteins can be detected and purified with the appropriate affinity matrices by virtue of their His, Thioredoxin and StrepII affinity tags.
Figure 22:
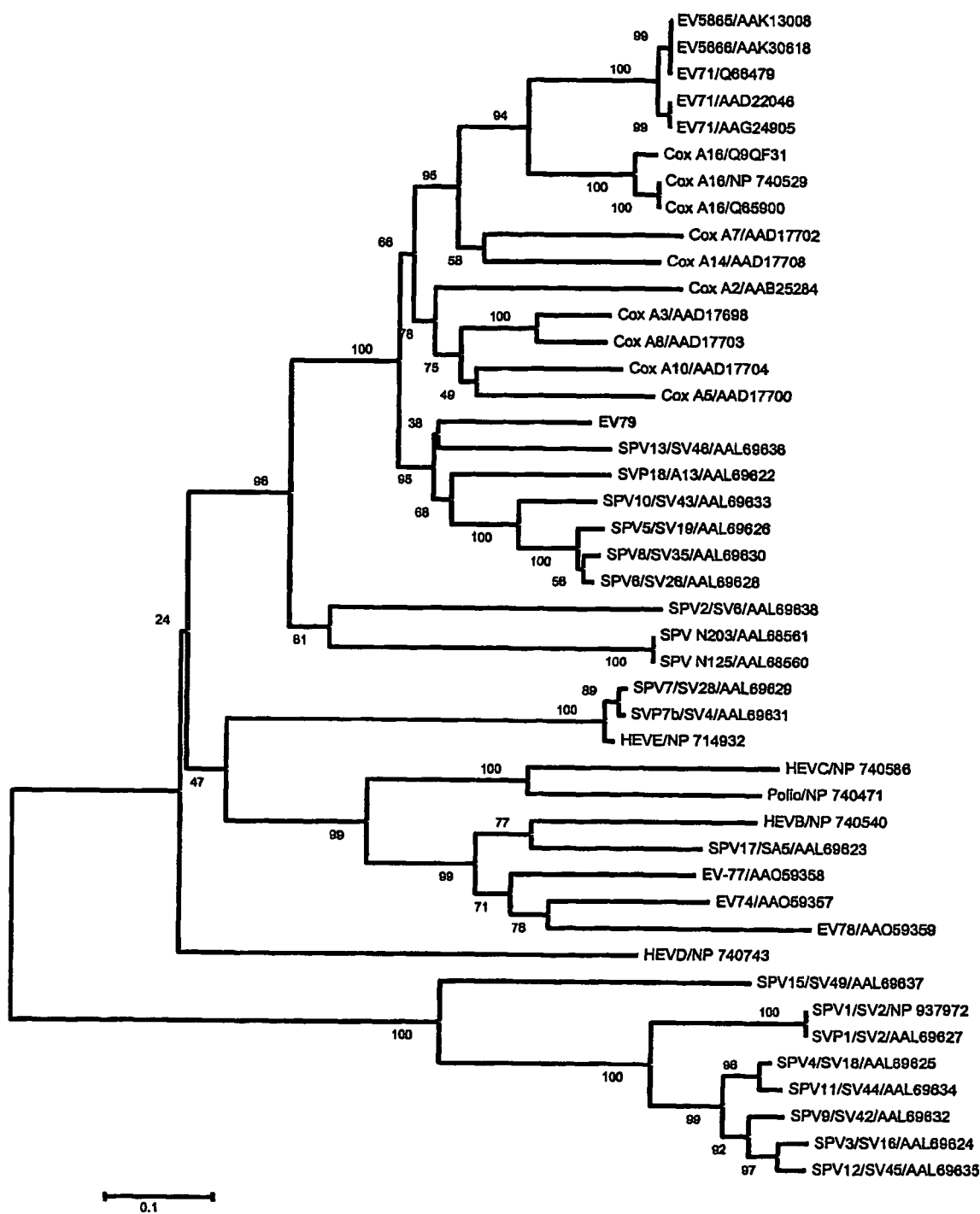
FIG. 22: VP1 orthologs were retrieved from Genbank, aligned using ClustalX and the corresponding phylogenetic tree was constructed with Mega 2.1. The protein accession numbers are indicated following the species name. Several representatives of Enterovirus 71 (EV71) and Coxsackie A16 (Cox A16) were used to account for the intra-species sequence variation. To facilitate correlation with serological data additional Group A human enterovirus VP1 (Cox A2, A3, A5 A8, A10 and A14) were added. For the Human Enteroviruses (HEV) A, B, C, D and E the reference genomes were used (worldwideweb.ncbi.nlm.nih.gov/genomes/VI-RUSES/10239.html). Clusters in VP1 derived VP1-derived phylogenetic trees have been demonstrated to correlate with serotype clusters. These serotype clusters correspond to currently recognized enteroviral species. In the VP1 phylogenetic tree, EV79 occupies a distinct branch strongly suggesting that it represents a new serotype/enteroviral species. Because of their high scores in an EV79 VP1 blast search, a number of Simian Picornaviruses (SPV 1 to 45) were included in the analysis. Surprisingly, the EV79 VP1 clusters with a group of Simian Picornavirus VP1 orthologs, exhibiting 72 to 70% sequence similarity to Simian enterovirus 13 and 18 respectively. This suggests a simian origin for EV79 and hence could be the first example of zoonotic potential among enteroviruses.

In an alignment of full-length genomic sequences of 55 Picornavirus isolates, three groups could be distinguished. For the group encompassing most of the human enteroviruses, primers and a nested RT-PCR assay were designed capable of amplifying all members of the group. This assay was used to screen clinical stool samples of 201 HIV-positive subjects, 17 of which yielded a PCR product of the predicted (300 bp) size. Four of these samples showed a band of 450 bp after the first amplification, indicative of high virus titers. Cloned fragments of two PCR products exhibited 89 and 91% homology to the 5'-UTR of human enterovirus 71 and poliovirus respectively.

TABLE 1A

Picorna group 2 amplification primers

| Prime Name | Target virus | Sequence (5'-3') | Remarks | Length of Amplicon |
|---|---|---|---|---|
| PICG2U1 | Picorna group 2 | GGTACCTTTGTRCGCCTGT (SEQ ID NO:1) | 5', first PCR | 450 bp |
| PICG2D1 | Picorna group 2 | GACACCCAAAGTAGTCGG (SEQ ID NO:2) | 3', first PCR | |
| PICG2U1' | Picorna group 2 | CAAGCACTTCTGTTTCCCC (SEQ ID NO:3) | 5', nested PCR | 300 bp |
| PICG2D1' | Picorna group 2 | CATCGRCCTGATCTACAC (SEQ ID NO:4) | 3', nested PCR | |

Viral RNA Isolation

RNA extraction was performed by using the method described by Boom et al. Briefly, 100 µl of clinical specimen or reconstructed specimen from enterovirus panels was mixed with 900 µl of L6 lysis buffer, 50 µl of silica and then incubated for 10 minutes at room temperature. After washing silica particles bound with nucleic acid for several steps, RNA was eluted in 50 µl of nuclease-free water.

Nested RT-PCR Amplification for Discovery

After viral RNA isolation, 10 µl of elution containing isolated RNA was used for nested RT-PCR amplification tests. A downstream primer, named PICG2D1 (5'-GACAC-CCAAAGTAGTCGG-3') (SEQ ID NO:2) and derived from 5'-untranslated region (5'-UTR) region of enteroviruses, were used for the cDNA synthesis. First and second strand cDNA synthesis was performed as described previously (De Wolf et al., 1994). Briefly, after incubation for 45 minutes at 42° C. to synthesize the first strand cDNA, the corresponding generic upstream primer of the first PCR amplification, named PICG2U1 (5'-GGTACCTTTGTRCGCCTGT3') (SEQ ID NO:1), PCR buffer, deoxynucleotide triphosphates, 2.5 mM MgCl$_2$, and 2 U of Taq polymerase (Perkin-Elmer Cetus) were added. After an incubation for 5 minutes at 95° C., the reaction mixture was subjected to 35 cycles of amplification with the following profile: 95° C. for 1 minute, 55° C. for 1 minute, and 72° C. for 2 minutes. After the first PCR amplification, 5 µl of PCR product was added to the nested PCR reaction mixture consisting of a nested upstream primer, named PICG2U1' (5'-CAAGCACTTCTGTTTCCCC-3') (SEQ ID NO:3) and a nested generic downstream primer, named PICG2D1' (5'-CATCGRCCTGATCTACAC-3') (SEQ ID NO:4). The reaction mixture was subjected to 25 cycles of amplification with the same profile as the first PCR amplification. The target fragments, which were approximately 450 bp in length for the first PCR product or 300 bp in length for the nested PCR product, were cloned into the pCRII-TOPO vector (Invitrogen, Carlsbad, Calif.) for plasmid preparation and subsequently gene sequencing reactions.

DNA Sequencing and Analysis

Enterovirus-PCR product containing plasmids were sequenced with the BigDye™ Terminator Cycle Sequencing Kit (Applied Biosystems, Foster City, Calif.), using its −21 M13 and M13 reverse primers. Electrophoresis of sequencing reaction mixtures was performed with an Applied Biosystems 377 automated sequencer, following the manufacturer's protocols. The Vector NTI suite 7 software package was used to analyze all sequencing data.

Determining the Nucleotide Sequence of the Complete Prima 7 Genome

With a third oligonucleotide (07VP4D1, AGCTTCCAC-CACCACCC) (SEQ ID NO:5), located in a conserved domain of the Picorna VP4 region, the sequence for clone 07 was extended to 1034 nucleotides (see FIG. 5).

The resulting deduced amino acid sequence of the putative VP4 region occupies a distinct branch within the phylogenetic tree and clusters in the enterovirus 70 group, identifying it as a novel enterovirus. Using a combination of primers targeting conserved domains and the proprietary PALM method, we are in the process of determining the full-length genomic sequence for this new enterovirus.

Sequence Extension with Deduced Oligonucleotides

By alignment of the deduced amino acid sequences of the related enteroviruses 70, 71 and Coxsackie A16, conserved domains were identified. After back-translation of these conserved protein domains (Table 2), taking into account the appropriate codon bias, degenerate primers could be designed and used for RT-PCR. By selecting appropriate combinations and orientations of the oligos from Table 2, overlapping fragments of the Prima 7 genomic RNA can be amplified by RT-PCR. From these overlapping fragments the complete genome sequence can be assembled.

Palm

Alternatively, using a combination of 5'-oligonucleotides located in the analyzed part of the Prima 7 genome (Table 3, 07UVP01 to 07UVP07) and a 3' tagged random primer (JZH2R) additional fragments of the EV79 genome were amplified using a nested RT-PCR protocol similar to the one mentioned previously.

TABLE 2

Primers targeting conserved domains within the Prima 7 open reading frame

| Conserved domain | Deduced Oligonucleotide | Position Cox A16 | Position Entero 71 | Position Entero 70 |
|---|---|---|---|---|
| GYDASLSPVWF | GARATYCAYGARWSBATYMGVTGGACNAARGAY[1] | 7132 | 7128 | ND |
| 1 | (SEQ ID NO:13) | 7164 | 7161 | |
| (SEQ ID | GARATYCAYGARTCWATWMGATGGACMAARGAY[2] | | Consensus | |
| NO:6) | (SEQ ID NO:14) | | | |
| AGQCGGVVT | GCNGGNCARTGYGGNGGNGTSGTSACN[1] | 5824 | 5820 | 5818 |
| 2 | (SEQ ID NO:15) | 5850 | 5846 | 5844 |
| (SEQ ID | GCIGGRCARTGTGGWGGIGTGGTSACM[2] | | Consensus | |
| NO:7) | (SEQ ID NO:16) | | | |
| NEKFRDI | AAYGARAARTTYMGVGAYATY[1] | 5632 | 5628 | 5626 |
| 3 | (SEQ ID NO:17) | 5652 | 5648 | 5646 |
| (SEQ ID | AATGARAARTTYAGRGAYATCAS[2] | | Consensus | |
| NO:8) | (SEQ ID NO:18) | | | |
| QMVSTVD | CARATGGTNWSNACNGTNGAY[1] | 4657 | 4653 | 4639 |
| 4 | (SEQ ID NO:19) | 4677 | 4673 | 4659 |
| (SEQ ID | CARATGGTRTCYACYGTRGAY[2] | | Consensus | |
| NO:9) | (SEQ ID NO:20) | | | |
| FDGYKQQ | TTYGAYGGNTAYAARCARCAR[1] | 4573 | 4569 | 4555 |
| 5 | (SEQ ID NO:21) | 4593 | 4589 | 4575 |
| (SEQ ID | TTTGAYGGRTAYAAACARCAR[2] | | Consensus | |
| NO:10) | (SEQ ID NO:22) | | | |
| GSPGTGK | GGNWSNCCNGGNACNGGNAAR[1] | 4468 | 4464 | 4450 |
| 6 | (SEQ ID NO:23) | 4488 | 4484 | 4470 |
| (SEQ ID | GGMTCWCCAGGYACTGGRAARTC[2] | | Consensus | |
| NO:11) | (SEQ ID NO:24) | | | |
| AFGTGFT | GCNTTYGGNACNGGNTTYACN[1] | 3820 | 3816 | 3802 |
| 7 | (SEQ ID NO:25) | 3840 | 3836 | 3822 |

TABLE 2-continued Primers targeting conserved domains within the Prima 7 open reading frame

| Conserved domain | Deduced Oligonucleotide | Position Cox A16 | Position Entero 71 | Position Entero 70 |
|---|---|---|---|---|
| (SEQ ID NO:12) | GCITTYGGRACWGGITTYACTGA[2] (SEQ ID NO:26) | | Consensus | |

[1]Using maximum codon degeneracy
[2]Using sequence preference in the aligned viral genomes

TABLE 3

Oligonucleotides for PALM extension of the Prima 7 Sequence

| Oligonucleotide name | Application | Sequence 5'-3' |
|---|---|---|
| JZH2R (SEQ ID NO:27) | 1st PCR | GCTATCATCACAATGGACNNNNNG |
| JZH1 (SEQ ID NO:28) | 1st PCR | GCTATCATCACAATGGAC |
| 07UVP01 (SEQ ID NO:29) | 1st PCR | TTCACTCAACCTGTTGTGG |
| 07UVP02 (SEQ ID NO:30) | 2nd PCR | CACTCAAATCACCATCAGC |
| 07UVP03 (SEQ ID NO:31) | 1st PCR | GCCAGATCGAGTAGACACTA |
| 07UVF04 (SEQ ID NO:32) | 2nd PCR | ATGCAACACAACCTGG |
| 07UVP05 (SEQ ID NO:33) | 1st PCR | TGAAGGAGCCACTACAGCTATACC |
| 07UVF06 (SEQ ID NO:34) | 2nd PCR | ACTGCAGATGATGGTGTCTCAGCA |

Propagation of Prima 7 in Cell Culture

Clinical feces samples were resuspended (30% v/v) in medium B (25 g/L Nutrient Broth No. 2 Oxoid, 250 u/mL Penicillin, 250 µg/mL Streptomycin 1.5 µg/mL Amphotericin B). The growth medium was removed from tubes containing cultured cells (Vero-, human embryonic lung fibroblasts or monkey kidney-cells) with a heat-sterilized platinum needle medium-sucking device. Feces, stored in medium B, were centrifuged at 2500 RPM for 10 minutes and 1 ml of the resulting supernatant was filtered through a 45 µM syringe-mounted filter. 3-4 droplets of the filtrate were added to the cultured cells. The closed tubes were gently inverted to ensure the patient material is in contact with the cells attached to the glass wall and the tubes were incubated for 30 minutes at 37° C. MEM Hanks 8% FCS (Gibco) solution was equilibrated at room temperature and 0.375 μg/mL Amphotericin B and 10 mg/mL Neomycin (Gibco) were added. To each tube 1 ml MEM Hanks 8% FCS was added and the tubes were incubated at 37° C. Twice a week for at least two weeks, the cells are microscopically observed and a virus-specific cytopathic effect (CPE) is scored.

Method to Detect Prima 7 in Stool Samples

Based on the Prima 7 sequence (Table 4), two sets of nested oligonucleotides were designed and RNA extraction was performed as previously described. After viral RNA isolation, 10 μl of elution containing isolated RNA was used for nested RT-PCR amplification tests. A downstream primer, named EV07D1 was used for the cDNA synthesis.

TABLE 4

Prima 7 detection oligonucleotides

| Primer name | Application | Sequence 5'-3' |
|---|---|---|
| EV07U1 (SEQ ID NO:35) | 1st PCR | CAGAGATCTTGCATACCTGT |
| EV07D1 (SEQ ID NO:36) | 1st PCR | AGTATCCTTGGAGTATTCGGGC |
| EV07U2 (SEQ ID NO:37) | 2nd PCR | GAACCAGAACATAGCTGCTAGC |
| EV07D2 (SEQ ID NO:38) | 2nd PCR | CACCATATCCGACTGTGATG |

First and second strand cDNA synthesis was performed as described previously.[6] Briefly, after an incubation for 45 minutes at 42° C. to synthesize the first strand cDNA, the corresponding generic upstream primer of the first PCR amplification, named EV07U1, PCR buffer, deoxynucleotide triphosphates, 2.5 mM $MgCl_2$, and 2 U of Taq polymerase (Perkin-Elmer Cetus) were added. After an incubation of 5 minutes at 95° C., the reaction mixture was subjected to 35 cycles of amplification with the following profile: 95° C. for 1 minute, 55° C. for 1 minute, and 72° C. for 2 minutes. After the first PCR amplification, 5 μl of PCR product was added to the nested PCR reaction mixture consisting of a nested upstream primer, named EV07U2 and downstream primer, named EV07D2. The reaction mixture was subjected to 25 cycles of amplification with the same profile as the first PCR amplification.

Method of Raising Polyclonal Antibodies

Appropriate domains within the Prima 7 polyprotein (e.g., VP1 or VP4) can be selected and amplified with suitable oligonucleotides and RT-PCR. The corresponding purified viral antigens can be obtained by expression in a suitable host (e.g., *Yarrowia lipolytica* as described in Nicaud et al.[16] Female NZW rabbits (approx 4 kg) are primed with 0.5 to 5.0 mg of viral protein antigen preparation. The antigen is suspended in 0.5 ml. of phosphate buffered saline (pH 7.3) and emulsified in an equal volume of complete Freund's adjuvant (CFA). Freund's Adjuvant is a well-established adjuvant system that is appropriate for use in these experiments where small amounts of antigen are used, and where immunogenicity of the antigen (although likely) is unknown. Published guidelines for use will be followed, including limiting injection to 0.1 ml at each site, using CFA only for initial immunization dose. This antigen preparation (1 ml total volume) is injected subdermally in the loose skin on the backside of the rabbit's neck. This injection route is immunologically effective and minimizes the possibility of local inflammation associated with unilateral or bilateral flank injection (such ensuing flank inflammation can impair animal mobility). After resting for 3 weeks, one ml of blood will be removed from the ear artery for a test bleed. Antibodies will be boosted if titers of the desirable antibodies are judged to be too low. Rabbits with adequate antibody levels will be boosted subdermally 1.0 mg of antigen contained in CFA. Boosted animals will be bled after two weeks; i.e., 15 ml of blood will be taken from the ear artery using a heat lamp to dilate the blood vessel. The rabbit will be placed in a commercial restraint, tranquilized with xylazine not more than seven times in total after which the rabbit will be exsanguinated by cardiac puncture following anesthesia using xylazine/ketamine.

Method for Vaccine Production

For the production of a subunit vaccine, the VP1 domain, perhaps combined with the VP2 and VP3 proteins, could be expressed in a suitable eukaryotic host (e.g., *Y. lipolytica* or Vero cells) and purified using preferentially two small affinity tags (e.g., His-tag or the StrepII tag). After appropriate purification, the resulting viral proteins can be used as a subunit vaccine.

Alternatively, the Prima 7 virus can be propagated in Verocells as described above and subsequently treated as described by Wu et al.[28] Briefly the virus is precipitated from culture medium with 20% polyethylene glycol 6000 and purified by ultracentrifugation at 80,000×g for 4 hours through a discontinuous 40-65% sucrose gradient followed by a linear 5 to 40% CsCl gradient for 4 hours at 120,000×g. The resulting virus preparation can be inactivated by heating for 30 minutes at 65° C. as described by Blondel et al.[3]

Analysis of VP1 or any of the Prima 7 Viral Proteins Binding to an Immobilized Ligand (e.g., Antibody) in an Optical Biosensor Binding reactions were carried out in an IAsys two-channel resonant mirror biosensor at 20° C. (Affinity Sensors, Saxon Hill, Cambridge, United Kingdom) with minor modifications. Planar biotin surfaces, with which a signal of 600 arc s corresponds to 1 ng of bound protein/mm2, were derivatized with streptavidin according to the manufacturer's instructions. Controls showed that the viral proteins did not bind to streptavidin-derivatized biotin surfaces (result not shown). Biotinylated antibody was immobilized on planar streptavidin-derivatized surfaces, which were then washed with PBS. The distribution of the immobilized ligand and of the bound VP1 on the surface of the biosensor cuvette was inspected by the resonance scan, which showed that at all times these molecules were distributed uniformly on the sensor surface and therefore were not micro-aggregated. Binding assays were conducted in a final volume of 30 µl of PBS at 20±0.1° C. The ligate was added at a known concentration in 1 µl to 5 µl of PBS to the cuvette to give a final concentration of VP1 ranging from 14 to 70 nM. To remove residual bound ligate after the dissociation phase, and thus regenerate the immobilized ligand, the cuvette was washed three times with 50 µl of 2 M NaCl-10 mM $Na_2HPO_4$, pH 7.2, and three times with 50 µl of 20 mM HCl. Data were pooled from experiments carried out with different amounts of immobilized antibody (0.2, 0.6, and 1.2 ng/mm²). For the calculation of $k_{on}$, low concentrations of ligate (VP1) were used, whereas for the measurement of $k_{off}$, higher concentrations of ligate were employed (1 µM) to avoid any rebinding artifacts. The binding parameters $k_{on}$ and $k_{off}$ were calculated from the association and dissociation phases of the binding reactions, respectively, using the non-linear curve-fitting FastFit software (Affinity Sensors) provided with the instrument. The dissociation constant ($K_d$) was calculated from the association and dissociation rate constants and from the extent of binding observed near equilibrium.

Method to Detect Prima 7 in Stool Samples

Based on the Prima 7 sequence (Table 5), two sets of nested oligonucleotides were designed and RNA extraction was performed as previously described.[4] After viral RNA isolation, 10 µl of elution containing isolated RNA was used for nested RT-PCR amplification tests. A downstream primer, named EV07D1 was used for the cDNA synthesis.

TABLE 5

Prima 7 detection oligonucleotides

| Primer name | Application | Sequence 5'-3' |
|---|---|---|
| EV07U1 (SEQ ID NO:35) | 1st PCR | CAGAGATCTTGCATACCTGT |
| EV07D1 (SEQ ID NO:36) | 1st PCR | AGTATCCTTGGAGTATTCGGGC |
| EV07U2 (SEQ ID NO:37) | 2nd PCR | GAACCAGAACATAGCTGCTAGC |
| EV07D2 (SEQ ID NO:38) | 2nd PCR | CACCATATCCGACTGTGATG |

First and second strand cDNA synthesis was performed as described previously (De Wolf et al., 1994). Briefly, after an incubation for 45 minutes at 42° C. to synthesize the first strand cDNA, the corresponding generic upstream primer of the first PCR amplification, named EV07U1, PCR buffer, deoxynucleotide triphosphates, 2.5 mM $MgCl_2$, and 2 U of Taq polymerase (Perkin-Elmer Cetus) were added. After an incubation for 5 minutes at 95° C., the reaction mixture was subjected to 35 cycles of amplification with the following profile: 95° C. for 1 minute, 55° C. for 1 minute, and 72° C. for 2 minutes. After the first PCR amplification, 5 µl of PCR product was added to the nested PCR reaction mixture consisting of a nested upstream primer, named EV07U2 and downstream primer, named EV07D2. The reaction mixture was subjected to 25 cycles of amplification with the same profile as the first PCR amplification. The PCR products were size fractionated on a 1% agarose gel, excised, purified using the Qiaquick columns according to the protocol supplied by the manufacturer (Qiagen, Westburg), cloned into pCRII (Invitrogen) via topoisomerase 1-mediated ligation. For each PCR product, plasmids from three randomly picked colonies were isolated using a Qiagen Spin Miniprep kit and analyzed using the Big-Dye (Applied Biosystems) sequencing protocol. Results are depicted in FIG. 4.

Nucleic Acid Sequence

By a combination of the PALM method, long range RT-PCR and 5'-RACE the complete nucleotide sequence of Enterovirus Prima 7 was obtained.

Phylogenetic analysis revealed that Prima 7 clusters with group A of human enteroviruses. The most closely related group A members are Enterovirus 71 and Coxsackie A16 which exhibit 68% overall sequence identity at the nucleic acid level (Table 4).

To exclude the possibility that Prima 7 (EV79 in all Figures) occupies a separate branch in the phylogenetic tree because it is an inter-group recombinant, we performed a SimPlot analysis[13] with reference sequences of human enterovirus groups A, B, C, D and E. Throughout its genome Prima 7 maintained the strongest similarity to group A enteroviruses, suggesting Prima 7 is not an inter-group recombinant.

When the Prima 7 sequence was used as query in a SimPlot analysis comparing it to all available full-length human group A Enteroviruses, it appeared to be equidistant to all of them. If however, any other group A enterovirus is used as query sequence, Prima 7 exhibits the lowest similarity throughout its genome. This suggests strongly that Prima 7 is a new group A enterovirus and not merely a recombinant from two distantly related group A enteroviruses.

Hybrid Genomes

The first chimeric genome was generated by a reciprocal recombination in the VP3, fusing nucleotide 2187 of Coxsackie virus A16 (NC_001612) to nucleotide 2129 of EV79. Recombination occurred at the conserved sequence TGGGA, retaining the large open reading frame and generating a hybrid polyprotein.

A second chimeric genome was generated by a reciprocal recombination fusing nucleotide 3773 of Enterovirus 71 (U22522) to nucleotide 3713 of EV79 again creating a hybrid 2b-encoding domain within polyprotein. Recombination has occurred within the conserved sequence ATGGA.

Untranslated Regions

The strongest sequence conservation is encountered in the 5' untranslated region (5'-UTR), probably because this region plays a pivotal role in the replication and initiation of protein synthesis.[22] Inverted repeats in the 5'-UTR allow extensive internal base pairing and the resulting secondary structure can be predicted using the M-Fold program.[14] The initiation codon resides immediately downstream of a CT rich tract (position 643-660) which is part of a putative Internal Ribosome Entry Site (IRES) or ribosome landing pad. This ATG corresponds to the one we identified as initiation codon on the basis of homology. All seven other ATGs preceding the putative initiation codon are out of frame and, according to the M-fold prediction, sequestered in hairpin loops.

Open Reading Frame Analysis

Assuming the ATG in position 683 is the initiation codon we obtain an ORF of 2193 AA. Blast searches were used to tentatively identify the proteolytic cleavage products of the encoded polyprotein.

TABLE 6

Prima 7 encoded proteins

| Protein | Position | Number AAs | Deduced Mw |
|---|---|---|---|
| VP4* | 686-889 | 68 | 7.282 |
| VP2 | 890-1654 | 255 | 27.912 |
| VP3 | 1655-2386 | 244 | 26.578 |
| VP1 | 2387-3271 | 295 | 32.471 |
| 2A | 3272-3721 | 150 | 16.460 |
| 2B | 3722-4018 | 99 | 10.730 |
| 2C | 4019-5002 | 329 | 36.974 |
| 3A | 5003-5257 | 85 | 9.602 |
| 3B | 5258-5323 | 22 | 2.274 |
| 3C | 5324-5872 | 183 | 20.153 |
| POL | 5873-7258 | 462 | 52.746 |
| Total | 683-7258 | 2193 | 243.141 |

*It is assumed that the N-terminal methionine residue is removed, prior to myristylation of VP4

Table 10

VP4 capsid protein (PFAM02226) (SEQ ID NO:39) (M) GAQVSTQKTGSHENQNIAASGSTINYT-TINYYKDSYAASAAKQDFSQDPSKFTQPVVDA LKET-APPLK The VP4 capsid protein contains an N-terminal myristylation consensus site GXXXS/T[19] (SEQ ID NO:84)

VP2 capsid protein (CD00205, PFAM00073) (SEQ ID NO:40)

SPSAEACGYSDRVAQLTLGNSTITTQEAANITVGYGEWPEYSKDTEATA

VDKPTRPDVSVNRFYTLPAKLWANNSKGWYWKFPDVLCELGVFGQNAQY

HYLYRSGFCIHVQCNASKFHQGTLLVAAIPELMLARSSNDTNPATAPHP

PYNATQPGEAGKEFAYPYILDSGIPLSQALIFPHQWINLRTNNCATIVM

PYINCLPFDSALNHCNFSLVVIPVAPLAYNEGATTAIPITVTVAPMCSE

FSGLRQAVVQ

VP3 capsid protein (CD00205, PFAM00073) (SEQ ID NO:41)

GLPAELKPGTNQFLTTDDGVSAPILPGFHPTPEMHIPGEVKNLLEICQV

ESILEVNNLTTNKAASQLMTRLLIPVEAQTAVDALCAAFKVDPGRDGPW

QSTLVGQICRYYTQWSGSLEVTFMFTGSFMATGKMLIAYTPPGAPQPAN

RRIAMLGTHVIWDFGLQSSVTLVIPWISNTHYRAMGSNDYFDYYSAGIV

TIWYQTNFVVPSGAPTSAYIIALAAAQKNFTLRLPKDTGDISQTAILQ

VP1 capsid protein (CD00205) (SEQ ID NO:42)

GDPIEEAINNTVAGTLNRALGSASHTTAQNTQQSSHQIGTGEVPALQAA

ETGATSNTSDENMLETRCVINSHSVAETSISHFFSRAGLVGMLDLLTSG

DTDIGFTSWDIDIMGFVQQRRKLEMFTYMRFDAEFTFLTVGATGAAPAT

VIQYMYVPPGAPKPTQRDSFEWQTSTNPSIFVKVSDPPAQVSVPFMSPA

AAYQWFYDGYPTFGNHPTNQDFRYGICPNNLMGTFCVRVLGSEKLTEAL

RVRIYMRIKHVRAWIPRPLRSQKYLLKNYPNFDGADVTPTSASRANITT

A

Capsid Proteins as Vaccine

Neutralizing antibodies against poliovirus target epitopes in VP2, VP3 and VP1[15] and for EV71 VP1 has been proposed as primary target for vaccine production.[24,28]

Additionally, detecting IgG and IgM immune responses against linear epitopes of recombinant VP1 is an effective means of determining the different phases of enterovirus 71 infection.[24]

The elements determining pathogenicity and tissue tropism have been localized in VP1[26] and the 5'-UTR. For Coxsackievirus A9, modification of the conserved sequence motif PALTAVETGHT (SEQ ID NO:43) results in a reduced capacity to produce infectious progeny virus.[1] The Enterovirus 79 VP1 contains a similar sequence motif (in red print, yellow background), so we could claim modification of conserved sequence motifs (indicated in red) as a tool to obtain attenuated strains. Additionally, the three dimensional structure of VP1 harbors an apolar pocket, usually containing a small hydrophobic molecule (pocket factor).[22] New antivirals target this apolar pocket, displacing the pocket factor and interfering with the uncoating of the viral genome. We could claim recombinant VP1 as a screening tool for such antiviral compounds.

VP1 could be expressed in a suitable microbial host (e.g., *Escherichia coli*) as an affinity tagged protein (e.g., His tag and or StrepII tag).

The VP2, VP3 and VP1 protein encoding cDNAs can be amplified by RT-PCR using oligonucleotide pairs VP2-VP2R, VP3F-VP3R and VP1F-VP1R respectively. The PCR primers add attB1 and attB2 sites to respectively the 5' and 3' end of all three amplicons. The resulting PCR products of 818, 785 and 938 bp can be inserted into pDONR201 (Invitrogen) by Topoisomerase-mediated ligation generating entry clones for the Gateway system (Invitrogen). The Gateway system allows directional transfer of any sequence located between attB1 and attB2 sites through an efficient in-vitro recombination reaction. Invitrogen supplies Gateway compatible expression vectors for a number of hosts like *Escherichia coli* (e.g., pBAD-DEST49, pDEST17) *Saccharomyces cerevisiae* (e.g., pYES2-DEST52), Baculovirus (e.g., pDEST20) as well as insect-(pMT-DEST48) and mammalian cell lines (e.g pT-REX-DEST31).

As an example, the EV79-derived PCR cDNA fragments for VP2, VP3 and VP1 were ligated into pDONR201 and transferred to the pThio-HisB (Invitrogen) Gateway derivative pGP7 to give pEV2, pEV3 and pEV4. The expression construct pEV1 to 3 direct production of VP fusion proteins in *E. coli* bearing an N-terminal His-tagged thioredoxin domain, which acts as a solubility-enhancing cassette, and a C-terminal StrepII affinity tag. The His- and StrepII affinity tag facilitate detection and recovery. The first step in protein recovery is the lysis of the host cells in buffer containing a suitable cocktail of protease inhibitors. Any inclusion bodies are solubilized by sonication in the presence of 8 M urea. The cleared lysates were loaded on columns containing NiNTA resin (Qiagen) and subjected to metal affinity purification according to the manufacturer's protocol. The eluates of the metal affinity purification were diluted with a suitable buffer and transferred to Streptactin columns as prescribed by the manufacturer (IBA GmbH). In this way, purified proteins can be produced in *E. coli*.

TABLE 7

Amplification oligos for expression of VP2, VP3 and VP1 fusion protein

| Oligo | Sequence |
|---|---|
| P2F (SEQ ID NO: 44) | ACAAGTTTGTACAAAAAAGCAGGCTTCTCACCATCAGCTGAAG CATGTGGC |
| P2R (SEQ ID NO: 45) | ACCACTTTGTACAAGAAAGCTGGGTCTTGAACCACAGCTTGC CTAAGACC |
| P3F (SEQ ID NO: 46) | ACAAGTTTGTACAAAAAAGCAGGCTTCGGACTACCGGCAGAAT TAAAACC |
| P3R (SEQ ID NO: 47) | ACCACTTTGTACAAGAAAGCTGGGTCTTGCAGGATGGCGGTTT GTGAG |

TABLE 7-continued

Amplification oligos for expression of VP2, VP3 and VP1 fusion protein

| Oligo | Sequence |
|---|---|
| P1F (SEQ ID NO: 48) | ACAAGTTTGTACAAAAAAGCAGGCTTCGGTGACCCTATTGAAG AGGCCATC |
| P1R (SEQ ID NO: 49) | ACCACTTTGTACAAGAAAGCTGGGTCAGCTGTTGTGATATTGG CTCTAGATGC |

The VP2, VP3 and VP1 complementary sequences are indicated in bold print. The remainder of the PCR primers is composed of either in-frame attB1 or attB2 sites

TABLE 11 some EV79 proteins 2A protease (PFAM00947) (SEQ ID NO:50)
GVFGQQSGAVYVGNYKIVNRHLATEADWNSLVWESYNRDLLVTSVNAQGC
DTIARCSCKAGVYFCKSMNKHYPVSFQGPGIVEVQANEFYPHRYQTHVLL
GHGTSIPGDCGGILRCQHGVIGLVTMGGDGLVGFADLRDLFWLDDEAMEQ 2B (Pico_2B PFAM01552) permeability enhancing
protein (SEQ ID NO:51)
GVTDYIKGLGDAFGTGFTDSISREIQQLKNYLLGSENVVEKILKALIKVV
SALVIVVRSDYDLVTLTATLALIGCHGSPWAWLKSKVSNLLDIPIAQKQ 2C (RNA helicase PFAM00910) (SEQ ID NO:52)
SDSWLKKFTEMANAARGLEWIANKISKFIDWVKEKIVPAAKEKVEFLSNL
KQLPLLESQIANIEQSAASQEDLENLFSNVAYLAHYCRKFQPLYASEAKR
IYAMEKRINNYMQFKSKHRIEPVCLIIRGPPGTGKSLATGIIGRAIAEKY
HSSVYSLPPDPDHFDGYKQQVVTVMDDLCQNPDGKDMSLFCQMVSTVEFI
PPMASLEEKGVSFTSKFVIASTNSSNIIVPTVSDSDAIRRRFYMDCDIEV
PESFRTPQGRLDAARAAKLCSENNTANFKKCSPLVCGKAIQLRDRKSGVR
YGLDSVVSELIREYNNRSAVGNTIEALFQ 3A (SEQ ID NO:53)
GPPQFKPIRITLDKPAPDAISDLLASVDSEEVRQYCRHQGWIIPEKPTNI
ERHVNRALMILQSVTTVVAVISLVYVIYKLFAGFQ 3B or VPg (SEQ ID NO:54)
GAYSGMPKTAVKKPVLRTAVAQ 3C protease (PFAM00548) (SEQ ID NO:55)
GPGLDFALSLLKKNIRKCQTDQGHFTLLGIRDRLAVLPRHASPGDSIWIE
HKQIKILDAVELVDEQQVNLELTLITLDTNEKFRDITKFIPEQIEGTADA
TLVINTEAMPSMFVPVGDVQQYGFLNLSGKPTHRTMMYNFPTKAGQCGGV
VTSVGRIVGIHIGGNGRQGFCAALKRSYFASEQ 3D or POL RNA dependant RNA Polymerase
(PFAM00680) (SEQ ID NO:56)
GEIQWMKSNKETGNFNINGPTKTKLEPSVFHDVFEGVKEPAVLHSKDKRL
EVDFETALFSKYIGNKMHEPDEYMIQAANHYADQLKQLDIDTSKMSMEDA
CYGTEFLEGIDLATSAGYPYNALGIKKKDILNPQTRDVTKMKMYLDKYGI
DLPYSTYVKDELRAKDKIKKGKSRLIEASSINDSVYLRMCFGHLYEKFHA
NPGTITGSAVGCNPDTFWSKIPIMLPGSLFAFDYTGYDASLSPAWFRALE
IVLKRLGYDQDAISLIEGINHSHHIYRNQTYCVMGGMPSGCSGTSIFNSM
INNIIIRTLLIRTFKGIDLDELNMIAYGDDVLASYPFPIDCAELAKTGLE
YGLVMTPADKSTCFNEVNWENATFLKRGFKPDEQYPFLIHPTMPMKEIHE
SIRWTKDPRNTQDHVRSLCLLAWHNGRETYEEFVDKIRTVPIGKVLALPN
YDNLRRNWLELF The 2A protease catalyzes its own release from the polyprotein and the inactivation of the host translational initiation factor eIF4Q[9,21] which results in the shut down of host protein synthesis after which the IRES dependant viral translation takes over.[25] Any compound interfering with this function could be used as an antiviral.

Expression of Coxsackie 2B gradually enhances membrane permeability thereby disrupting the intracellular $Ca^{2+}$ homeostasis and ultimately causing the membrane lesions that allow release of virus progeny.[26] Any compound interfering with this function could be used as an antiviral.

3B or VPg: This protein is covalently attached to the 5' end of the viral genomic RNA.

TABLE 8

Overall protein similarity to most closely related human group A Enteroviruses

|  | EV71 AAD44710 | CoxA16 AAD55085 | EV5865 AAK13008 | CoxA16 NP0042242 | EV5666 AAK30618 | EV79 |
|---|---|---|---|---|---|---|
| EV71 AAD44710 | 100 | 89 | 96 | 89 | 95 | 77 |
| CoxA16 AAD55085 |  | 100 | 90 | 95 | 89 | 77 |
| EV5865 AAK13008 |  |  | 100 | 90 | 99 | 77 |
| CoxA16 NP0042242 |  |  |  | 100 | 89 | 77 |
| EV5666 AAK30618 |  |  |  |  | 100 | 77 |
| EV79 |  |  |  |  |  | 100 |

Example Use of the EV79 Internal Ribosome Entry Site (IRES).

Expression vector pLXRN (GenBank Accession number AF113968) uses a retroviral Long Terminal Repeat (LTR) to drive expression of any cDNA cloned into its polylinker. LTR activity results in transcription of a bicistronic mRNA of which the first open reading frame encodes the protein to be expressed and the second open reading frame encodes the eukaryotic neomycin selection marker. The first and second ORF are separated by an encephalomyocarditis virus-derived IRES, that assures efficient translation of the neomycin resistance.

To exchange the EMCV IRES by the EV79 IRES, first an NcoI site has to be introduced at the initiation codon of the neomycin resistance gene. The restriction site is generated by site directed mutagenesis employing oligonucleotides pLXRN 1 and 2 with the Quickchange kit according to the instruction of its manufacturer (Stratagene). The resulting pLXRN-derivative is the partially NcoI digested and digested to completion with BamHI. The EV79 IRES (EV79 nucleotide positions 1 to 746, FIG. 19) can be amplified from an EV79-containing clinical sample by RT-PCR with primers IRES5 and IRES3, simultaneously adding a BamHI site to its 5' end and a BspLU11I site at the polyprotein initiation codon. The resulting 762 bp amplicon is BamHI-BspLU11I digested and ligated into the mutagenized pLXRN. The resulting construct is named pEV79 in which the EMCV IRES is replaced by its EV79 ortholog. The pEV79 can be used to transfect mammalian cell lines as previously described.

TABLE 9 pEV79 construction oligonucleotides

| Oligo | Use | Sequence |
|---|---|---|
| PLXRN1 (SEQ ID NO:57) | Mutagenesis PLXRN | GGGATAATTCCTGCAGCCACCATGGGATCGGCCATTGAAC |
| PLXRN2 (SEQ ID NO:58) | Mutagenesis PLXRN | GTTCAATGGCCGATCCCATGGTGGCTGCAGGAATTATCCC |

TABLE 9-continued pEV79 construction oligonucleotides

| Oligo | Use | Sequence |
|---|---|---|
| IRES5 (SEQ ID NO:59) | Amplification EV79 IRES | GGGGATCCTTTAAAACAGCTCTAGGGTTG |
| IRES3 (SEQ ID NO:60) | Amplification EV79 IRES | CCACATGTTCTCTTTCTACTATTCAACTGTATG |

EV79 Could Be of Simian Origin

We have discovered a new species of human enterovirus. EV79 occupies a distinct branch within a VP1-derived phylogenetic tree. Genetic clusters of VP1 sequences, the major picornaviral antigen, have been demonstrated to correlate to serotype.[5, 17] Recently, a new simian Picornaviral genus and several new species have been proposed solely based on VP1 protein alignments.[18] Therefore, EV79 should also represent a new enteroviral serotype. Also in VP2-based and full-length polyprotein-derived phylogenetic trees, EV79 remains distinct from the most closely related group A enteroviruses (e.g., Coxsackie A16 and Enterovirus 71), further strengthening our claim of having discovered a novel enterovirus. The SimPlot analysis shows that throughout its genome, EV79 differs from all other human enteroviruses, excluding the possibility of EV79 arising by inter-species recombination.

Already the close relationship of the simian viruses A13, SV19, 25, 35, 43 and 46 to group A human enteroviruses (e.g., Coxsackie A16 and EV71) prompted already speculations about their potential to infect humans.[18] The even closer relationship of the human isolate EV79 to these simian viruses could be proof of this zoonotic potential.

REFERENCES

1. Caro V., S. Guillot, F. Delpeyroux, and R. Crainic. 2001. Molecular strategy for "serotyping" of human enteroviruses. J. Gen. Virol. 82:79-91.

2. Oberste M. S., K. Maher, D. R. Kilpatrick, M. R. Flemister, B. A. Brown, and M. A. Pallansch. 1999. Typing of human enteroviruses by partial sequencing of VP1. J. Clin. Microbiol. 37:1288-1293.
3. Oberste M. S., K. Maher, and M. A. Pallansch. 2002. Molecular phylogeny and proposed classification of the simian picornaviruses. J. Virol. 76:1244-1251.

What is claimed is:

1. An isolated and/or recombinant nucleic acid comprising a nucleic acid sequence selected from the group consisting of SEQ ID NO:82 and SEQ ID NO:61.

2. An isolated and/or recombinant nucleic acid that is at least 95% homologous to a nucleic acid sequence selected from the group consisting of SEQ ID NO: 82 and SEQ ID NO: 61.

3. An isolated and/or recombinant nucleic acid comprising a stretch of 100 consecutive nucleotides of a nucleic acid sequence selected from the group consisting of SEQ ID NO: 82 and SEQ ID NO: 61.

4. An isolated and/or recombinant nucleic acid encoding a proteinaceous molecule comprising an amino acid sequence selected from the group consisting of SEQ ID NO:83, SEQ ID NO:39, SEQ ID NO:40, SEQ ID NO:41, SEQ ID NO:42, SEQ ID NO:50, SEQ ID NO:51, SEQ ID NO:52, SEQ ID NO:53, SEQ ID NO:54, SEQ ID NO:55, SEQ ID NO:56, and SEQ ID NO:63.

5. An isolated or recombinant virus comprising a nucleic acid sequence according to claim 1.

6. A vector comprising a nucleic acid according to claim 1.

7. A primer and/or probe comprising a nucleic acid sequence selected from the group consisting of SEQ ID NO:35, SEQ ID NO:36, SEQ ID NO:37, and SEQ ID NO:38.

8. A diagnostic kit comprising a primer/probe according to claim 7.

9. An isolated cell comprising a nucleic acid according to claim 1.

10. An isolated cell according to claim 9, wherein said nucleic acid comprises an expressible coding region of SEQ ID NO:82, or a part of said coding region coding for at least a protein comprising a stretch of 30 consecutive amino acids.

11. An isolated cell according to claim 9, wherein said cell is a eukaryotic cell.

12. A gene delivery vehicle comprising a sequence according to claim 1.

13. An attenuated virus according to claim 5.

14. A polycistronic messenger RNA comprising an internal ribosomal entry site (IRES) that comprises positions 1 to 748 of SEQ ID NO:82.

15. A chimeric enterovirus comprising at least 1000 consecutive nucleotides of SEQ ID NO: 82 and at least 1000 consecutive nucleotides of another enterovirus wherein said latter 1000 consecutive nucleotides comprise a sequence that is more than 5% sequence divergent with SEQ ID NO: 82.

16. An isolated cell comprising a vector according to claim 6.

* * * * *